US012797461B2

(12) United States Patent
Mogler et al.

(10) Patent No.: US 12,797,461 B2
(45) Date of Patent: Nov. 17, 2026

(54) SWINE INFLUENZA A VIRUS VACCINE COMPRISING A NUCLEIC ACID CONSTRUCT COMPRISING FIRST, SECOND AND THIRD NUCLEIC ACID SEQUENCES ENCODING DISTINCT NEURAMINIDASE ANTIGENS OF THE VIRUS

(71) Applicant: Intervet Inc., Madison, NJ (US)

(72) Inventors: Mark A. Mogler, Ames, IA (US); Basav Hangalapura Nagaraj, Wageningen (NL)

(73) Assignee: Intervet Inc., Rahway, NJ (US)

( * ) Notice: Subject to any disclaimer, the term of this patent is extended or adjusted under 35 U.S.C. 154(b) by 931 days.

(21) Appl. No.: 18/010,416

(22) PCT Filed: Jun. 18, 2021

(86) PCT No.: PCT/EP2021/066555

§ 371 (c)(1),
(2) Date: Dec. 14, 2022

(87) PCT Pub. No.: WO2021/255225

PCT Pub. Date: Dec. 23, 2021

(65) Prior Publication Data

US 2023/0248817 A1 Aug. 10, 2023

(30) Foreign Application Priority Data

Jun. 19, 2020 (EP) .................................... 20181114

(51) Int. Cl.
*A61K 39/39* (2006.01)
*A61K 39/145* (2006.01)
*A61K 39/00* (2006.01)

(52) U.S. Cl.
CPC ............ *A61K 39/145* (2013.01); *A61K 39/39* (2013.01); *A61K 2039/5258* (2013.01); *A61K 2039/53* (2013.01); *A61K 2039/552* (2013.01); *A61K 2039/55566* (2013.01)

(58) Field of Classification Search
None
See application file for complete search history.

(56) References Cited

U.S. PATENT DOCUMENTS

| | | | | |
|---|---|---|---|---|
| 6,521,235 B2 | 2/2003 | Johnston et al. | | |
| 12,290,556 B2 * | 5/2025 | Mogler | ................ | A61K 39/145 |
| 2023/0265130 A1 * | 8/2023 | Mogler | .................. | A61K 39/12<br>424/209.1 |
| 2023/0277649 A1 * | 9/2023 | Mogler | ................ | A61K 39/145<br>424/186.1 |
| 2025/0281597 A1 * | 9/2025 | Nagaraj | ............. | A61K 39/0258 |

FOREIGN PATENT DOCUMENTS

| | | | |
|---|---|---|---|
| CN | 102154219 | B | 8/2011 |
| CN | 105709220 | B | 6/2016 |
| EA | 011557 | B1 | 4/2009 |
| JP | 2008500399 | A | 1/2008 |
| JP | 2023530132 | A | 7/2023 |
| RU | 2531235 | C2 | 10/2014 |
| RU | 2618918 | C2 | 5/2017 |
| WO | WO 2006082398 | A2 | 8/2006 |
| WO | 2008039267 | A2 | 4/2008 |
| WO | WO 2014126510 | A2 | 8/2014 |
| WO | WO 2016137929 | A1 | 9/2016 |
| WO | 2019121513 | A1 | 6/2019 |
| WO | WO 2019110481 | A1 | 6/2019 |

OTHER PUBLICATIONS

Khishtova, 2007, "Immunobiological preparations for the prevention and treatment of infectious diseases and correction of dysbiocenoses," Immunobiologicheskie, pp. 1-75, in Russian with machine English translation (150 pages).

De Vries, Rory D. et al., Viral vector-based influenza vaccines, Human Vaccines & Immunotherapeutics, 2016, 2881-2901, 12(11).

Erdman, M.M. et al., Alphavirus replicon particle vaccines developed for use in humans induce high levels of antibodies to influenza virus hemagglutinin in swine: Proof of concept, Vaccine, 2010, 594-596, 28(3).

Sandbulte, Matthew et al., Optimal Use of Vaccines for Control of Influenza A Virus in Swine, Vaccines, 2015, 22-73, 3(1).

Liu et al., 2015, "Cross-Reactive Neuraminidase-Inhibiting Antibodies Elicited by Immunization with Recombinant Neuraminidase Proteins of H5N1 and Pandemic H1N1 Influenza A Viruses," J. Virol., 89(14):7224-7234.

Sandbulte et al., 2016, "Neuraminidase inhibiting antibody responses in pigs differ between influenza A virus N2 lineages and by vaccine type," Vaccine, 34(33):3773-3779.

* cited by examiner

*Primary Examiner* — Agnieszka Boesen
(74) *Attorney, Agent, or Firm* — Susanna C. Benn

(57) ABSTRACT

The present invention relates to a nucleic acid construct comprising first, second and third nucleic acid sequences encoding first, second and third neuraminidase (NA) antigens of a Swine influenza A virus (IAV-S). The first NA antigen is of the A/swine/Scotland/410440/1994-like $H1_{hu}N2$ (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}N1$ (EA) lineage. In other embodiments, the present invention relates to RNA replicon particles comprising the nucleic acid construct, an immunogenic composition, such as a vaccine, which may be used against influenza A virus infection, and comprising the replicon particles.

5 Claims, 15 Drawing Sheets

Figure 1:
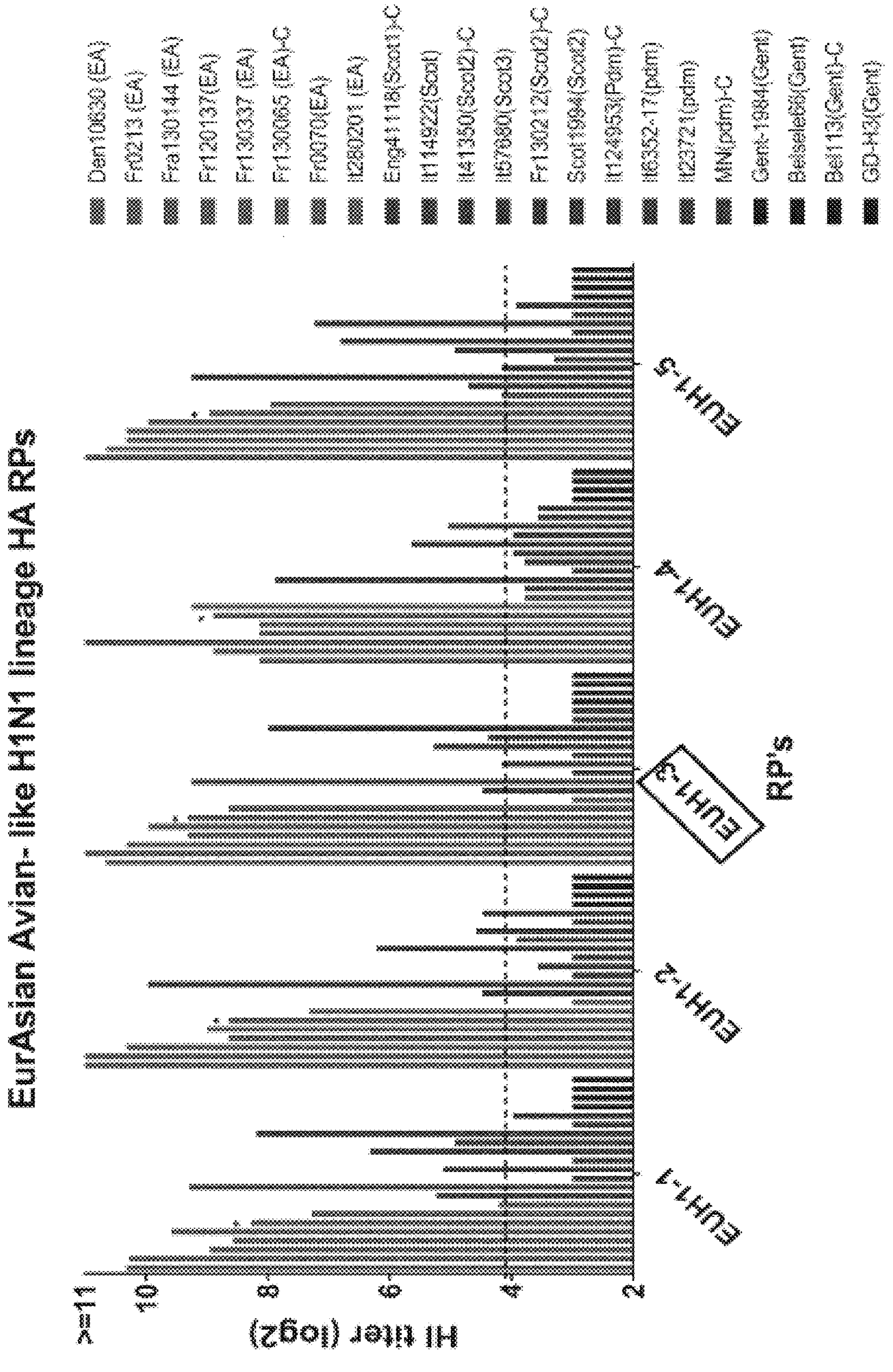

Specification includes a Sequence Listing.

SWINE INFLUENZA A VIRUS VACCINE COMPRISING A NUCLEIC ACID CONSTRUCT COMPRISING FIRST, SECOND AND THIRD NUCLEIC ACID SEQUENCES ENCODING DISTINCT NEURAMINIDASE ANTIGENS OF THE VIRUS

CROSS-REFERENCE TO RELATED APPLICATIONS

This application is a National Stage application of International Patent Application No. PCT/EP2021/066555, filed Jun. 18, 2021, which claims priority to European Patent Application No. EP 20181114.8, filed Jun. 19, 2020.

SEQUENCE LISTING

The instant application contains an electronic Sequence Listing which has been submitted in an ASCII plain text file via the Patent Center, the entire content of which is hereby incorporated by reference in its entirety. The Sequence Listing text file submitted via the Patent Center is entitled "24973-EPPD.txt" and was created on Jun. 9, 2021, and is 71,311 bytes in size.

The present invention relates to a nucleic acid construct comprising first, second and third nucleic acid sequences encoding first, second and third neuraminidase (NA) antigens of a Swine influenza A virus (IAV-S). The first NA antigen is of the A/swine/Scotland/410440/1994-like $H1_{hu}$N2 (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}$N1 (EA) lineage. In other embodiments, the present invention relates to RNA replicon particles comprising the nucleic acid construct, an immunogenic composition, such as a vaccine, which may be used against influenza A virus infection, and comprising the replicon particles.

Further provided is an immunogenic composition, such as a vaccine, comprising first, second and third RNA replicon particles. The first RNA replicon particle comprises a nucleic acid construct, comprising first and second nucleic acid sequences encoding first and second hemagglutinin (HA) antigens of IAV-S. The first HA antigen is of the Gent/84 lineage, and the second HA antigen is of the pdm09 lineage. The second RNA replicon particle comprises a nucleic acid construct comprising third and fourth nucleic acid sequences encoding third and fourth HA antigens of IAV-S, wherein the third HA antigen is of the Scot/94 lineage, and the fourth HA antigen is of the EA lineage. The third RNA replicon particle comprises a nucleic acid construct comprising first, second and third nucleic acid sequences encoding first, second and third NA antigens of IAV-S, wherein the first NA antigen is of the Scot/94 lineage, the second NA antigen is of the Gent/84 lineage, and the third NA antigen is selected from the pdm09 lineage or the EA lineage. Further provided are methods of making the vaccine and use of the vaccine.

BACKGROUND

Influenza A viruses (IAV) create a significant burden on human and animal health, worldwide. IAV is categorized into different subtypes based on its viral surface glycoproteins, hemagglutinin (HA) and neuraminidase (NA). IAV infects poultry, pigs, horses, cats, dogs, marine mammals (e.g., whales), bats and humans. Wild waterfowl and shorebirds (ducks, geese, swans and gulls) are the natural reservoirs and they can be infected with 16 different HA and 9 different NA subtypes [Webster et al., *Microbial Rev* 56:152-179 (1992)].

Influenza A virus in swine (IAV-S) is a serious respiratory pathogen of domestic pigs that has proven to be economically costly, particularly to the livestock industry, worldwide [Holtkamp et al., *The American Association of Swine Veterinarians Annual Meeting* (2007)]. It is characterized by a sudden onset of respiratory illness, and is usually accompanied by anorexia, lethargy, and fever. In addition to the clinical complications associated with IAV-S in production animals, there have been published reports implicating swine in the transfer of influenza viruses to humans [Myers K P, Olsen C W, Gray G C. Clin Infect Dis 2007; 44(8): 1084-8, Krueger and Gray, *Curr Top Microbiol Immunol* 370: 201-225 (2013)], which represents a significant public health threat providing an even greater incentive to control IAV in swine herds.

In response to this problem, many swine farmers now vaccinate their pigs against IAV-S employing commercially available vaccines. However, controlling IAV-S with the conventional vaccines is difficult because many diverse IAV-S strains co-circulate in the field and continue to evolve [Gao et al., *J Gen Virol* 98(8):2001-2010 (2017)]. The diversity and mutability of IAV-S are caused by the virus's genetic structure. Like other influenza A viruses, IAV-S has genes encoded on eight segments of RNA and a genome replication machinery that introduces frequent mutations. These genetic characteristics enable IAV-S to make rapid adaptions, including escape from existing neutralizing antibodies induced by exposure to previous strains. Consequently, inactivated virus IAV-S vaccines that are commercially available in the USA market have proven inadequate despite comprising up to five different IAV-S strains due to newly emerging strains that arise as a consequence of the continuous antigenic drift and or shift.

Classification of influenza A viruses starts with subtyping of HA and NA, the two major glycoproteins on the virus surface. HA protein mediates attachment and fusion of the virus to host cells. Neuraminidase is an enzyme that functions in the final stage of the influenza virus replication cycle by cleaving newly formed viral particles from the host cell, thereby enabling the new progeny virus to spread and infect other cells. Recent research has shown that NA immunity only can play a supplemental and/or complementary role to the more critical HA immunity [Nayak et al., J Virol 84(5): 2408-2420 (2010); Pavlova et al., Vaccine 27(5): 773-785 (2009); Sylte et al., Vaccine 25(19): 3763-72 (2007)]. Indeed, it appears that in the absence of a hemagglutinin antigen, a neuraminidase influenza A virus vaccine is not potent enough to either protect against influenza A infection or protect against an influenza A virus induced disease.

Whereas human influenza A usually has 1 or 2 dominant strains circulating globally during a given influenza season, many more strains of IAV-S co-circulate simultaneously, with these strains differ between geographic regions. Similarly, IAV-S strains are also antigenically variable, but mainly contain an H1 or H3 subtype of HA, and a N1 or N2 subtype of NA. Within each HA and NA subtype of IAV-S there is further phylogenetic diversity.

In the US swine population there are four predominant phylogenetic clusters of H1 (gamma, delta1, delta2, pandemic), two predominant clusters of H3 (cluster IV and human-like), two predominant clusters of N1 (classic, pandemic), and two predominant clusters of N2 (N2-1998 and N2-2002). [See, Anderson et al., *Influenza and other Respi-*

*ratory Viruses* 7 (Suppl. 4); 42-51 (2013); and Anderson et al., *mSphere* 1(6) e00275-16:1-14 (2016)].

In Europe there are three major lineages of H1 (Eurasian-avian like H1, Scotland/410440/1994-like H1 and pandemic 2009 like H1), one major lineage of H3 (Gent/1/1984-like H3), two major lineages of N1 (Eurasian Avian-like N1, Pandemic 2009 like N1), two major lineages of N2 (Gent/1/1984-like N2, Scotland/410440/1994-like N2) and two minor lineages of N2 (Italy/4675/2003 like N2, Human seasonal like N2) [Watson et al., *J. Virol.,* 89:9920-9931 (2015); doi:10.1128/JVI.00840-15].

Vaccination against IAV-S represents the best option for decreasing clinical complications in swine as well as decreasing opportunities for additional reassortment and zoonotic spread from swine to humans. Until recently, the only vaccines available for widespread use are inactivated vaccines prepared from influenza viruses grown in embryonated eggs, but their supply is limited, in large part by a paucity of specific pathogen-free eggs, and the need for new approaches to influenza vaccines is well recognized.

With conventional inactivated virus IAV-S vaccines the choice of viral strains is based on HA antigen properties. IAV-S vaccines that induce HA inhibiting (HI) antibody titers protect pigs against experimental infection with an antigenically similar strain [Kyriakis et al., *Vet Microbiol* 144(1-2):67-74 (2010)]. However, relatively rapid genetic drift of the HA genes allows new strains to emerge that are not functionally inhibited by the vaccine-induced HA antibodies.

As a consequence, commercially available vaccines often do not protect against new and emerging virus subtypes/clusters, and offer only limited protection against heterosubtypic challenge, since the antigens do not match all contemporary strains circulating in the field [Lee et al., *Can J Vet Res* 71(3): 207-12(2007); Vincent et al., *Vaccine* 28(15): 2782-2787 (2010)]. Thus, such vaccines must be periodically updated to match currently circulating strains.

Therefore, there is a need in the art to develop novel IAV-S vaccines that are safe, effective, and can be rapidly altered to antigenically match an emerging strain.

Because most viruses, such as influenza viruses, are relatively simple structures, the use of a single antigen from their antigen profile can sometimes suffice to generate a protective immune response. Such a subunit vaccine can be manufactured by extraction from the virus or its culture, or by the recombinant expression of the specific antigen. Alternatively, the viral antigen can be delivered to a target animal and expressed inside it, by a live recombinant carrier micro-organism that acts as a vector. Vectors can be live attenuated or non-live. A number of vector-based strategies have been employed through the years for vaccines in an effort to protect against certain pathogens.

A variation on the use of viral vector vaccines is the use of vaccines based on replicon particles [RP; see Lundstrom, 2014, Vaccines, vol. 6, p. 2392-2415]. These are virus-like particles but comprise a defective viral genome and typically, a heterologous gene. These replicon particles typically comprise RNA packaged in particles (i.e., they are encapsidated) such that they are able to enter a target animal host cell and perform one round of viral genome amplification without the ability to form new particles. The replicon particle does not propagate from the infected cell, as it lacks the necessary structural protein-coding sequence(s). As such, they are more similar to wild-type virus (e.g. in terms of tropism) than other replicon vaccines such as naked RNA vaccines, or vaccines comprising RNA launched from a DNA plasmid.

The genome of the RP's typically expresses a heterologous gene encoding an immunoprotective antigen. Most widely used and most extensively studied are alphavirus RNA replicon particles [Vander Veen et al., 2012, Anim. Health. Res. Rev., vol. 13, p. 1-9; and: Kamrud et al., 2010, J. Gen. Virol., vol. 91, p. 1723-1727], which are therefore preferred for practical reasons, and which have been developed from viral genomes by replacing the structural protein genes with heterologous genes. The resulting RNAs, called replicons, are capable of directing their own replication and express high levels of the heterologous gene when they are introduced into the cytoplasm of host cells. Since these replicons lack the alphavirus structural protein genes, they are incapable of forming virions and spreading to adjacent cells. However, replicons can be efficiently packaged into virus replicon particles (RPs) by introducing them into cells where the structural proteins are provided in trans [Pushko et al., 1997, Virology, vol. 239, p. 389-401].

Also, alphavirus RP's are believed to be somewhat stronger immunopotentiators than other RP's known in the art and based on other viruses such as the bunyavirus. Several Alphavirus species have been used to develop RP vaccines, e.g.: Venezuelan equine encephalitis virus (VEEV) [Pushko et al., 1997, Virology, vol. 239, p. 389-401], Sindbis virus [Bredenbeek et al., 1993, J. of Virol., vol. 67, p. 6439-6446], and Semliki Forest virus [Liljestrom & Garoff, 1991, Biotechnology (NY), vol. 9, p. 1356-1361].

RP vaccines can elicit mucosal and systemic immune responses following immunization of a target animal [Davis et al., 2002, IUBMB Life, vol. 53, p. 209-211]. VEE based RP vaccines are also the basis of several USDA-licensed vaccines, which include: Porcine Epidemic Diarrhea Vaccine, RNA (Product Code 19U5.P1), Swine Influenza Vaccine, RNA (Product Code 19A5.D0), Avian Influenza Vaccine, RNA (Product Code 1905.D0), and Prescription Product, RNA Particle (Product Code 9PP0.00).

Since the RP vector system can be easily manipulated at a molecular level, vaccines can be produced quickly in order to respond to emerging virus subtypes.

Thus, there is an ongoing demand for novel vaccines, which provide for a broad protection against circulating IAV-S strains, in particular for providing broad protection against most or all of the four main IAV-S strains circulating in Europe of EurAsianAvian H1N1, Gent84 H3N2, Scot/94 H1N2 and pandemic2009 H1N1, and which can be rapidly adapted to respond to emerging virus subtypes and antigenic drift.

However, the RP vector system, such as the alphavirus replicon platform, does not allow for the insertion of any desired number of antigens, such as the insertion of all NA and HA genes of the four main circulating IAV-S strains into the replicon vector, in order to achieve broadest protection. Alphavirus vector platforms are typically a three-component system composed of an RNA containing the nonstructural genes with their associated packaging signal and the structural proteins removed and replaced with heterologous gene sequences. Two helper RNAs contains the virus structural proteins without the packaging signal. These three-component, replicon, based systems are limited in the amount of RNA they can package by the volume of the virus capsid [Vanda K. et al., Vol. 390(2), 2009, 368-373]. This intrinsic limitation of the RP vector system makes it difficult to meet the ongoing demand of providing a vaccine having broad protection against most or all circulating IAV-S strains.

SUMMARY OF THE INVENTION

In a first aspect of the present invention, it has surprisingly been found that in case of inserting more than one swine influenza A virus hemagglutinin (IAV-S HA) antigen, the position of the genes encoding the HA antigens within the viral genome of an RNA replicon particle greatly impacts the level of induced immunity.

Accordingly, the present invention provides nucleic acid constructs that encode a combination of two IAV-S HA antigens from different lineages in a specific order. These nucleic acid constructs can be used in RNA replicon particles. These RNA replicon particles of the present invention may be used in immunogenic compositions for providing vaccines for use in the prevention of a disease caused by a Swine influenza A virus (IAV-S) in a vaccinated subject (e.g. a human, companion animal or livestock, particularly swine).

In a first embodiment of the present invention, the nucleic acid construct comprises a combination of the IAV-S HA antigen of the Scot/94 lineage and the Eurasian avian-like (EA) lineage, with the IAV-S HA of the Scot/94 lineage placed first (in the order from 5' to 3' of the nucleic acid sequence) and the IAV-S HA of the EA lineage placed second. The term "in 5' to 3' direction", also known as: 'in downstream direction', is well-known in the field. Together with the terms "in this order" it serves to indicate the relative orientation which the elements that are summed up thereafter need to have in respect of each other, in order to be functional with the gene-expression machinery of a host cell, i.e. in which a RP according to the invention comprising the nucleic acid construct can be replicated and expressed. As the skilled person will realise, in the present case, this direction relates to the nucleic acid strand of a genome that is the 'coding strand'. The genes may be present in a consecutive order in the 5' to 3' direction, i.e. there are no intermediate genes for expression into proteins present in the construct. In that case the nucleic acid construct typically comprises, in the order from 5' to 3', the backbone virus nonstructural protein open reading frame, a subgenomic promoter followed by the first HA antigen gene sequence, interstitial sequence, a second subgenomic promoter sequence followed by a second HA antigen gene, and finally the backbone virus 3' untranslated region.

Thus, the present invention provides a nucleic acid construct comprising, in the order from 5' to 3' of the nucleic acid sequence:

- a first nucleic acid sequence encoding a first hemagglutinin (HA) antigen of IAV-S of the A/swine/Scotland/410440/1994-like $H1_{hu}N2$ (Scot/94) lineage, and
- a second nucleic acid sequence encoding a second HA antigen of IAV-S of the Eurasian avian-like $H1_{av}N1$ (EA) lineage In a second embodiment of the present invention, the nucleic acid construct comprises a combination of the IAV-S HA antigen of the Gent/84 lineage and the pdm09 lineage, with the IAV-S HA of the Gent/84 lineage placed first (in the order from 5' to 3' of the nucleic acid sequence) and the IAV-S HA of the pdm09 lineage placed second. Thus, the present invention provides a nucleic acid construct comprising, in the order from 5' to 3' of the nucleic acid sequence:

- a first nucleic acid sequence encoding a first HA antigen of IAV-S of the A/swine/Gent/1/1984-like H3N2 (Gent/84) lineage, and
- a second nucleic acid sequence encoding a second HA antigen of IAV-S of the A(H1N1)pdm09 (pdm09) lineage.

In a second aspect of the present invention, it has surprisingly been found that the swine influenza A virus hemagglutinin (IAV-S HA) of certain strains of the four major circulating IAV-S lineages can provide for improved immunity against IAV-S compared to other strains. In particular, it has been found that specific combinations of IAV-S HA can provide for improved immunity. Thus, such combinations of IAV-S HA can beneficially be used in nucleic acid constructs, which can be included in RNA replicon particles. These RNA replicon particles can be used as immunogenic compositions for providing vaccines that aid in the protection of the vaccinated subject (e.g. a human, companion animal or livestock, particularly swine) against IAV-S, e.g. aid in the prevention of IAV-S virus infection.

Thus, the present invention further provides nucleic acid constructs that encode a combination of two IAV-S HA antigens of specific strains as defined herein.

In a first embodiment, the present invention provides a nucleic acid construct comprising first and second nucleic acid sequences:

- a first nucleic acid sequence encoding a first HA antigen of IAV-S of the A/swine/Scotland/410440/1994-like $H1_{hu}N2$ (Scot/94) lineage from strain A/swine/Italy/3033-1/2015 (H1N2), and
- a second nucleic acid sequence encoding a second HA antigen of IAV-S of the Eurasian avian-like $H1_{av}N1$ (EA) lineage from strain A/swine/Italy/28762-3/2013 (H1N1).

In a second embodiment, the present invention provides a nucleic acid construct for use in the prevention or treatment of a disease caused by a Swine influenza A virus in a subject, the nucleic acid construct comprising first and second nucleic acid sequences:

- the first nucleic acid sequence encoding a first hemagglutinin (HA) antigen of a Swine influenza A virus (IAV-S) of the A/swine/Gent/1/1984-like H3N2 (Gent/84) lineage from strain A/swine/Italy/240849/2015 (H3N2), and
- a second nucleic acid sequence encoding a second HA antigen of IAV-S of the A(H1N1)pdm09 (pdm09) lineage from strain A/swine/England/373/2010 (H1N1).

In another important embodiment, there is provided an RNA replicon particle comprising the nucleic acid construct of the present invention. Thus, the RNA replicon particle may comprise the nucleic acid construct according to the first or according to the second embodiment.

Encompassed by the present invention are any combinations of the embodiments of the first and second aspects as described herein. Thus, the present invention further provides nucleic acid constructs in which the IAV-S HA antigens are arranged in the specific order as defined in the first aspect and in which the IAV-S antigens are from the specific strains as defined in the second aspect.

In another important aspect, the present invention provides an RNA replicon particle comprising the nucleic acid constructs as described herein.

In another important aspect, the present invention provides an immunogenic composition, comprising the RNA replicon particle as described herein.

In another important aspect, the present invention provides an immunogenic composition comprising a combination of RNA replicon particles, the combination comprising a first RNA replicon particle comprising the nucleic acid construct according to the first embodiment and a second RNA replicon particle comprising the nucleic acid construct according to the second embodiment.

A further embodiment of the present invention relates to a vaccine comprising the immunogenic composition as described herein.

In another important embodiment, the vaccine of the present invention may be used in the prevention or treatment of a disease caused by a Swine influenza A virus in a subject.

In another important embodiment, the present invention provides a method of immunizing a porcine against a swine influenza A virus, the method comprising administering to the porcine an immunologically effective amount of the vaccine of the present invention.

In a third aspect, it has surprisingly been found that a combination of two RNA replicon particles each comprising a nucleic acid construct encoding first and second HA antigens of IAV-S of different lineages can provide for improved immunity against IAV-S.

Thus, the present invention further provides an immunogenic composition comprising first and second RNA replicon particles, the first RNA replicon particle comprising a nucleic acid construct, comprising first and second nucleic acid sequences encoding first and second HA antigens of IAV-S, wherein the first HA antigen is a of the A/swine/Gent/1/1984-like H3N2 (Gent/84) lineage, and the second HA antigen is of the A(H1N1)pdm09 (pdm09) lineage, the second RNA replicon particle comprising a nucleic acid construct comprising third and fourth nucleic acid sequences encoding third and fourth HA antigens of IAV-S, wherein the third HA antigen is of the A/swine/Scotland/410440/1994-like $H1_{hu}N2$ (Scot/94) lineage, and the fourth HA antigen is of the Eurasian avian-like $H1_{av}N1$ (EA) lineage.

Encompassed by the present invention are any combinations of the embodiments of the third aspect with the embodiments of the first and second aspects as described herein. Thus, the present invention further provides replicon particles as described in the third aspect, wherein the nucleic acid constructs encode IAV-S HA antigens, which are arranged in the specific order as defined in the first aspect and/or in which the IAV-S antigens are from the specific strains as defined in the second aspect.

In a fourth aspect, it has surprisingly been found that a nucleic acid construct comprising a specific combination of IAV-S neuraminidase (NA) antigens of three different lineages as described herein can be used for providing immunity against all four major circulating IAV-S lineages.

Thus, the present invention further provides a nucleic acid construct comprising first, second and third nucleic acid sequences encoding first, second and third NA antigens of IAV-S, wherein the first NA antigen is of the A/swine/Scotland/410440/1994-like $H1_{hu}N2$ (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}N1$ (EA) lineage.

In another important embodiment, the present invention provides an RNA replicon particle comprising the nucleic acid construct as described in the fourth aspect.

In another important embodiment, the present invention provides an immunogenic composition, comprising the RNA replicon particle as described in the fourth aspect.

A further embodiment of the present invention relates to a vaccine comprising the immunogenic composition as described in the fourth aspect.

In another important embodiment, the vaccine as described in the fourth aspect may be used in the prevention or treatment of a disease caused by a Swine influenza A virus in a subject.

In another important embodiment, the present invention provides a method of immunizing a porcine against a swine influenza A virus, the method comprising administering to the porcine an immunologically effective amount of the vaccine as described in the fourth aspect.

In another important aspect, the present invention provides an immunogenic composition comprising a combination of RNA replicon particles, the combination comprising first and second RNA replicon particles according to the third aspect, and a third RNA replicon particle comprising the nucleic acid construct according to the fourth aspect.

Encompassed by the present invention are any combinations of the embodiments of the fourth aspect with the embodiments of the first, second and/or third aspects as described herein. Thus, the present invention further provides replicon particles as described in the third aspect, wherein the nucleic acid constructs encode IAV-S HA antigens, which are arranged in the specific order as defined in the first aspect and/or in which the IAV-S antigens are from the specific strains as defined in the second aspect in combination with replicon particles as described in the fourth aspect.

BRIEF 10

FIG. 1: Hemagglutination inhibition (HI) antibody titers induced by single-gene RNA particle encoding one HA antigen of EurAsianAvian lineage IAV-S.

Figure 2:
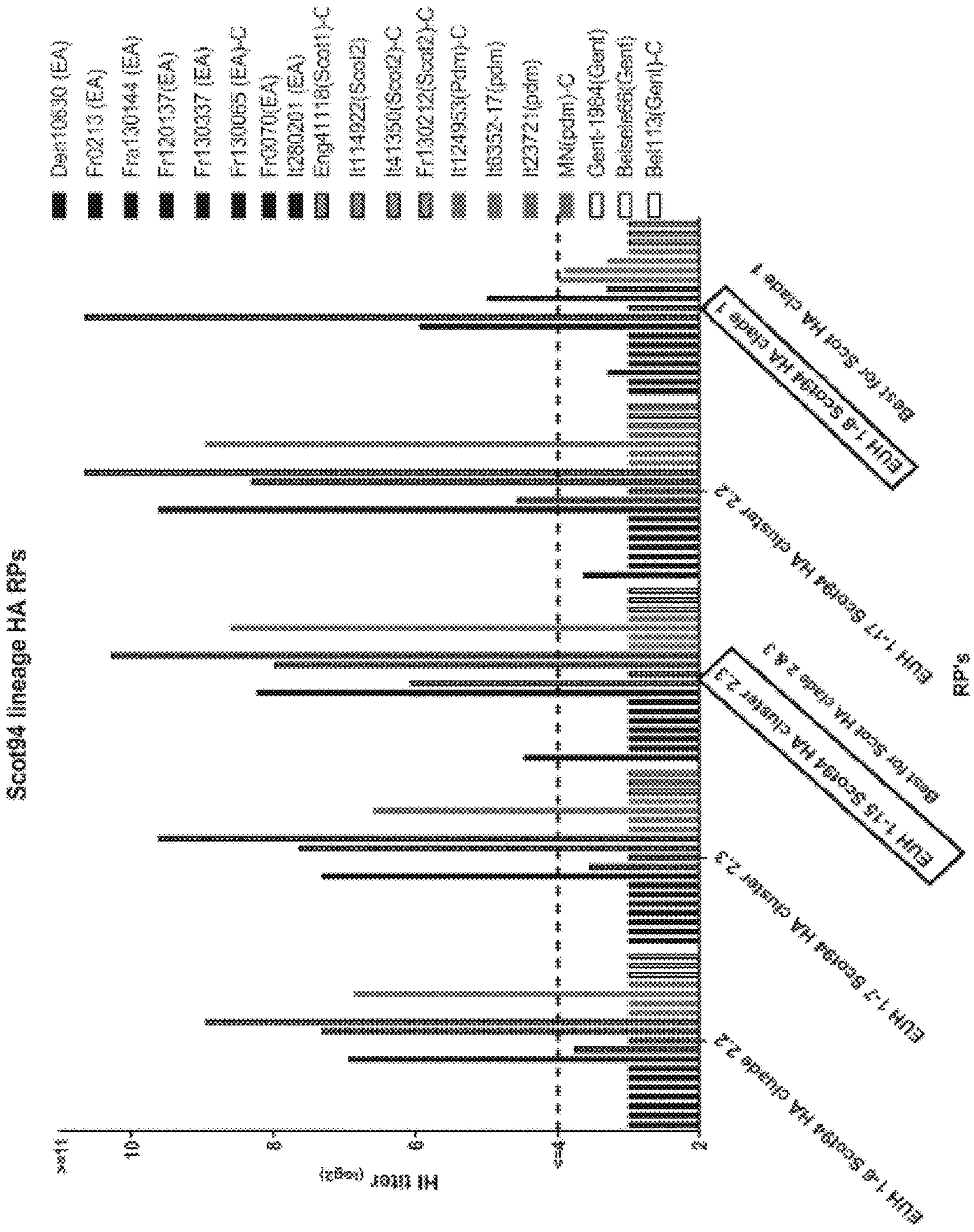

FIG. 2: HI antibody titers induced by single-gene RNA particle encoding one HA antigen of Scot 1994 lineage IAV-S.

Figure 3:
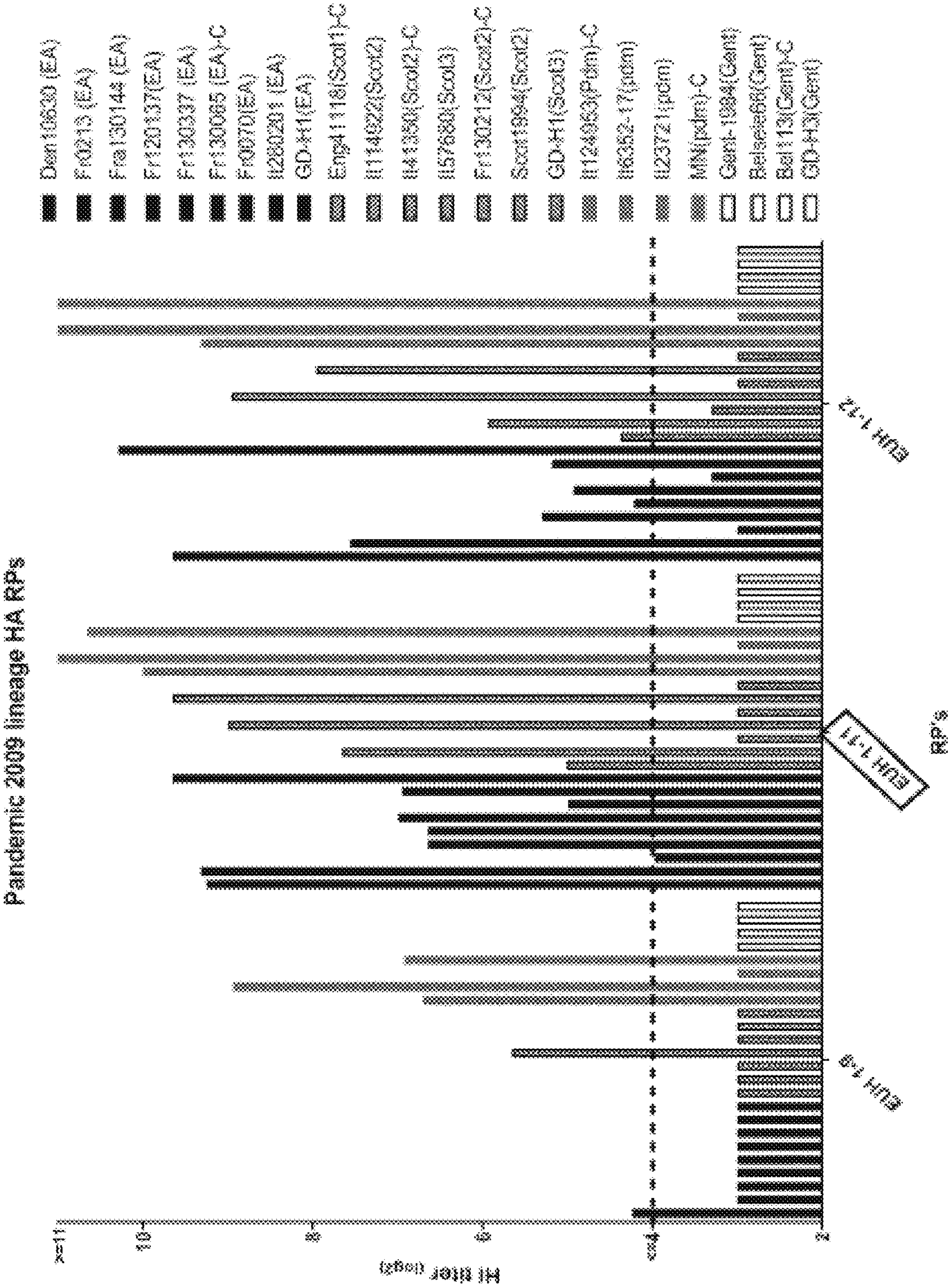

FIG. 3: HI antibody titers induced by single-gene RNA particle encoding one HA antigen of Pdm 2009 lineage IAV-S.

Figure 4:
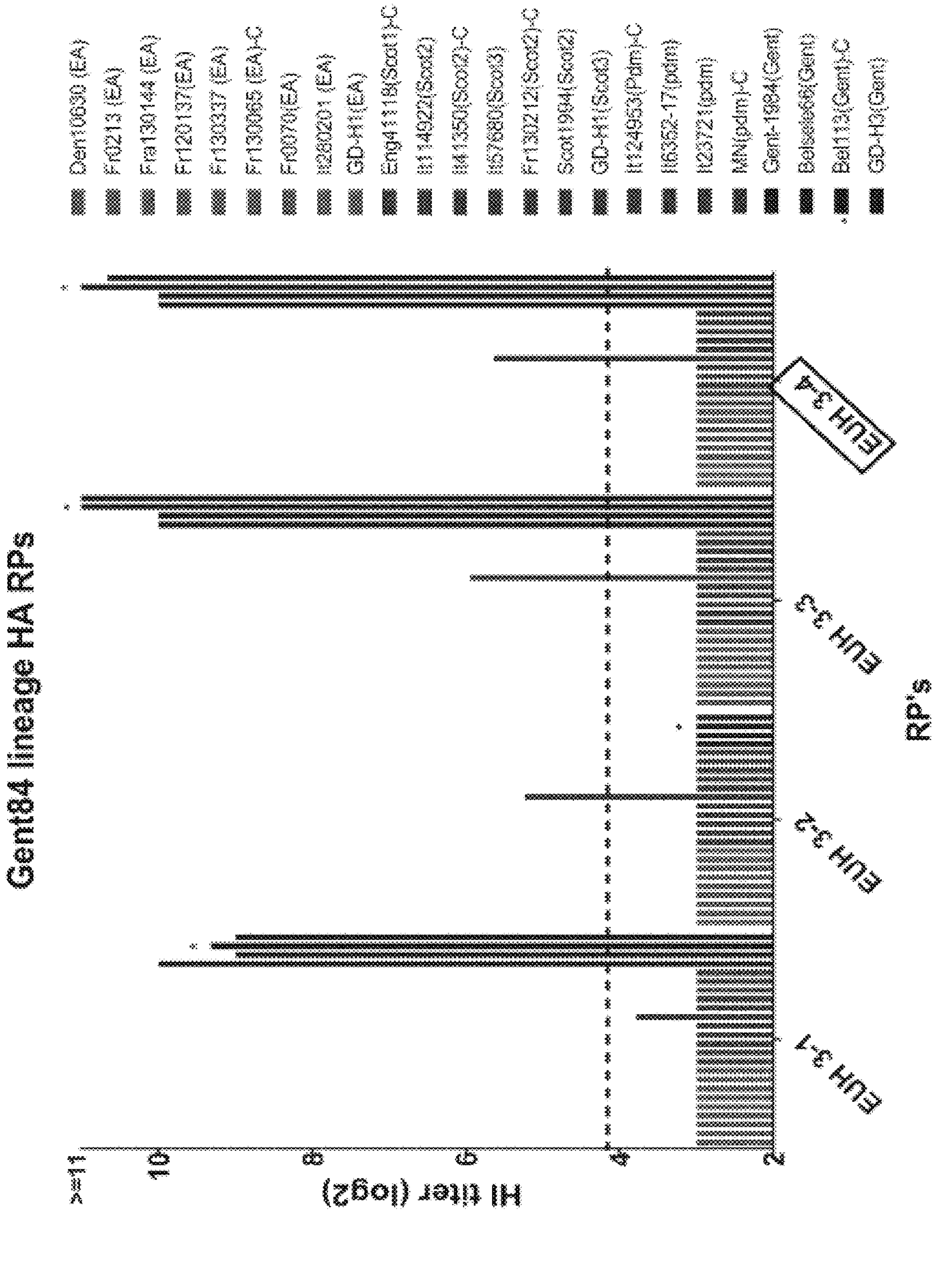

FIG. 4: HI antibody titers induced by single-gene RNA particle encoding one HA antigen of Gent 1984 lineage IAV-S.

Figure 5:
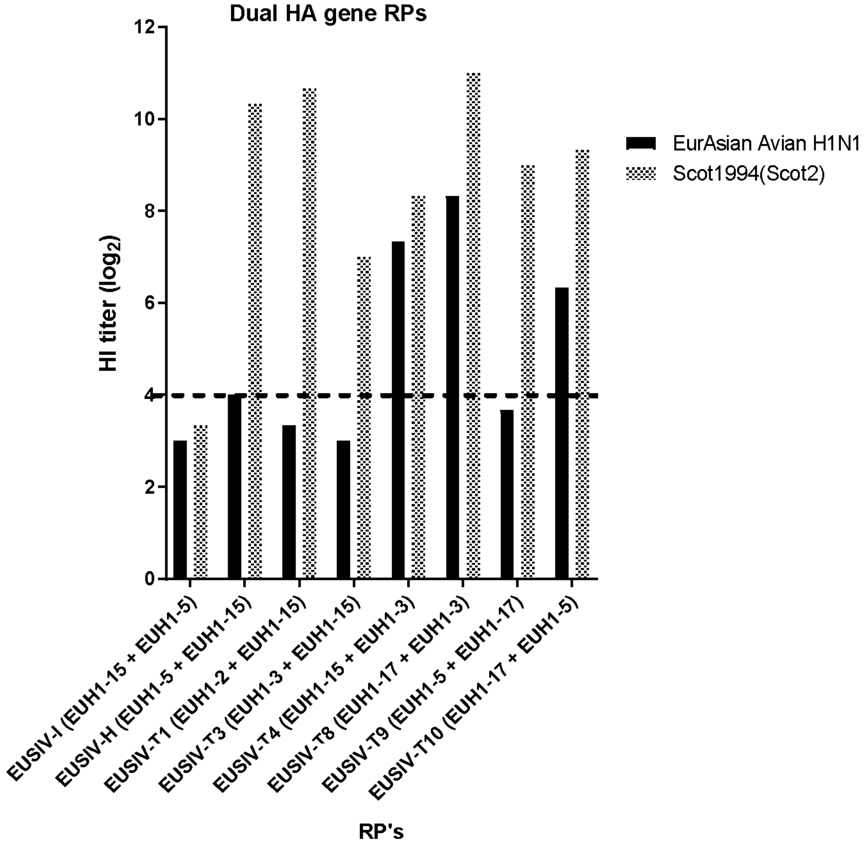

FIG. 5: HI antibody titers induced by dual-gene RNA particle encoding one HA antigen of EurAsianAvian (EUHA1-2, EUHA1-3 & EUHA1-5) and another of Scot1994 (EUHA1-15 or EUHA1-17) lineage IAV-S strains in different combinations.

Figure 6:
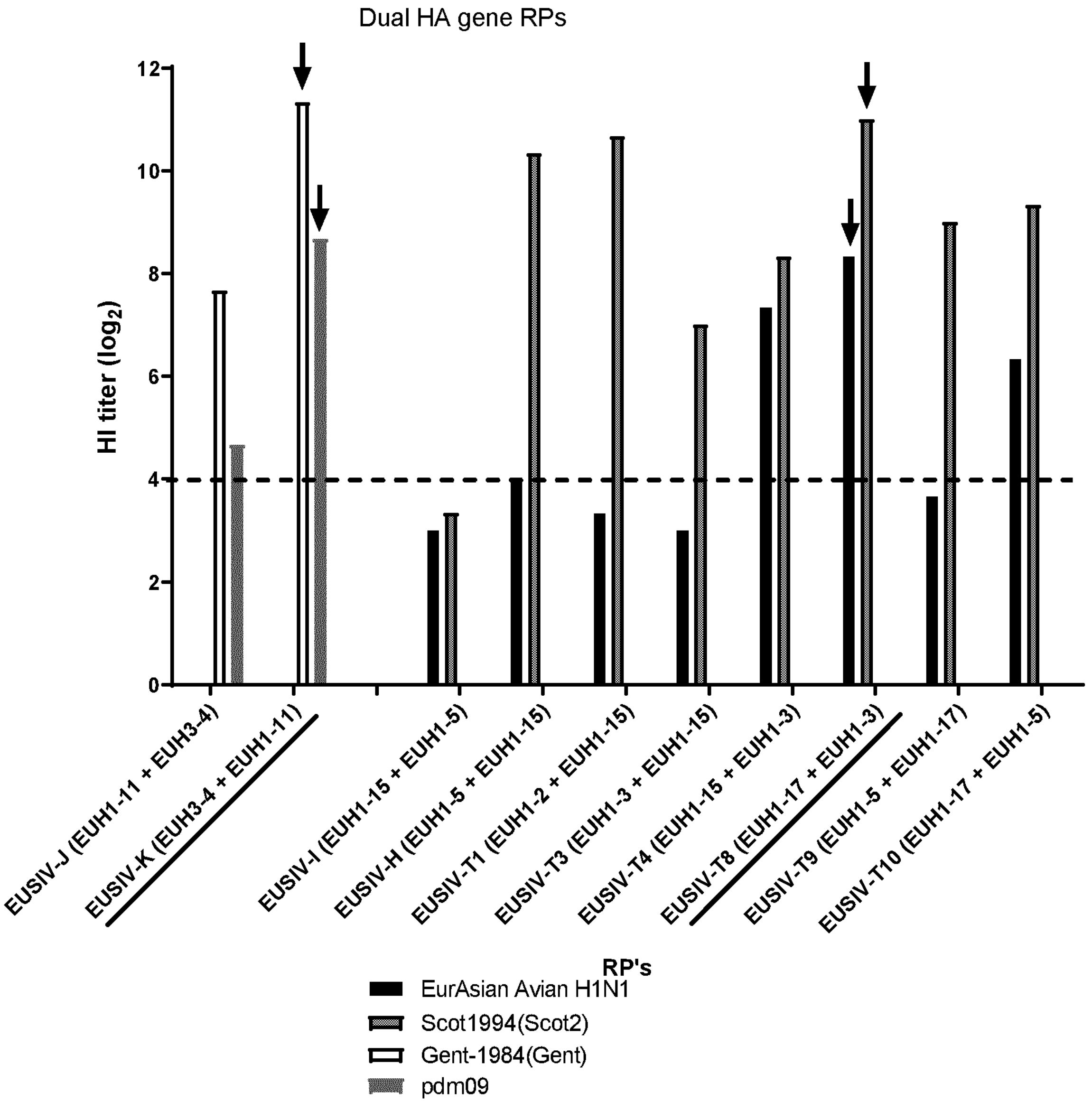

FIG. 6: HI antibody titers induced by dual-gene RNA particle encoding one HA antigen of pandemic (EUHA1-11) and another of Gent1984 (EUHA3-4) or one HA antigen of Scot1994 (EUH1-15, EUHA1-17) and another of EurAsianAvian (EUHA1-3 & EUHA1-5) lineage IAS strains in two different positions.

Figure 7:
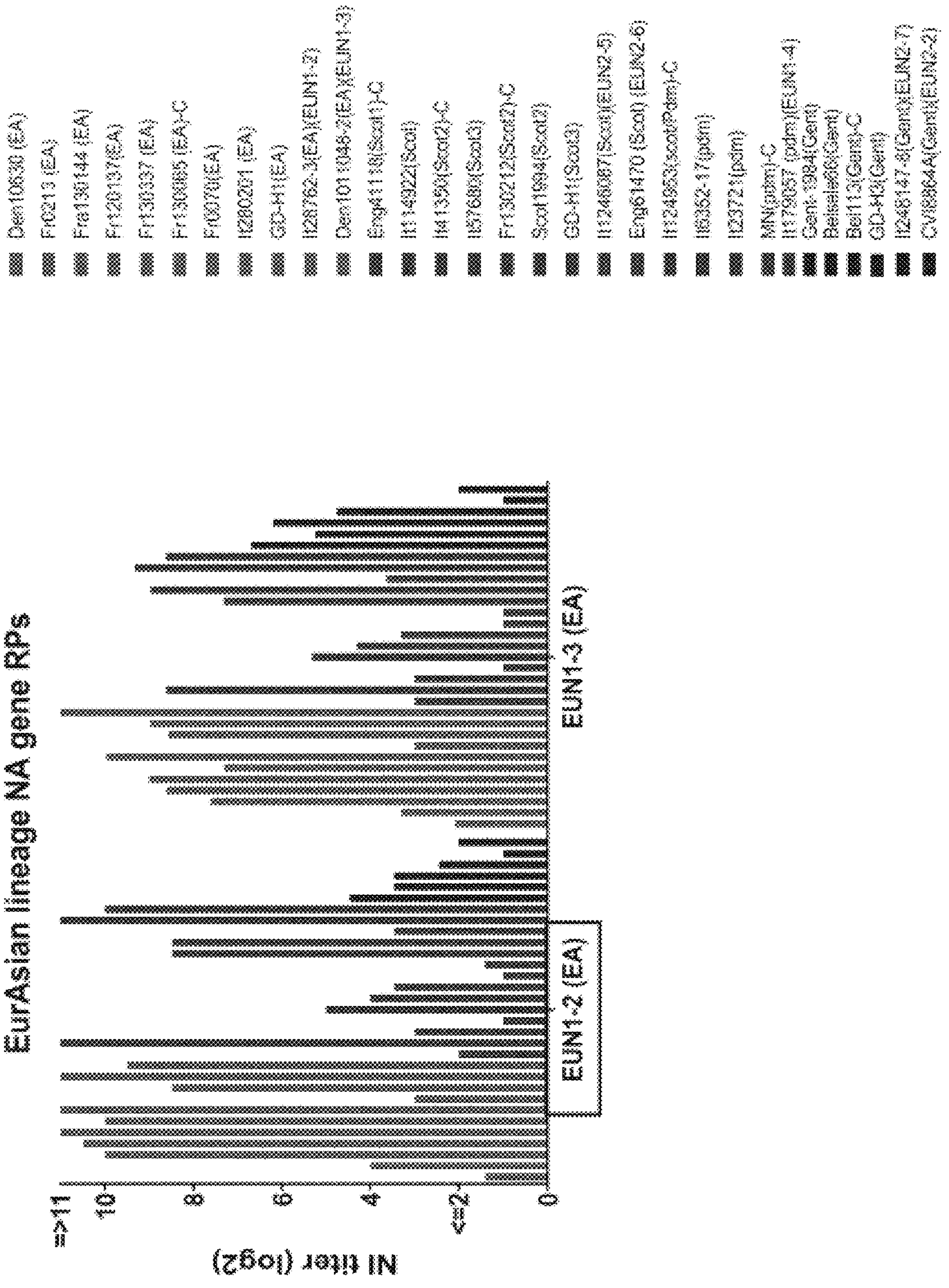

FIG. 7: Neuraminidase inhibition (NI) antibody titers induced by single-gene RNA particle encoding one NA antigen of EurAsianAvian (EA) lineage IAV-S.

Figure 8:
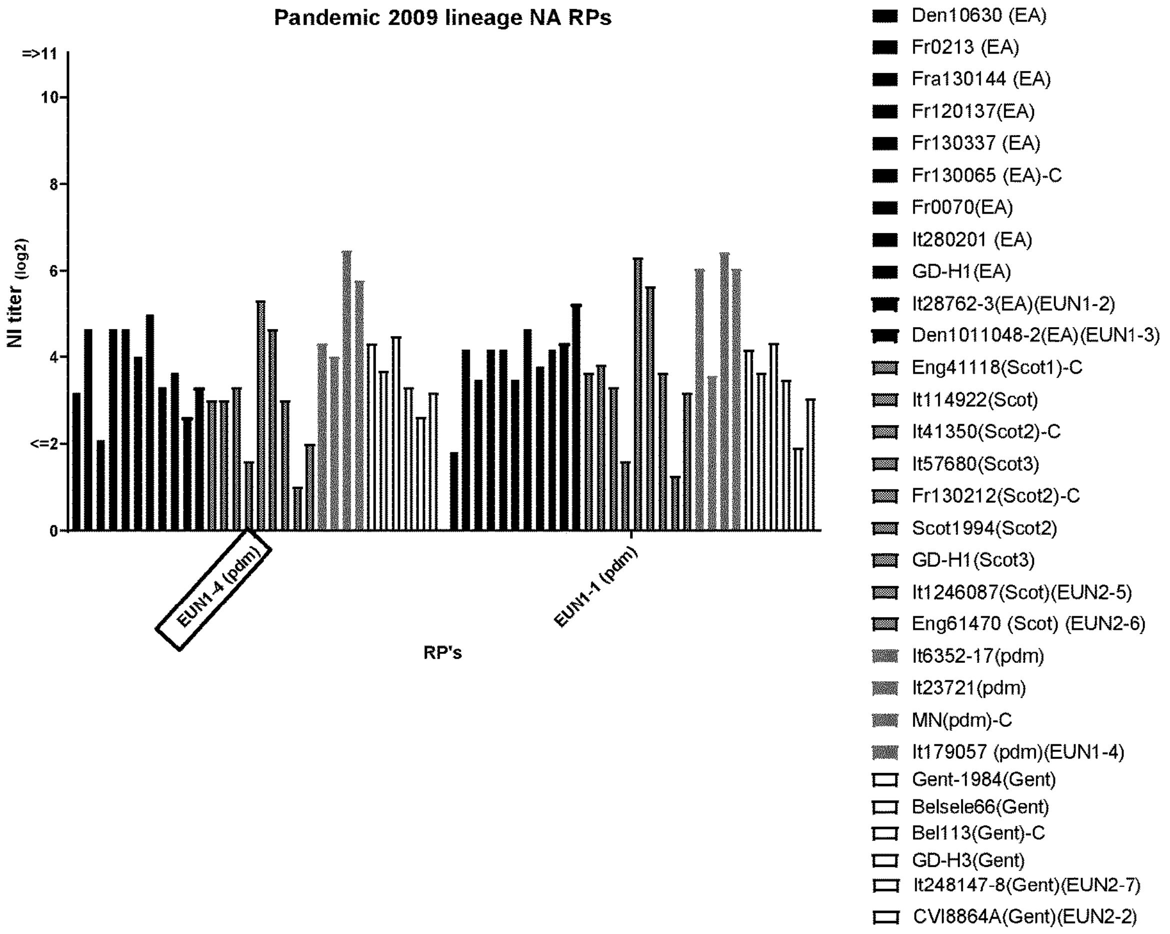

FIG. 8: (NI) antibody titers induced by single-gene RNA particle encoding one NA antigen of Pdm09 lineage IAV-S.

Figure 9:
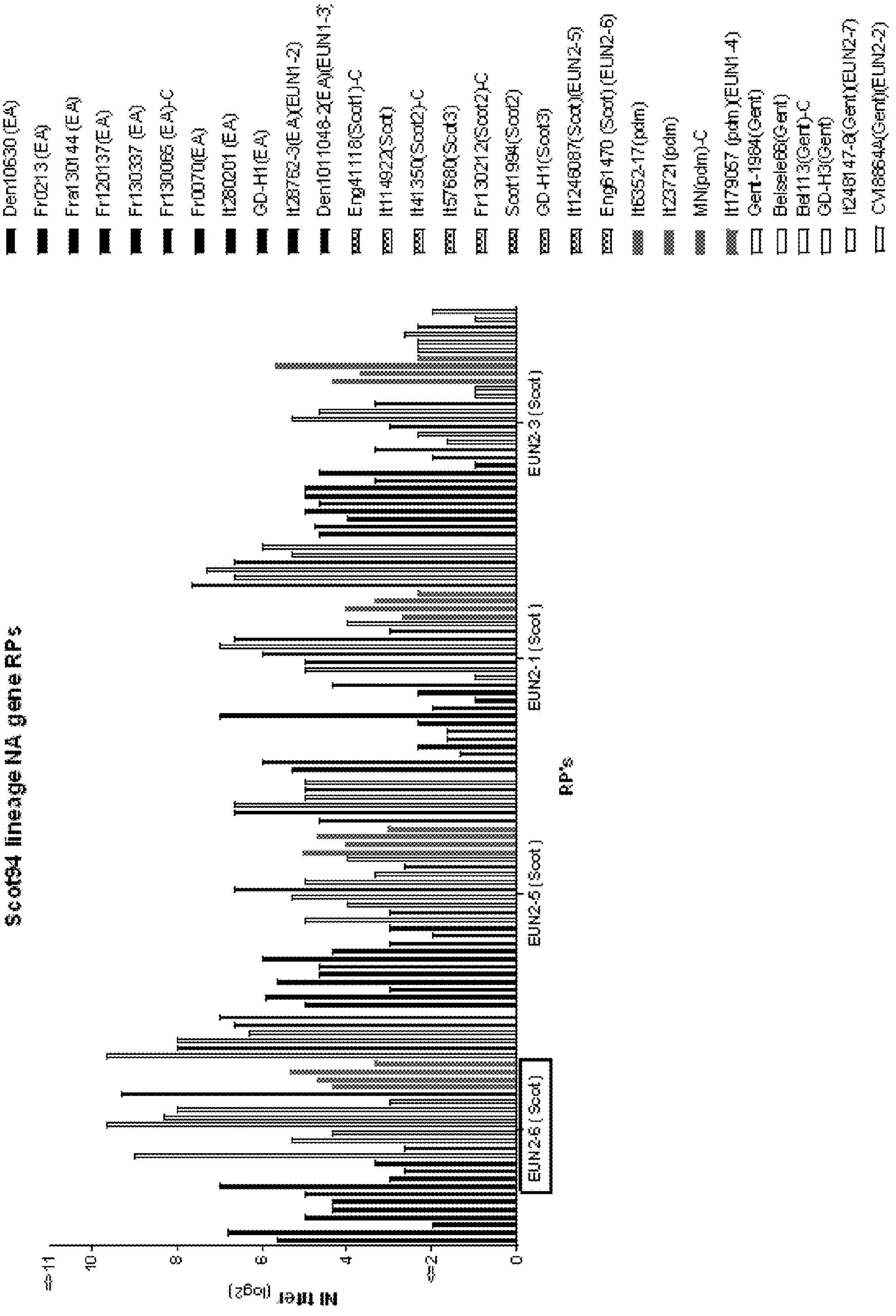

FIG. 9: (NI) antibody titers induced by single-gene RNA particle encoding one NA antigen of Scot/94 lineage IAV-S.

Figure 10:
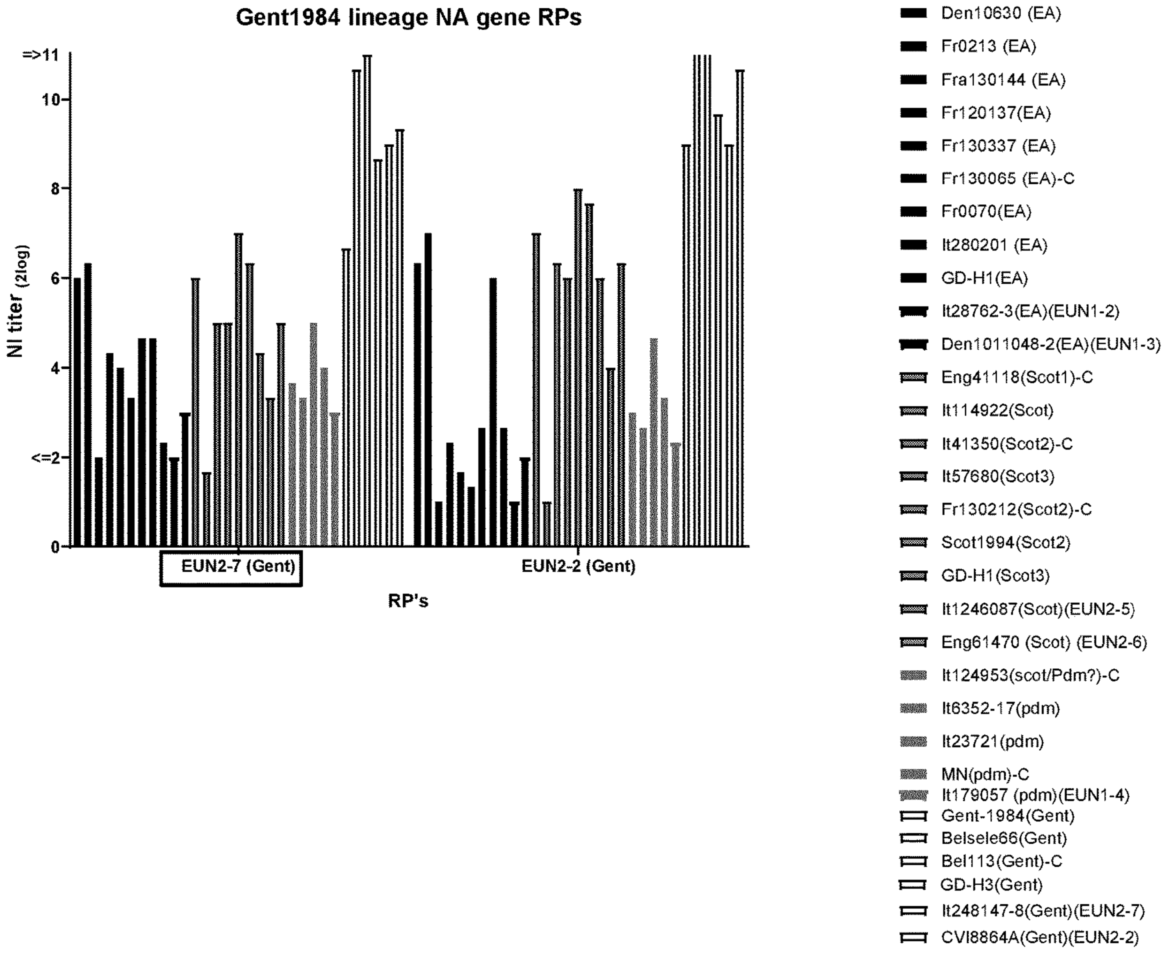

FIG. 10: (NI) antibody titers induced by single-gene RNA particle encoding one NA antigen of Gent/84 lineage IAV-S.

Figure 11:
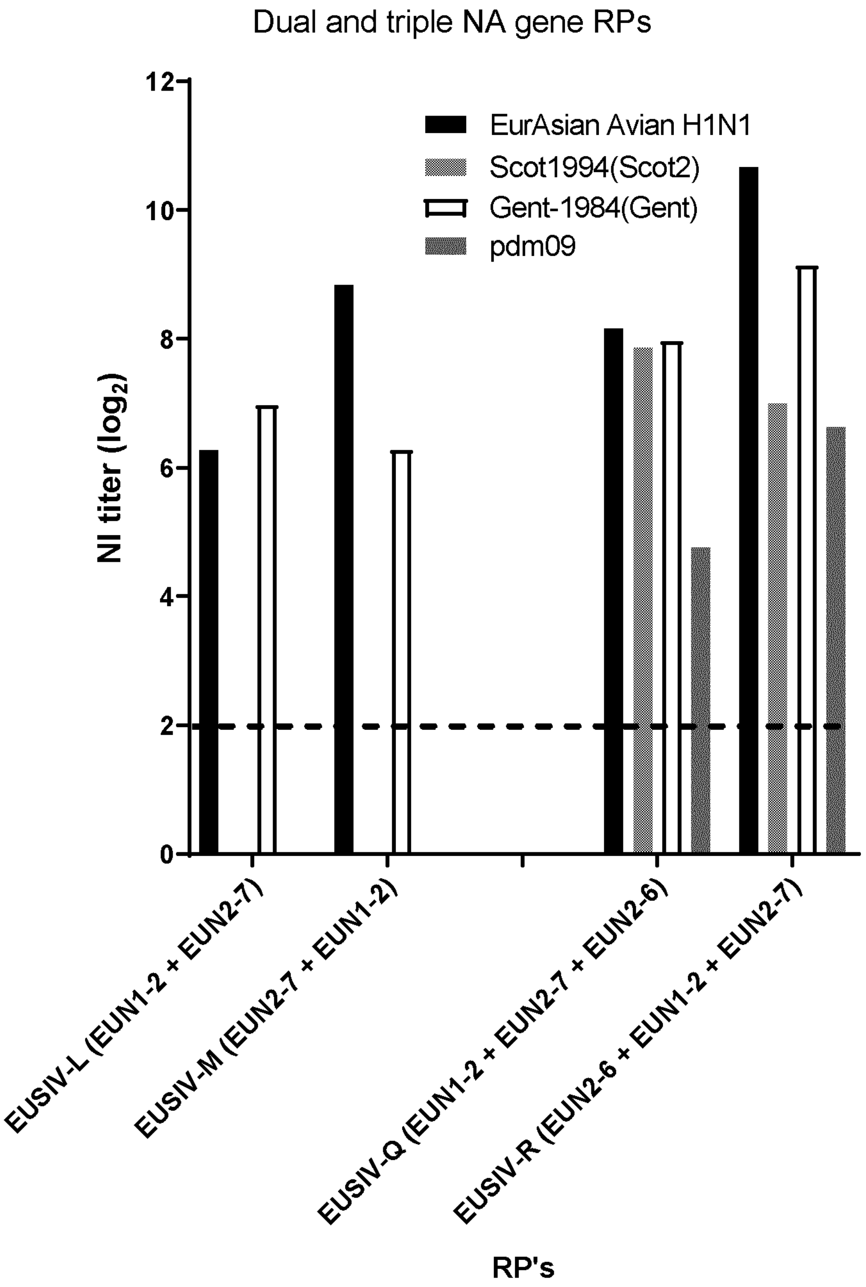

FIG. 11: NI antibody titers induced by dual-gene RNA particles encoding one NA antigen of EurAsianAvian (EUNA1-2) and another NA of Gent1984 (EUNA2-7) or triple-gene RNA particles encoding one NA antigen each of EurAsianAvian (EUNA1-2), Gent1984 (EUNA2-7) and Scot1994 (EUHNA2-6) lineage IAS strains in different positions.

Figure 12:
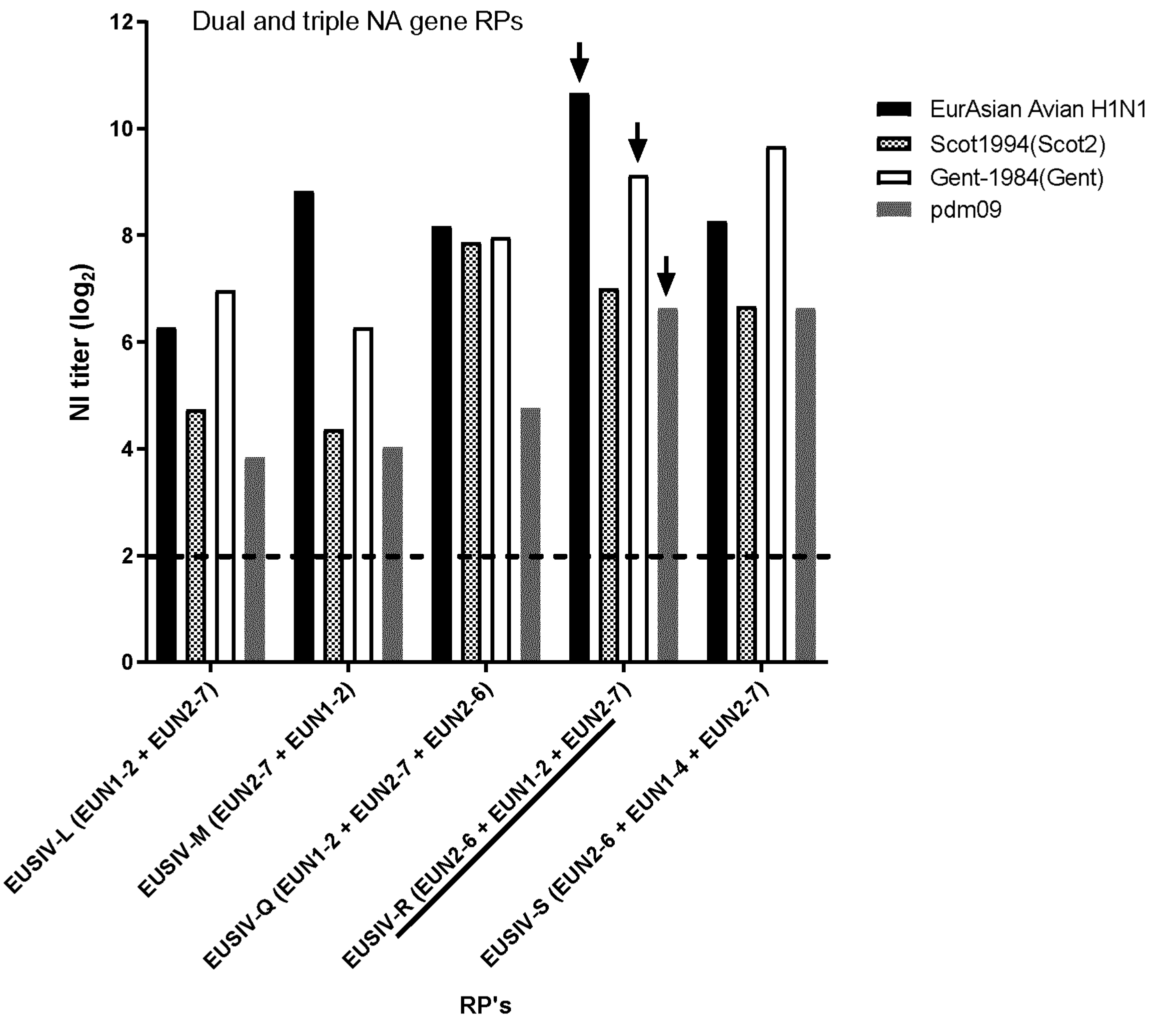

FIG. 12: NI antibody titers induced by dual-gene RNA particles encoding one NA antigen of EurAsianAvian (EUNA1-2) and another NA of Gent1984 (EUNA2-7) or triple-gene RNA particles encoding one NA antigen each of EurAsianAvian (EUNA1-2), Gent1984 (EUNA2-7) and Scot1994 (EUHNA2-6) or Pdm09 (EUNA1-4) lineage IAV-S strains in different positions.

Figure 13A:
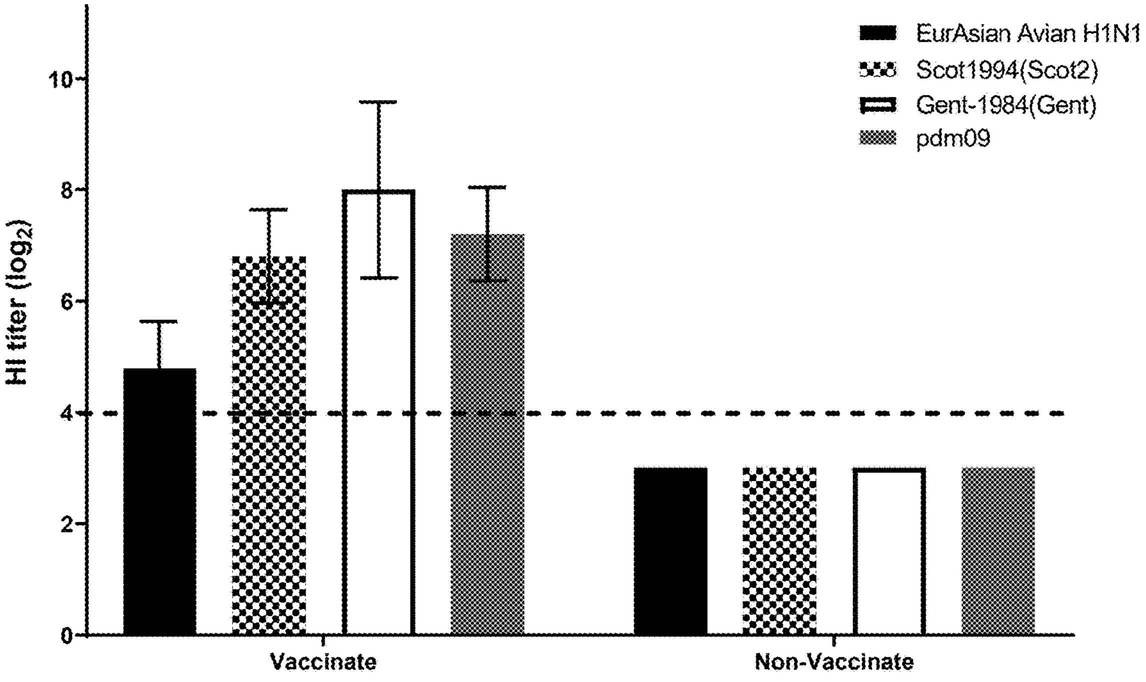
Figure 13B:
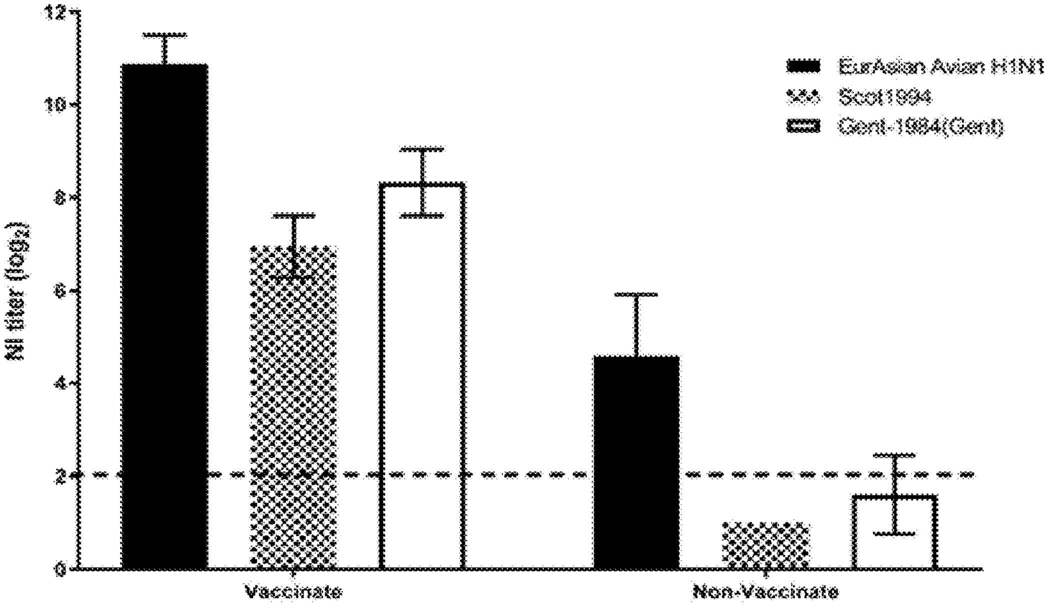
Figure 13C:
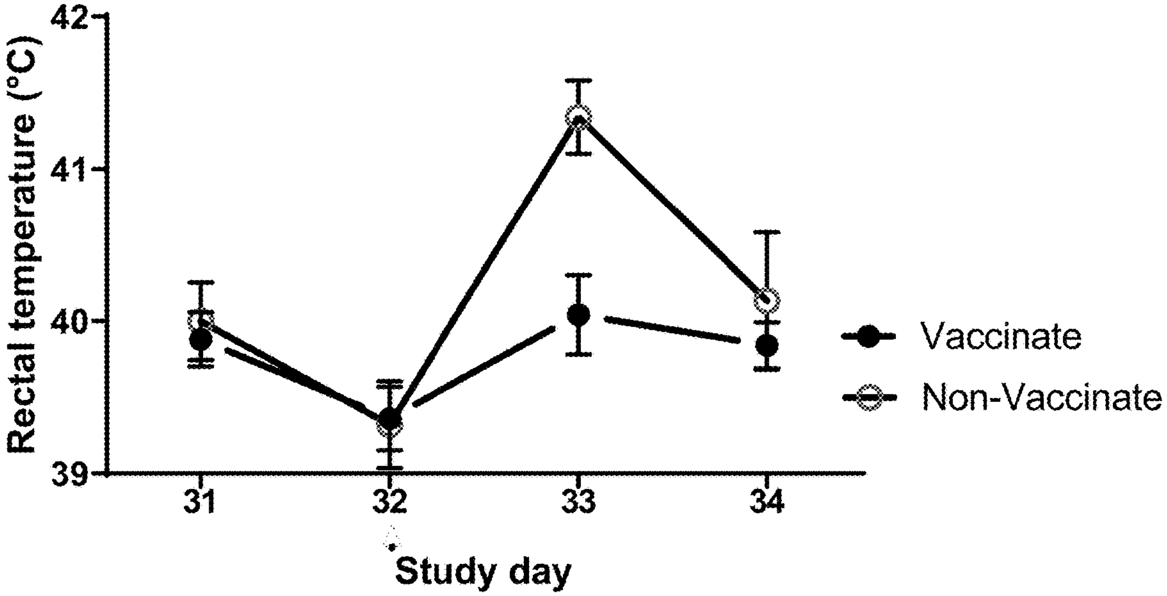

FIGS. 13A-13D show results of evaluation of vaccine efficacy of a multivalent IAV-S vaccine, as described in Example 6. FIG. 13A: Induction of functional HI titers against heterologous IAV-S strains belonging to all four lineages; FIG. 13B: Induction of NI titers against homologous NA antigen of all three lineages; FIG. 13C: Rectal temperatures in pigs after experimental infection; and FIG. 13D: Lung lesions induced in pigs after experimental infection.

Figure 14A:
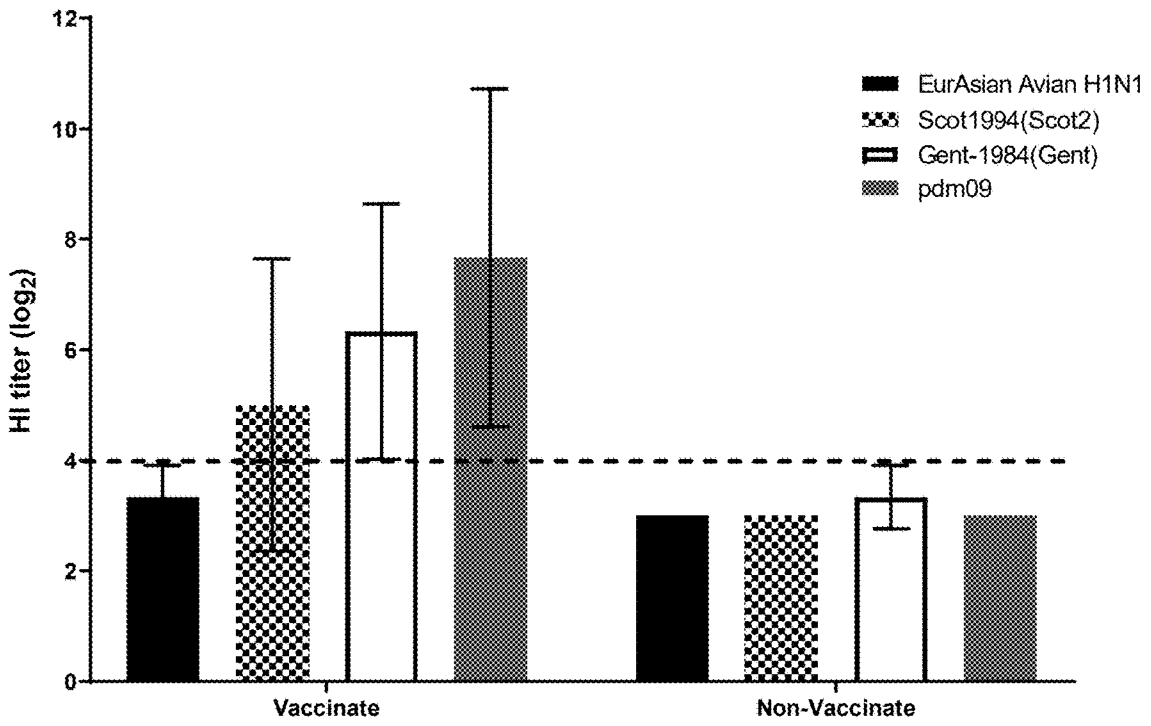
Figure 14B:
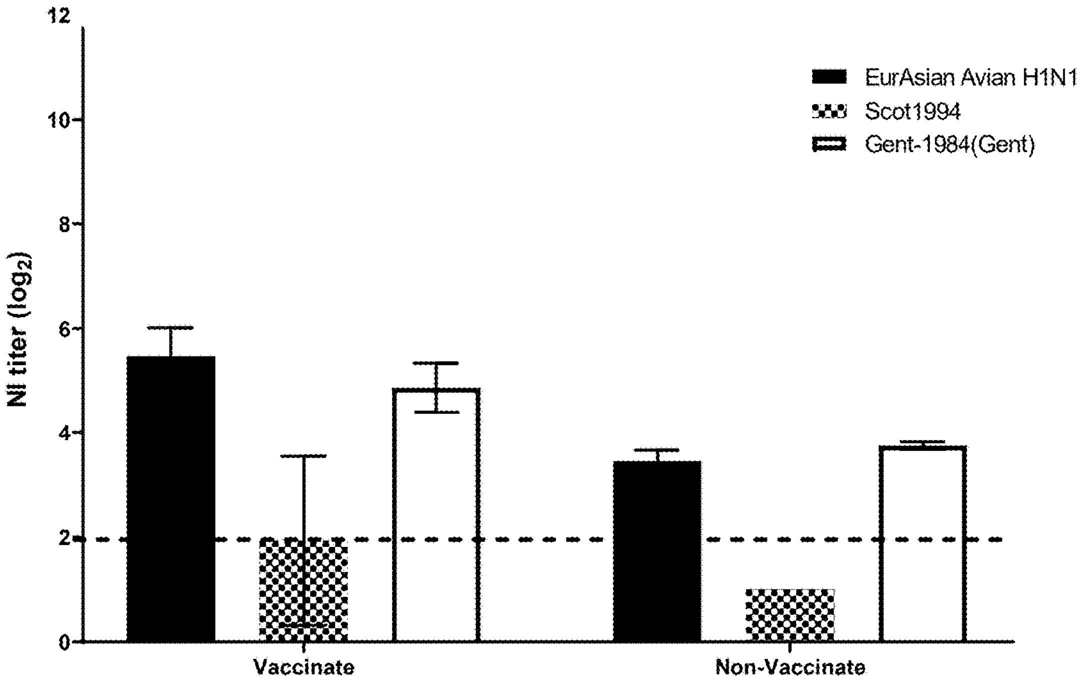

FIGS. 14A-14B: Results of evaluation of vaccine efficacy after intradermal administration of a multivalent IAV-S vaccine, as described in Example 7. FIG. 14A: Induction of functional HI titers against heterologous IAV-S strains belonging to three out of four lineages tested. Induction of NI titers against two out of three homologous NA antigens tested.

DEFINITION OF TERMS

In order to fully appreciate the invention, the following definitions are provided.

A nucleic acid construct is an artificially constructed segment of nucleic acid (e.g. DNA, RNA, mRNA), typically for transplantation into a target cell.

The use of singular terms for convenience in description is in no way intended to be limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1\times10^8$ alphavirus RNA replicon particles per milliliter contains from $5\times10^7$ to $1.5\times10^8$ alphavirus RNA replicon particles per milliliter.

As used herein, the term "pig" or "swine" or "porcine" are used interchangeably and include all domesticated porcine species, unless otherwise indicated.

As used herein, a "phylogenetic cluster" is a set of influenza virus antigens, such as hemagglutinins (HAs) or neuraminidases (NAs), that have been grouped together (on the same branch) in a phylogenetic tree or evolutionary tree that is rooted back to a similar (homologous) ancestor. For the IAV-S neuraminidases and hemagglutinins found in the U.S., the predominant phylogenetic clusters are described in: [Anderson et al., *Influenza and other Respiratory Viruses* 7 (Suppl. 4): 42-51 (2013)].

As used herein, a "lineage" is a set of influenza virus hemagglutinins that have been grouped together (on the same branch) in an evolutionary tree that is rooted back to a similar (homologous) ancestor. These groupings have been made for European hemagglutinins and neuraminidase and are analogous to the phylogenetic clusters for U.S. viruses, but are not equivalent. Lineage determinations can be obtained by phylogenetic analysis of HA or NA sequences in question with pre-established reference sequences using readily available software, i.e., Clustal Omega [Sievers F., et al., (2011) Mol. Syst. Biol. 7:539] or a web-accessible annotation tool for H1 HA sequences [Anderson T K, et al., mSphere, 2016; 1(6):e00275-16].

For the IAV-S hemagglutinin (HAs) found in Europe, there are four predominant lineages, as described in: [Watson et al., *J. Virol.* 89:9920-9931 (2015)] which correspond to 3 H1 HA clades described in Anderson et al., mSphere 1(6):e00275-16 (2016) and one H3 HA clade [Anderson et al., unpublished]. European swine were infected solely by CS lineage viruses until 1979, when an avian H1N1 virus called "Eurasian avian-like swine H1N1" (EA), genetically distinct from the CS lineage, was isolated from pigs in Belgium and Germany. The EA lineage continues to circulate among European swine and has reassorted with human seasonal origin viruses since its emergence, resulting in the cocirculation of three distinct virus subtypes in Europe: (i) Eurasian avian-like H1avN1 (EA or Glade 1C.2.); (ii) A/swine/Gent/1/1984-like H3N2 (Gent/84 or clade 3.1970.1); and (iii) A/swine/Scotland/410440/1994-like $H1_{hu}N2$ (Scot/94 or clade 1B.1). Since April 2009, a novel H1N1 IAV virus, named (iv) A(H1N1)pdm09 or clade 1A.3.3.2 of swine origin spreads throughout the human population. In the context of the present invention, these four lineages are thus referred to as "EA", "Gent/84", "Scot/94" and "pdm09".

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "RNA replicon particle", abbreviated "RP", is an RNA replicon packaged in structural proteins, e.g., the capsid and glycoproteins, which may be derived from an alphavirus, e.g., is an alphavirus RNA replicon particle as described by Pushko et al., [*Virology* 239(2):389-401 (1997)], but may also be a Sindbis virus [Bredenbeek et al., 1993, J. of Virol., vol. 67, p. 6439-6446], and Semliki Forest virus [Liljestrom & Garoff, 1991, Biotechnology (NY), vol. 9, p. 1356-1361]. An RP cannot propagate in cell cultures or animal hosts (without a helper plasmid or analogous component), because the replicon does not encode the alphavirus structural components (e.g., capsid and glycoproteins). Preferably, the RNA RP of the present invention is an alphavirus RNA RP.

The term "non-IAV-S", is used to modify terms such as pathogen, and/or antigen (or immunogen) to signify that the respective pathogen, and/or antigen (or immunogen) is neither an IAV-S pathogen nor an IAV-S antigen (or immunogen) and that a non-IAV-S protein antigen (or immunogen) does not originate from an IAV-S.

The term "originate(s) from" is used herein to signify that the unmodified and/or truncated amino acid sequence of that given protein antigen is encoded by that pathogen or strain of that pathogen. The coding sequence, within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "treatment" or "treating", "prevention" or "preventing", "protecting", or "providing protection to", or "eliciting protective immunity to", "aids in prevention of disease", and "aids in the protection" do not require complete protection from any indication of infection. For example, "for use in the prevention"" can mean that the provided protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection. Hence, the terms "prevention of a disease" or "treatment" encompass a prophylactic treatment against infection with the virus or against a disorder arising from the infection.

As used herein, a "vaccine" is a composition that is suitable for application to an animal, e.g., porcine (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates.

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., porcine.

"Parenteral administration" includes subcutaneous injections, submucosal injections, intravenous injections, intramuscular injections, intradermal injections, and infusion.

Hemagglutinin and neuraminidase antigens of IAV-S may relate to the complete, i.e. the full-length, protein as specified in the sequences as defined herein or may relate to an antigenic fragment thereof, which fragment may equally be suitable to induce an adequate immunological response as is commonly known in the art of influenza vaccines (see e.g. PLOS ONE Research Article "An Influenza A/H1N1/2009 Hemagglutinin Vaccine Produced in *Escherichia coli*", Jose M. Aguilar-Yáñez et al. Jul. 22, 2010; https://doi.org/10.1371/journal.pone.0011694; Vaccines (Basel) "Optimal Use of Vaccines for Control of Influenza A Virus in Swine", Matthew R. Sandbulte et al. 2015 Marc 3(1) 22-73).

In general, an antigenic fragment of a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an IAV-S hemagglutinin (HA) is a fragment of the HA protein that is antigenic, i.e. it fulfills the function of an immunogenic epitope. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity (i.e. capability of inducing the corresponding antibodies as established by an HI or NI inhibition assay as described below) of the full-length protein. In preferred embodiments an antigenic fragment retains at least 50% of the antigenicity of the full-length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues.

As used herein one amino acid sequence is 100% "identical" or has 100% "sequence identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using a web based Clustal Omega, a multiple sequence alignment program with default parameters [Sievers and Higgins, Protein Sci. 2018 January; 27(1):135-1452018]. The percent identity value is a single numeric score determined for each pair of aligned sequences. It measures the number of identical residues ("matches") in relation to the length of the alignment. Next to Clustal Omega, other programs, which may be used to determine nucleotide and amino acid sequence percent identity, are C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. Alternatively, an Advanced Blast search under the default filter conditions can be used, e.g., using the GCG (Genetics Computer Group, Program Manual for the GCG Package, Version 7, Madison, Wisconsin) pileup program using the default parameters.

DETAILED DESCRIPTION OF THE INVENTION

The first embodiment of the first aspect of the present invention relates to a first nucleic acid construct, which combines at least first and second nucleic acid sequences encoding hemagglutinin (HA) antigens in a specific order. The first HA antigen encoded by the first nucleic acid sequence in direction from 5' to 3' of the nucleic acid construct is of the Scot/94 lineage. The second HA antigen encoded by the second nucleic acid sequence in direction from 5' to 3' of the nucleic acid construct is of the EA lineage.

The first HA antigen of the Scot/94 lineage may be of any strain, such as from strain A/swine/Italy/3033-1/2015 (H1N2) or A/swine/France/35-140041 (H1N2). In a preferred embodiment the first HA antigen of the Scot/94 lineage is from strain A/swine/Italy/3033-1/2015 (H1N2).

Further preferably, the first HA antigen comprises, and further more preferably consists of the amino acid sequence according to SEQ ID NO: 3 or an amino acid sequence having at least 85%, at least 87%, at least 89%, at least 90%, 91%, 92%, 93%, 94%, 95%, 96%, 97%, 98%, or 99% sequence identity. Further preferably, the first HA antigen consists of the amino acid sequence of SEQ ID NO: 3 or an amino acid sequence having at least 90%, preferably at least 93%, more preferably at least 95%, 96%, 97%, 98%, or 99% sequence identity.

The second HA antigen of the EA lineage may be of any strain, such as from strain A/swine/Denmark/101048-2/2011 (H1N1), A/swine/Italy/28762-3/2013 (H1N1) or A/swine/France/44-120070/2012 (H1N1). In a preferred embodiment the second HA antigen of the EA lineage is from strain A/swine/Italy/28762-3/2013 (H1N1).

Further preferably, the second HA antigen comprises, and further more preferably consists of the amino acid sequence according to SEQ ID NO: 6 or an amino acid sequence having at least at least 90%, 91%, 92%, 93%, 94%, 95%, 96%, 97%, 98%, or 99% sequence identity. Further preferably, the second HA antigen consists of the amino acid sequence of SEQ ID NO: 6 or an amino acid sequence having at least 93%, preferably at least 95%, further preferably at least 96%, 97%, 98%, or 99% sequence identity.

The second embodiment of the present invention relates to a second nucleic acid construct, which combines at least first and second nucleic acid sequences encoding hemagglutinin (HA) antigens in a specific order. The first HA antigen encoded by the first nucleic acid sequence in direction from 5' to 3' of the nucleic acid construct is of the Gent/84 lineage. The second HA antigen encoded by the second nucleic acid sequence in direction from 5' to 3' of the nucleic acid construct is of the pdm09 lineage.

The first HA antigen of the Gent/84 lineage may be of any strain, such as from strain A/swine/Italy/240849/2015 (H3N2). In a preferred embodiment the first HA antigen of the Gent/84 lineage is from strain A/swine/Italy/240849/2015 (H3N2).

Further preferably, the first HA antigen comprises, and further more preferably consists of the amino acid sequence according to SEQ ID NO: 9 or an amino acid sequence having at least at least 90%, 91%, 92%, 93%, 94%, 95%, 96%, 97%, 98%, or 99% sequence identity. Further preferably, the first HA antigen consists of the amino acid sequence of SEQ ID NO: 9 or an amino acid sequence having at least 93%, preferably at least 95%, further preferably at least 96%, 97%, 98%, or 99% sequence identity.

The second HA antigen of the pdm09 lineage may be of any strain, such as from strain A/swine/England/373/2010 (H1N1). In a preferred embodiment the second HA of the EA lineage is from strain A/swine/England/373/2010 (H1N1).

Further preferably, the second HA antigen comprises, and further more preferably consists of the amino acid sequence according to SEQ ID NO: 12 or an amino acid sequence having at least at least 95%, 96%, 97%, 98%, or 99% sequence identity. Further preferably, the first HA antigen consists of the amino acid sequence of SEQ ID NO: 12 or an amino acid sequence having at least 95%, preferably at least 96%, further preferably at least 97%, 98%, or 99% sequence identity.

In the first embodiment of the second aspect, there is provided a nucleic acid construct comprising first and second nucleic acid sequences:

- a first nucleic acid sequence encoding a first HA antigen of IAV-S of the A/swine/Scotland/410440/1994-like $H1_{hu}N2$ (Scot/94) lineage from strain A/swine/Italy/3033-1/2015 (H1N2), and
- a second nucleic acid sequence encoding a second HA antigen of IAV-S of the Eurasian avian-like $H1_{av}N1$ (EA) lineage from strain A/swine/Italy/28762-3/2013 (H1N1).

Preferably, the amino acid sequence of the first HA antigen of IAV-S of the Scot/94 lineage from strain A/swine/Italy/3033-1/2015 (H1N2) comprises, and further preferably consists of a sequence of SEQ ID NO: 3 or an amino acid sequence having at least 85%, preferably at least 90% sequence identity. The amino acid identity is further preferably at least 91%, 92%, more preferably at least 93%, 94%, 95%, 96%, 97%, 98% or even 99% or more.

Preferably, the amino acid sequence of the second HA antigen of IAV-S of the EA lineage from strain A/swine/Italy/28762-3/2013 (H1N1) comprises, and further preferably consists of a sequence of SEQ ID NO: 6 or an amino acid sequence having at least 90%, preferably at least 93% sequence identity. The amino acid identity is further preferably at least 94%, 95%, more preferably at least 96%, 97%, 98% or even 99% or more.

In the second embodiment of the second aspect, there is provided a nucleic acid construct for use in the prevention or treatment of a disease caused by a Swine influenza A virus in a subject, the nucleic acid construct comprising first and second nucleic acid sequences:

- the first nucleic acid sequence encoding a first hemagglutinin (HA) antigen of a Swine influenza A virus (IAV-S) of the A/swine/Gent/1/1984-like H3N2 (Gent/84) lineage from strain A/swine/Italy/240849/2015 (H3N2), and
- a second nucleic acid sequence encoding a second HA antigen of IAV-S of the A(H1N1)pdm09 (pdm09) lineage from strain A/swine/England/373/2010 (H1N1).

Preferably, the amino acid sequence of the first HA antigen of IAV-S of the Gent/84 lineage from strain A/swine/Italy/240849/2015 (H3N2) comprises, and further preferably consists of a sequence of SEQ ID NO: 9 or an amino acid sequence having at least 90%, preferably at least 95% sequence identity. The amino acid identity is preferably at least 96%, 97%, more preferably at least 98% or even 99% or more.

Preferably, the amino acid sequence of the second HA antigen of IAV-S of the pdm09 lineage from strain A/swine/England/373/2010 (H1N1) comprises, and further preferably consists of a sequence of SEQ ID NO: 12 or an amino acid sequence having at least 90%, preferably at least 95% sequence identity. The amino acid identity is preferably at least 96%, 97%, more preferably at least 98% or even 99% or more.

The nucleic acid constructs according to the first and/or second embodiment of the first and/or second aspect may be included in an expression cassette incorporating the nucleic acid sequences encoding hemagglutinin (HA) antigens as described above as heterologous genes together with transcription- and/or expression controlling nucleic acid sequences, such as alphavirus sub-genomic promoter sequences etc, and which are suitable for expression of the HA antigens. Such expression cassettes can be generated using well known techniques by incorporating the heterologous nucleic acid sequences encoding the HA antigens in a vector, such as DNA vectors or RNA vectors. The vector can be a viral replicon backbone, such as an RNA replicon particle (RP), and preferably is an alphavirus RNA replicon particle.

Thus, in the first and second aspect of the present invention, there is further provided an RNA RP, preferably an alphavirus RNA RP, comprising the nucleotide construct according to the first embodiment. In addition, the present invention further provides an RNA preferably an alphavirus RNA RP, comprising the nucleotide construct according to the second embodiment.

An "alphavirus RNA replicon particle (RP)" is well known as "non-transmissible", "single-cycle", or "propagation-incompetent" virus like particle vector. The genome can encode one or more heterologous genes from its 26S subgenomic promoter. The RP can replicate within the target cell without producing a progeny, and in this way deliver and express heterologous antigen(s) to the immune system of a target animal. The alphavirus RNA RP may be based on a human Venezuelan equine encephalitis vaccine (VEEV) TC-83 strain.

RP expression systems for heterologous expression of antigens are available in the art, and include, for example, the commercially available RP vector-based platforms for the manufacture of vaccines, such as the Alphavaccine Platform System based on the VEE virus and the SEQUIVITY™ Technology available from MSD/Merck Animal Health, USA. Thus, in a further preferred embodiment, the RNA replicon particle is a Venezuelan Equine Encephalitis (VEE) alphavirus-based RNA replicon particle.

For example, the viral HA antigen gene(s) can then be expressed from the (26S-Alphavirus) subgenomic promoter, and transcribed replicon RNA can be packaged into RPs by expression of the structural proteins by a packaging cell lines, or via co-transfection into suitable host cells of the replicon RNA and of one or more 'helper' RNA's encoding the structural proteins. The generation of VEE TC-83 RNA replicon particles is for example described in U.S. Pat. Nos. 9,441,247 and 8,460,913. In short, the HA or NA genes were de novo synthesized (DNA2.0) using sequence from SIV strains. Two HA or three NA genes were cloned into a replicon vector plasmid using monodirectional expression cassettes in tandem and the sequence was confirmed to ensure no mutations were introduced in the cloning process. RNA was generated by in vitro transcription of linearized replicon plasmid DNA using T7 RNA polymerase as described previously [Kamrud et al., Virology. 2007; 360 (2):376-387]. RP were generated by co-electroporation of HA or NA replicon RNA and structural gene helper RNAs into Vero cells and subsequent harvest of the particles [Hooper et al., Vaccine. 2009; 28(2):494-511].

General molecular biological techniques involving cloning, transfection, recombination, selection, and amplification are for example explained in great detail in standard text-books like Sambrook & Russell: "Molecular cloning: a laboratory manual" [2001, Cold Spring Harbour Laboratory Press; ISBN: 0879695773; Ausubel et al., in: Current Protocols in Molecular Biology, J. Wiley and Sons Inc., NY, 2003, ISBN: 047150338X; C. Dieffenbach & G. Dveksler: "PCR primers: a laboratory manual", CSHL Press, ISBN 0879696540; and "PCR protocols", by: J. Bartlett and D. Stirling, Humana press, ISBN: 0896036421].

The nucleic acid constructs of the present invention can be used in immunogenic compositions comprising the nucleic acid constructs. Preferably, the immunogenic compositions comprise one of more replicon particles comprising the nucleic acid constructs of the present invention. Thus, the replicon particles of the present invention can be used in immunogenic compositions, such as vaccines, comprising the replicon particles. The immunogenic compositions or vaccines may consist of the replicon particles or may comprise the replicon particles in combination with additional components, such as carriers or adjuvants. The immunogenic compositions of the present invention may be used in vaccines for use in the prevention of a disease caused by a Swine influenza A virus (IAV-S) in a subject.

Thus, in the first and/or second aspects, the present invention further provides an immunogenic composition comprising or consisting of RNA RP comprising the nucleic acid construct according to the first embodiment. Alternatively, the present invention further provides an immunogenic composition comprising or consisting of RNA RP comprising the nucleic acid construct according to the second embodiment.

In a preferred embodiment of the first and/or second aspects, the present invention provides an immunogenic composition comprising a first RNA RP comprising the nucleotide construct according to the first embodiment and a second RNA RP comprising the nucleotide construct according to the second embodiment. It could be shown in the present invention that an immunogenic composition comprising a combination of replicon particles according to the first and second embodiment provide for broad protection against the existing IAV-S lineages, and thus such an immunogenic composition can beneficially be used as a vaccine that aid in the protection, i.e. that aid in the prevention or treatment, of the vaccinated subject, such as swine (e.g. sow or piglet) against IAV-S infection.

Therefore, in a preferred embodiment, the present invention provides an immunogenic composition, such as vaccine, comprising first and second RNA replicon particles, (i) the first RNA replicon particle, preferably an alphavirus RNA replicon particle, comprising a nucleic acid construct, comprising first and second nucleic acid sequences encoding first and second hemagglutinin (HA) antigens of a Swine influenza A virus (IAV-S), wherein
  the first HA antigen is a of the Gent/84 lineage, and
  the second HA antigen is of the pdm09 lineage,
(ii) the second RNA replicon particle, preferably an alphavirus RNA replicon particle, comprising a nucleic acid construct comprising third and fourth nucleic acid sequences encoding third and fourth HA antigens of IAV-S, wherein
  the third HA antigen is of the Scot/94 lineage, and
  the fourth HA antigen is of the EA lineage.

In a particularly preferred embodiment, the present invention provides an immunogenic composition, such as a vaccine, that comprises first and second RNA replicon particles:

(i) the first RNA replicon particle, preferably an alphavirus RNA replicon particle,
  comprising a first nucleic acid construct comprising, in the order from 5' to 3' of the nucleic acid sequence:
  a first nucleic acid sequence encoding a first HA antigen of IAV-S of the Scot/94 lineage, and a second nucleic acid sequence encoding a second HA antigen of IAV-S of the EA lineage, and the immunogenic composition further comprises:

(ii) the second RNA replicon particle, preferably an alphavirus RNA replicon particle, comprising a second nucleic acid construct comprising, in the order from 5' to 3' of the nucleic acid sequence:

a third nucleic acid sequence encoding a third HA antigen of IAV-S of the Gent/84 lineage, and a fourth nucleic acid sequence encoding a fourth HA antigen of IAV-S of the pdm09 lineage.

In a particularly preferred embodiment, the present invention provides an immunogenic composition, such as a vaccine, that comprises first and second RNA replicon particles:

(i) the first RNA replicon particle, preferably an alphavirus RNA replicon particle, comprising a first nucleic acid construct comprising, in the order from 5' to 3' of the nucleic acid sequence:

a first nucleic acid sequence encoding a first HA antigen of IAV-S of the Scot/94 lineage, and a second nucleic acid sequence encoding a second HA antigen of IAV-S of the EA lineage, and the immunogenic composition further comprises:

(ii) the second RNA replicon particle, preferably an alphavirus RNA replicon particle, comprising a second nucleic acid construct comprising, in the order from 5' to 3' of the nucleic acid sequence:

a third nucleic acid sequence encoding a third HA antigen of IAV-S of the Gent/84 lineage, and a fourth nucleic acid sequence encoding a fourth HA antigen of IAV-S of the pdm09 lineage.

Thus, in a third aspect the present invention provides an immunogenic composition, such as vaccine, comprising first and second RNA replicon particles, (i) the first RNA replicon particle, preferably an alphavirus RNA replicon particle, comprising a nucleic acid construct, comprising first and second nucleic acid sequences encoding, in the order from 5' to 3' of the nucleic acid sequence, first and second hemagglutinin (HA) antigens of a Swine influenza A virus (IAV-S), wherein the first HA antigen encoded by the first nucleic acid sequence is of the Gent/84 lineage from strain A/swine/Italy/240849/2015 (H3N2), preferably of SEQ ID NO. 9 or an amino acid sequence having at least 90% sequence identity thereof, and the second HA antigen encoded by the first nucleic acid sequence is of the pdm09 lineage from strain A/swine/England/373/2010 (H1N1), preferably of SEQ ID NO. 12 or an amino acid sequence having at least 95% sequence identity thereof (ii) the second RNA replicon particle, preferably an alphavirus RNA replicon particle, comprising a nucleic acid construct comprising third and fourth nucleic acid sequences encoding, in the order from 5' to 3' of the nucleic acid sequence, third and fourth HA antigens of IAV-S, wherein the third HA antigen encoded by the third nucleic acid sequence is of the Scot/94 lineage from strain A/swine/Italy/3033-1/2015 (H1N2), preferably of SEQ ID NO. 3, or an amino acid sequence having at least 85% sequence identity thereof, and the fourth HA antigen encoded by the fourth nucleic acid sequence is of the EA lineage from strain A/swine/Italy/28762-3/2013 (H1N1), preferably of SEQ ID NO. 6, or an amino acid sequence having at least 90% sequence identity thereof.

The nucleic acid constructs, immunogenic compositions and replicon particles of the third aspects are as described above for the first and second aspects of the present invention. Thus, further encompassed by the present invention are any combinations of the embodiments of the third aspect with the embodiments of the first and second aspects as described herein. Thus, the present invention further provides replicon particles as described in the third aspect, wherein the nucleic acid constructs encode IAV-S HA antigens, which are arranged in the specific order as defined in the first aspect and/or in which the IAV-S antigens are from the specific strains as defined in the second aspect.

The immunogenic composition may be adapted for simultaneous or consecutive administration of the first and second RNA replicon particles as described above, i.e. for simultaneous or consecutive administration of the RNA RP comprising the nucleic acid constructs according to the first and second embodiment. Preferably, the immunogenic composition is adapted for simultaneous administration of the first and second RNA replicon particles. Hence, in the preferred embodiment, the immunogenic composition comprises the first and second RNA replicon particles in a unit dosage form.

In a further preferred embodiment, the immunogenic composition may comprise one or more additional RNA replicon particles. Such additional RNA RPs may comprise nucleic acid constructs encoding one or more additional antigens. For example, the additional RNA RPs may comprise nucleic acid constructs encoding one or more neuraminidase (NA) antigens of IAV-S. In specific embodiments, the nucleic acid constructs encode two or three, preferably three NA antigens of IAV-S, or immunogenic fragments thereof.

In a particularly preferred embodiment, the additional RNA RPs comprises a nucleic acid construct comprising first, second and third nucleic acid sequences encoding first, second and third NA antigens of IAV-S, wherein the first NA antigen is of the Scot/94 lineage, the second NA antigen is of the Gent/84 lineage, and the third NA antigen is selected from the pdm09 lineage or the EA lineage.

Accordingly, in a fourth aspect of the present invention, there is provided a nucleic acid construct comprising first, second and third nucleic acid sequences encoding first, second and third NA antigens of IAV-S, wherein the first NA antigen encoded by the first nucleic acid sequence is of the Scot/94 lineage, the second NA antigen encoded by the second nucleic acid sequence is of the Gent/84 lineage, and the third NA antigen encoded by the third nucleic acid sequence is selected from the pdm09 lineage or the EA lineage.

Preferably, the amino acid sequence of the first NA antigen of IAV-S of the Scot/94 lineage is from strain A/swine/England/61470/2013 (H1N2). The amino acid sequence of the first NA antigen preferably comprises, and further preferably consists of a sequence of SEQ ID NO: 15 or an amino acid sequence having at least 90% sequence identity. The amino acid identity is preferably at least 96%, 97%, more preferably at least 98% or even 99% or more.

Preferably, the amino acid sequence of the second NA antigen of IAV-S of the Gent/84 lineage is from strain A/swine/Italy/248147-8/2015 (H3N2). The amino acid sequence of the second NA antigen preferably comprises, and further preferably consists of a sequence of SEQ ID NO: 18 or an amino acid sequence having at least 90% sequence identity. The amino acid identity is preferably at least 96%, 97%, more preferably at least 98% or even 99% or more.

Preferably, the amino acid sequence of the third NA antigen of IAV-S of the pdm09 lineage is from strain A/swine/England/373/2010 (H1N1) or A/swine/Italy/179057/2015 (H1N1), preferably from strain A/swine/Italy/179057/2015 (H1N1). The amino acid sequence of the third NA antigen preferably comprises, and further preferably consists of a sequence of SEQ ID NO: 21 or an amino acid sequence having at least 90% sequence identity. The amino acid identity is preferably at least 96%, 97%, more preferably at least 98% or even 99% or more.

Alternatively, the amino acid sequence of the third NA antigen of IAV-S of the EA lineage is from strain A/swine/Italy/28762-3/2013 (H1N1). The amino acid sequence of the third NA antigen preferably comprises, and further preferably consists of a sequence of SEQ ID NO: 24 or an amino acid sequence having at least 90% sequence identity. The amino acid identity is preferably at least 96%, 97%, more preferably at least 98% or even 99% or more.

There is further provided an RNA replicon particle, preferably an alphavirus RNA replicon particle, comprising a nucleic acid construct comprising first, second and third nucleic acid sequences encoding first, second and third neuraminidase (NA) antigens of a Swine influenza A virus (IAV-S), wherein the first NA antigen is of the Scot/94 lineage, the second NA antigen is of the Gent/84 lineage, and the third NA antigen is selected from the pdm09 lineage or the EA lineage.

The replicon particle comprising the nucleic acid construct according to the fourth aspect may be used alone or in combination with the replicon particle according to the first, second and/or third aspect of the present invention as described herein and is beneficially be used in combination with the replicon particle comprising the hemagglutinin antigens as described in the first, second and/or third aspects of the present invention.

The replicon particle according to this fourth aspect is not particularly limited and is preferably a replicon particle, such as an alphavirus replicon particle, most preferably a Venezuelan Equine Encephalitis Virus (VEEV) alphavirus RNA replicon particle as described in the first, second and/or third aspect.

In a further preferred embodiment, the present invention provides an immunogenic composition, such as a vaccine, comprising at least first, second and third RNA replicon particles, the first RNA replicon particle comprising a nucleic acid construct, comprising, in the order from 5' to 3' of the nucleic acid sequence, first and second nucleic acid sequences encoding first and second HA antigens of IAV-S, wherein the first HA antigen is of the Scot/94 lineage, and the second HA antigen is of the EA lineage, the second RNA replicon particle comprising a nucleic acid construct comprising, in the order from 5' to 3' of the nucleic acid sequence, third and fourth nucleic acid sequences encoding third and fourth HA antigens of IAV-S, wherein the third HA antigen is of the Gent/84 lineage, and the fourth HA antigen is of the pdm09 lineage, and the third RNA replicon particle comprises a nucleic acid construct comprising first, second and third nucleic acid sequences encoding first, second and third NA antigens of IAV-S, wherein the first NA antigen is of the Scot/94 lineage, the second NA antigen is of the Gent/84 lineage, and the third NA antigen is selected from the pdm09 lineage or the EA lineage The immunogenic composition described above, such as a vaccine, can beneficially be used as a vaccine that aid in the protection of the vaccinated subject, such as swine (e.g. sow or piglet) against IAV-S infection.

The immunogenic composition may be adapted for simultaneous or consecutive administration of the first, second and third RNA replicon particles as described above, i.e. for simultaneous or consecutive administration of the RNA RP comprising the nucleic acid constructs according to the first, second and/or third aspect in combination with the nucleic acid construct according to the fourth aspect. Preferably, the immunogenic composition is adapted for simultaneous administration of the first, second and third RNA replicon particles. Hence, in the preferred embodiment, the immunogenic composition comprises the first, second and third RNA replicon particles in a unit dosage form.

The present invention also provides vaccines against multiple porcine pathogens. For example, the coding sequence of a protein antigen or antigenic fragment thereof, or combination of such coding sequences of protein antigens useful in a porcine vaccine can be added to an RNA replicon particle (RP) and/or combined in the same RP as one that encodes an HA or NA originating from an IAV-S in the vaccine, as described herein. Examples of pathogens that one or more of protein antigens or antigenic fragments thereof can originate from include porcine reproductive and respiratory syndrome virus (PRRS), porcine circovirus (PCV), transmissible gastroenteritis virus (TGE), porcine pseudorabies virus (PPRV), porcine parvovirus (PPV), porcine rotavirus (PRV), porcine epidemic diarrhea virus (PED), *Pasteurella multocida* of multiple serotypes, *Salmonella* ssp., *Escherichia coli*, e.g., (serotypes K99, K88, 987P, or F41), *Haemophilus parasuis, Lawsonia intracellularis, Mycoplasma* ssp. (e.g., *Mycoplasma hyopneumoniae*), *Bordetella bronchiseptica, Erysipelas* ssp., *Campylobacter* ssp., *Actinobacillus pleuropneumoniae, Clostridium perfringens*, and *Clostridium difficile*.

In addition, the present invention provides vaccines comprising one or more RPs of the present invention in combination with one or more other vectors encoding one or more of these porcine antigens (e.g., a baculovirus vector encoding an ORF-2 protein from a porcine circovirus-2, (PCV-2) and/or porcine circovirus-3 (PCV-3) and/or inactivated toxoids originating from one or more of these porcine pathogens. Moreover, such vaccines can include any RNA replicon particle that encodes a HA and/or NA originating from an IAV-S in a vaccine of the present invention together with one or more killed and/or modified (attenuated) live porcine virus isolates and/or porcine bacteria.

Accordingly, one or more RNA RPs that encode one or more HAs and/or NAs originating from IAV-S can be added together with one or more other vectors encoding one or more porcine antigen and/or one or more killed and/or modified (attenuated) live virus isolates such as one or more killed or modified live IAS-V strain, one or more killed and/or modified live PRRS virus, one or more killed and/or modified live PCV, one or more killed, and/or modified live TGE, one or more killed and/or modified live PPRV, one or more killed and/or modified live PPV, one or more killed and/or modified live PRV and one or more killed and/or modified live PED. Moreover, one or more alphavirus RNA replicon particles (RPs) that encode one or more HAs or NAs originating from IAV-S can be added together with one or more other vectors encoding one or more porcine antigen and/or added together with one or more killed and/or modified (attenuated) live bacteria that can infect swine too, including one or more killed and/or modified live *Pasteurella multocida* (of one or more multiple serotypes), *Salmonella* ssp., *Escherichia coli* (of one or more multiple serotypes), *Haemophilus parasuis, Lawsonia intracellularis, Mycoplasma* ssp. (e.g., *Mycoplasma hyopneumoniae*), *Bordetella bronchiseptica, Erysipelas* ssp., *Campylobacter* ssp., *Actinobacillus pleuropneumoniae, Clostridium perfringens*, and *Clostridium difficile*.

Accordingly, the present invention also includes all of the RNA replicon particles of the present invention, naked DNA vectors that comprise the nucleic acid constructs of the present invention, naked RNA vectors that comprise the nucleic acid constructs of the present invention, the nucleic acid constructs of the present invention including synthetic messenger RNA, and RNA replicons, as well as all of the immunogenic compositions and/or vaccines that comprise the nucleic acid constructs (e.g., synthetic messenger RNA, RNA replicons), the alphavirus RNA replicon particles, naked RNA vectors, and/or the naked DNA vectors of the present invention.

The immunogenic composition of the present invention can be used as a vaccine, which may be a non-adjuvanted vaccine or an adjuvanted vaccine. Thus, the present invention further comprises vaccines (multivalent) vaccines comprising the immunogenic compositions of the present invention. In particular embodiments, the vaccines are a nonadjuvanted vaccine. In other embodiments, the vaccines comprise an adjuvant. Adjuvants suitable for use in the vaccine of the present invention are not particularly limited, and may comprise one or more adjuvants selected from the group consisting of a biodegradable oil, an oil-in-water emulsion with 2.5-50% (v/v) mineral oil, and a biodegradable oil mixed with an oil-in-water emulsion with 2.5-50% (v/v) mineral oil.

In particular embodiments, the adjuvant is a biodegradable oil. In specific embodiments of this type, the biodegradable oil is dl-α-tocopheryl acetate (vitamin E acetate). In other embodiments, the adjuvant comprises an oil-in-water emulsion with 2.5%-50% (v/v) mineral oil. In specific embodiments the adjuvant comprises an oil-in-water emulsion with 2.5% (v/v) mineral oil. In related embodiments, the adjuvant comprises is an oil-in-water emulsion with 5% (v/v) mineral oil. In other embodiments, the adjuvant comprises an oil-in-water emulsion with 12.5% (v/v) mineral oil. In still other embodiments, the adjuvant comprises an oil-in-water emulsion with 25% (v/v) mineral oil. In yet other embodiments, the adjuvant comprises an oil-in-water emulsion with 50% (v/v) mineral oil. In more specific embodiments the adjuvant comprises a mixture of a biodegradable oil with a mineral oil adjuvant. In specific embodiments, the biodegradable oil is dl-α-tocopheryl acetate and the mineral oil is a liquid paraffin. In more specific embodiments, the biodegradable oil is dl-α-tocopheryl acetate and the mineral oil is a light liquid paraffin.

In related formulations, the adjuvant is a mixture of two components. The first component consists of mineral oil droplets with an approximate average (volume weighed) size around 1 am, which is stabilized with polysorbate 80 (polyoxyethylene (20) sorbitan monooleate) in water. The first component can comprise 25 weight percent of the mineral oil and 1 weight percent of the polysorbate 80, with the remainder water. The second component can consist of droplets of biodegradable dl-α-tocopheryl acetate with an approximate average (volume weighed) size of 400 nm, which is also stabilized with polysorbate 80. Particular formulations comprise 15 weight percent of dl-α-tocopheryl acetate and 6 weight percent of polysorbate 80, with the remainder water. In particular embodiments, the adjuvant is XSOLVE™ (which is a combination of two component adjuvants: DILUVAC FORTE™ which is based on dl-α-tocopheryl acetate and MICROSOL™, which is based on light liquid paraffin [see e.g., U.S. Pat. No. 8,597,662]. In related formulations, the adjuvant contains oil droplets of sub-micrometer size and droplets of biodegradable oil, with the droplets of the biodegradable oil having an average size that differs from the average size of the droplets of mineral oil [see e.g., U.S. Pat. No. 9,084,768].

In certain embodiments, the vaccine aids in the prevention of disease due to IAV-S. In related embodiments, antibodies are induced in a porcine subject when the porcine is immunized with the vaccine. In certain embodiments, the porcine subject is a sow. In related embodiments, the vaccine provides protective maternal antibodies to progeny of the vaccinated sow. In other embodiments, the porcine subject is a piglet. In particular embodiments of this type, the vaccine is administered to a piglet as early as 3 days of age. In specific embodiments, the vaccine is administered as a booster vaccine. In certain embodiments, the vaccine is administered as a single dose vaccine. In specific embodiments of this type, the vaccine is administered as a booster vaccine. In yet other embodiments, the vaccine is administered as a multi-dose vaccine. In specific embodiments of this type, the vaccine is administered as a two-dose vaccine.

The present invention also provides methods of immunizing a porcine (e.g., a sow or a piglet) against a porcine pathogen, e.g., IAV-S, comprising administering to the porcine an immunologically effective amount of a vaccine or multivalent of the present invention. In particular embodiments, the vaccine is administered via intramuscular injection. In alternative embodiments, the vaccine is administered via subcutaneous injection. In other embodiments, the vaccine is administered via intravenous injection. In still other embodiments, the vaccine is administered via intradermal injection. In yet other embodiments, the vaccine is administered via oral administration. In still other embodiments, the vaccine is administered via intranasal administration. A preferred method is intradermal administration. Another preferred method is intramuscular administration Accordingly, the vaccines and multivalent vaccines of the present invention can be administered as a primer vaccine and/or as a booster vaccine. In specific embodiments, a vaccine of the present invention is administered as a one-shot vaccine (one dose), without requiring subsequent administrations. In certain embodiments, in the case of the administration of both a primer vaccine and a booster vaccine, the primer vaccine and the booster vaccine can be administered by the identical route.

In certain embodiments of this type, the primer vaccine and the booster vaccine are both administered by intradermal injection. In other embodiments of this type, the primer vaccine and the booster vaccine are both administered by intramuscular injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by intradermal injection and the booster vaccine can be administered orally. In related embodiments of this type, the primer vaccine can be administered by intramuscular injection and the booster vaccine can be administered orally. In other embodiments of this type, the primer vaccine can be administered by intramuscular injection and the booster vaccine can be administered by intradermal injection. In still other embodiments of this type, the primer vaccine can be administered by intradermal injection and the booster vaccine can be administered by intramuscular injection. The skilled artisan will appreciate that the vaccine composition is preferably formulated appropriately for each type of recipient animal and route of administration.

The present invention further provides a method of immunizing a porcine against IAV-S, the method comprising administering to the porcine an immunologically effective amount of the vaccine of the present invention. The method preferably comprises intradermal administration of the vaccine. The invention further provides for a method of immunizing a porcine (e.g., a sow or a piglet) against IAV-S comprising injecting the porcine with an immunologically effective amount of the above described inventive vaccines, so that the porcine produces appropriate IAV-S antibodies. In particular embodiments, the vaccines can include from about $1\times10^4$ to about $1\times10^{10}$ RPs or higher, for example. In more particular embodiments, the vaccines can include from about $1\times10^5$ to about $1\times10^9$ RPs. In even more particular embodiments, the vaccines can include from about $1\times10^6$ to about $1\ 35\times10^8$ RPs.

In particular embodiments, the vaccines of the present invention are administered in 0.05 mL to 3 mL doses. In more particular embodiments, the dose administered is 0.1 mL to 2 mL. In still more particular embodiments, the dose administered is 0.2 mL to 1.5 mL. In even more particular embodiments, the dose administered is 0.3 to 1.0 mL. In still more particular embodiments, the dose administered is 0.4 mL to 0.8 mL.

Thus, in a first aspect, the present invention provides the following embodiments:

[1] A nucleic acid construct for use in the prevention of a disease caused by a Swine influenza A virus (IAV-S) in a subject, the nucleic acid construct comprising, in the order from 5' to 3' of the nucleic acid sequence:
- a first nucleic acid sequence encoding a first hemagglutinin (HA) antigen of IAV-S of the A/swine/Scotland/410440/1994-like $H1_{hu}N2$ (Scot/94) lineage, and
- a second nucleic acid sequence encoding a second HA antigen of IAV-S of the Eurasian avian-like $H1_{av}N1$ (EA) lineage.

[2] The nucleic acid construct for use as defined in [1], wherein the first HA antigen is from strain A/swine/Italy/3033-1/2015 (H1N2).

[3] The nucleic acid construct for use as defined in [1] or [2], wherein the first HA antigen encoded by the first nucleic acid sequence comprises an amino acid sequence of SEQ ID NO: 3 or an amino acid sequence having at least 85% sequence identity thereof.

[4] The nucleic acid construct for use as defined in any one of [1] to [3], wherein the second HA antigen is from strain A/swine/Italy/28762-3/2013 (H1N1).

[5] The nucleic acid construct for use as defined in any one of [1] to [4], wherein the second HA antigen encoded by the second nucleic acid sequence comprises an amino acid sequence of SEQ ID NO: 6 or an amino acid sequence having at least 90% sequence identity thereof.

[6] A nucleic acid construct for use in the prevention of a disease caused by a Swine influenza A virus (IAV-S) in a subject, the nucleic acid construct comprising, in the order from 5' to 3' of the nucleic acid sequence:
- a first nucleic acid sequence encoding a first HA antigen of IAV-S of the A/swine/Gent/1/1984-like H3N2 (Gent/84) lineage, and
- a second nucleic acid sequence encoding a second HA antigen of IAV-S of the A(H1N1)pdm09 (pdm09) lineage.

[7] The nucleic acid construct for use as defined in [6], wherein the first HA antigen is from strain A/swine/Italy/240849/2015 (H3N2).

[8] The nucleic acid construct for use as defined in [6] or [7], wherein the first HA antigen encoded by the first nucleic acid sequence comprises an amino acid sequence of SEQ ID NO: 9 or an amino acid sequence having at least 90% sequence identity thereof.

[9] The nucleic acid construct for use as defined in any one of [6] to [8], wherein the second HA antigen is from strain A/swine/England/373/2010 (H1N1).

[10] The nucleic acid construct for use as defined in any one of [6] to [9], wherein the second HA antigen encoded by the second nucleic acid sequence comprises an amino acid sequence of SEQ ID NO: 12 or an amino acid sequence having at least 95% sequence identity thereof.

[11] An RNA replicon particle comprising the nucleic acid construct as defined in any one of [1] to [5].

[12] An RNA replicon particle comprising the nucleic acid construct as defined in any one of [6] to [10].

[13] The RNA replicon particle as defined in [15] or [16], which is an alphavirus RNA replicon particle.

[14] The RNA replicon particle as defined in [13], which is a Venezuelan Equine Encephalitis (VEE) alphavirus RNA replicon particle

[15] An immunogenic composition, comprising the RNA replicon particle of any one of [11] to [14].

[16] The immunogenic composition as defined in [15] comprising the RNA replicon particle of [11] and [12].

[17] The immunogenic composition as defined in [16], which is adapted for simultaneous administration of the alphavirus RNA replicon particles as defined in [11] and [12].

[18] A vaccine comprising the immunogenic composition as defined in any one of [15] to [17].

[19] The vaccine as defined in [18], which is a nonadjuvanted vaccine.

[20] The vaccine as defined in [18], which comprises an adjuvant selected from the group consisting of a biodegradable oil, an oil-in-water emulsion with 2.5-50% (v/v) mineral oil, and a biodegradable oil mixed with an oil-in-water emulsion with 2.5-50% (v/v) mineral oil.

[21] The vaccine as defined in any one of [18] to [20] for use in the prevention of a disease caused by a Swine influenza A virus in a subject.

[22] A method of immunizing a porcine against a swine influenza A virus, the method comprising administering to the porcine an immunologically effective amount of the vaccine of any one of [18] to [20].

[23] A nucleic acid construct comprising, in the order from 5' to 3' of the nucleic acid sequence:
- a first nucleic acid sequence encoding a first HA antigen of a Swine influenza A virus (IAV-S) of the A/swine/Scotland/410440/1994-like $H1_{hu}N2$ (Scot/94) lineage, and
- a second nucleic acid sequence encoding a second HA antigen of IAV-S of the Eurasian avian-like $H1_{av}N1$ (EA) lineage.

[24] A nucleic acid construct comprising, in the order from 5' to 3' of the nucleic acid sequence:

a first nucleic acid sequence encoding a first HA antigen of IAV-S of the A/swine/Gent/1/1984-like H3N2 (Gent/84) lineage, and a second nucleic acid sequence encoding a second HA antigen of IAV-S of the A(H1N1)pdm09 (pdm09) lineage.

In a second aspect, the present invention provides the following embodiments:

[1] A nucleic acid construct for use in the prevention of a disease caused by a Swine influenza A virus in a subject, the nucleic acid construct comprising first and second nucleic acid sequences:

a first nucleic acid sequence encoding a first HA antigen of IAV-S of the A/swine/Scotland/410440/1994-like $H1_{hu}N2$ (Scot/94) lineage from strain A/swine/Italy/3033-1/2015 (H1N2), and a second nucleic acid sequence encoding a second HA antigen of IAV-S of the Eurasian avian-like $H1_{av}N1$ (EA) lineage from strain A/swine/Italy/28762-3/2013 (H1N1).

[2] The nucleic acid construct for use as defined in [1], wherein the first HA antigen encoded by the first nucleic acid sequence comprises an amino acid sequence of SEQ ID NO: 3 or an amino acid sequence having at least 85% sequence identity thereof.

[3] The nucleic acid construct for use as defined in [1] or [2], wherein the second HA antigen encoded by the second nucleic acid sequence comprises an amino acid sequence of SEQ ID NO: 6 or an amino acid sequence having at least 90% sequence identity thereof.

[4] A nucleic acid construct for use in the prevention of a disease caused by a Swine influenza A virus in a subject, the nucleic acid construct comprising first and second nucleic acid sequences:

the first nucleic acid sequence encoding a first hemagglutinin (HA) antigen of a Swine influenza A virus (IAV-S) of the A/swine/Gent/1/1984-like H3N2 (Gent/84) lineage from strain A/swine/Italy/240849/2015 (H3N2), and a second nucleic acid sequence encoding a second HA antigen of IAV-S of the A(H1N1)pdm09 (pdm09) lineage from strain A/swine/England/373/2010 (H1N1).

[5] The nucleic acid construct for use as defined in [4], wherein the first HA antigen encoded by the first nucleic acid sequence comprises an amino acid sequence of SEQ ID NO: 9 or an amino acid sequence having at least 95% sequence identity thereof.

[6] The nucleic acid construct for use as defined in [4] or [5], wherein the second HA antigen encoded by the second nucleic acid sequence comprises an amino acid sequence of SEQ ID NO: 12 or an amino acid sequence having at least 95% sequence identity thereof.

[7] An RNA replicon particle comprising the nucleotide construct as defined in any one of [1] to [3].

[8] An RNA replicon particle comprising the nucleotide construct as defined in any one of [4] to [6].

[9] The RNA replicon particle as defined in [7] or [8], which is an alphavirus RNA replicon particle

[10] The RNA replicon particle as defined in [9], which is a Venezuelan Equine Encephalitis Virus (VEEV) alphavirus RNA replicon particle

[11] An immunogenic composition, comprising the RNA replicon particle as defined in any one of [7] to [10].

[12] The immunogenic composition as defined in [11] comprising the RNA replicon particle as defined in [7] and [8].

[13] A vaccine comprising the immunogenic composition as defined in [12].

[14] The vaccine as defined in [13], which is a nonadjuvanted vaccine.

[15] The vaccine as defined in [13], which comprises an adjuvant selected from the group consisting of a biodegradable oil, an oil-in-water emulsion with 2.5-50% (v/v) mineral oil, and a biodegradable oil mixed with an oil-in-water emulsion with 2.5-50% (v/v) mineral oil.

[16] The vaccine as defined in any one of [13] to [15] for use in the prevention of a disease caused by a Swine influenza A virus in a subject.

[17] A method of immunizing a porcine against a swine influenza A virus, the method comprising administering to the porcine an immunologically effective amount of the vaccine as defined in any one of [14] to [16].

[18] A nucleic acid construct comprising first and second nucleic acid sequences:

the first nucleic acid sequence encoding a first hemagglutinin (HA) antigen of a Swine influenza A virus (IAV-S) of the A/swine/Gent/1/1984-like H3N2 (Gent/84) lineage from strain A/swine/Italy/240849/2015 (H3N2), and a second nucleic acid sequence encoding a second HA antigen of IAV-S of the A(H1N1)pdm09 (pdm09) lineage from strain A/swine/England/373/2010 (H1N1).

[19] A nucleic acid construct comprising first and second nucleic acid sequences:

a first nucleic acid sequence encoding a first HA antigen of IAV-S of the A/swine/Scotland/410440/1994-like $H1_{hu}N2$ (Scot/94) lineage from strain A/swine/Italy/3033-1/2015 (H1N2), and a second nucleic acid sequence encoding a second HA antigen of IAV-S of the Eurasian avian-like $H1_{av}N1$ (EA) lineage from strain A/swine/Italy/28762-3/2013 (H1N1).

In a third aspect, the present invention provides the following embodiments:

[1] An immunogenic composition for use in the prevention of a disease caused by a Swine influenza A virus in a subject, the composition comprising first and second RNA replicon particles, the first RNA replicon particle comprising a nucleic acid construct, comprising first and second nucleic acid sequences encoding first and second hemagglutinin (HA) antigens of a Swine influenza A virus (IAV-S), wherein the first HA antigen is a of the A/swine/Gent/1/1984-like H3N2 (Gent/84) lineage, and the second HA antigen is of the A(H1N1)pdm09 (pdm09) lineage, the second RNA replicon particle comprising a nucleic acid construct comprising third and fourth nucleic acid sequences encoding third and fourth HA antigens of IAV-S, wherein the third HA antigen is of the A/swine/Scotland/410440/1994-like $H1_{hu}N2$ (Scot/94) lineage, and the fourth HA antigen is of the Eurasian avian-like $H1_{av}N1$ (EA) lineage.

[2] The immunogenic composition for use as defined in [1], wherein the first HA antigen is from strain A/swine/Italy/240849/2015 (H3N2).

[3] The immunogenic composition for use as defined in [1] or [2], wherein the first HA antigen encoded by the first nucleic acid sequence comprises an amino acid sequence of SEQ ID NO: 9 or an amino acid sequence having at least 90% sequence identity thereof.

[4] The immunogenic composition for use as defined in any one of the preceding [1] to [3], wherein the second HA antigen is from strain A/swine/England/373/2010 (H1N1).

[5] The immunogenic composition for use as defined in any one of the preceding [1] to [4], wherein the second HA antigen encoded by the second nucleic acid sequence comprises an amino acid sequence of SEQ ID NO: 12 or an amino acid having at least 95% sequence identity thereof.

[6] The immunogenic composition for use as defined in any one of the preceding [1] to [5], wherein the third HA antigen is from strain A/swine/Italy/3033-1/2015 (H1N2).

[7] The immunogenic composition for use as defined in any one of the preceding [1] to [6], wherein the third HA antigen encoded by the third nucleic acid sequence comprises an amino acid sequence of SEQ ID NO: 3 or an amino acid sequence having at least 85% sequence identity thereof.

[8] The immunogenic composition for use as defined in any one of the preceding [1] to [7], wherein the fourth HA antigen is from strain A/swine/Italy/28762-3/2013 (H1N1).

[9] The immunogenic composition for use as defined in any one of the preceding [1] to [8], wherein the fourth HA antigen encoded by the fourth nucleic acid sequence comprises an amino acid sequence of SEQ ID NO: 6 or an amino acid sequence having at least 90% sequence identity thereof.

[10] The immunogenic composition for use as defined in any one of the preceding [1] to [9], which is adapted for simultaneous administration of the first and second RNA replicon particles.

[11] The immunogenic composition for use as defined in any one of the preceding [1] to [10], further comprising a third RNA replicon particle, the third RNA replicon particle comprising a nucleic acid construct, comprising first, second and third nucleic acid sequences encoding first, second and third neuraminidase (NA) antigens of IAV-S, wherein the first NA antigen is of the A/swine/Scotland/410440/1994-like $H1_{hu}N2$ (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}N1$ (EA) lineage.

[12] The immunogenic composition for use as defined in any one of the preceding [1] to [11], wherein the RNA replicon particle is an alphavirus RNA replicon particle.

[13] The immunogenic composition for use as defined in [12], which is a Venezuelan Equine Encephalitis Virus (VEEV) alphavirus RNA replicon particle.

[14] A vaccine comprising the immunogenic composition as defined in any one of the preceding [1] to [13].

[15] The vaccine as defined in [14], which is a nonadjuvanted vaccine.

[16] The vaccine as defined in [14], which comprises an adjuvant selected from the group consisting of a biodegradable oil, an oil-in-water emulsion with 2.5-50% (v/v) mineral oil, and a biodegradable oil mixed with an oil-in-water emulsion with 2.5-50% (v/v) mineral oil.

[17] The vaccine as defined in any one of [14] to [16] for use in the prevention of a disease caused by a Swine influenza A virus in a subject.

[18] A method of immunizing a porcine against a swine influenza A virus, the method comprising administering to the porcine an immunologically effective amount of the vaccine as defined in any one of [14] to [16].

[19] An immunogenic composition comprising first and second RNA replicon particles, the first RNA replicon particle comprising a nucleic acid construct, comprising first and second nucleic acid sequences encoding first and second hemagglutinin (HA) antigens of a Swine influenza A virus (IAV-S), wherein the first HA antigen is a of the A/swine/Gent/1/1984-like H3N2 (Gent/84) lineage, and the second HA antigen is of the A(H1N1)pdm09 (pdm09) lineage, the second RNA replicon particle comprising a nucleic acid construct comprising third and fourth nucleic acid sequences encoding third and fourth HA antigens of IAV-S, wherein the third HA antigen is of the A/swine/Scotland/410440/1994-like $H1_{hu}N2$ (Scot/94) lineage, and the fourth HA antigen is of the Eurasian avian-like $H1_{av}N1$ (EA) lineage.

[20] An immunogenic composition comprising first, second and third RNA replicon particles, the first RNA replicon particle comprising a nucleic acid construct, comprising first and second nucleic acid sequences encoding first and second hemagglutinin (HA) antigens of a Swine influenza A virus (IAV-S), wherein the first HA antigen is a of the A/swine/Gent/1/1984-like H3N2 (Gent/84) lineage, and the second HA antigen is of the A(H1N1)pdm09 (pdm09) lineage, the second RNA replicon particle comprising a nucleic acid construct comprising third and fourth nucleic acid sequences encoding third and fourth HA antigens of IAV-S, wherein the third HA antigen is of the A/swine/Scotland/410440/1994-like $H1_{hu}N2$ (Scot/94) lineage, and the fourth HA antigen is of the Eurasian avian-like $H1_{av}N1$ (EA) lineage, the third RNA replicon particle comprising a nucleic acid construct, comprising first, second and third nucleic acid sequences encoding first, second and third neuraminidase (NA) antigens of IAV-S, wherein the first NA antigen is of the A/swine/Scotland/410440/1994-like $H1_{hu}N2$ (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}N1$ (EA) lineage.

In a fourth aspect, the present invention provides the following embodiments:

[1] A nucleic acid construct for use in the prevention of a disease caused by a Swine influenza A virus in a subject, the nucleic acid construct comprising first, second and third nucleic acid sequences encoding first, second and third neuraminidase (NA) antigens of a Swine influenza A virus (IAV-S), wherein the first NA antigen is of the A/swine/Scotland/410440/1994-like $H1_{hu}N2$ (Scot/94) lineage, the second NA antigen is of the A/swine/Gent/1/1984-like H3N2 (Gent/84) lineage, and the third NA antigen is selected from the A(H1N1)pdm09 (pdm09) lineage or the Eurasian avian-like $H1_{av}N1$ (EA) lineage.

[2] The nucleic acid construct for use as defined in [1], wherein the first NA antigen is from strain A/swine/England/61470/2013 (H1N2).

[3] The nucleic acid construct for use as defined in [1] or [2], wherein the first NA antigen encoded by the first nucleic acid sequence comprises an amino acid sequence of SEQ ID NO: 15 or an amino acid sequence having at least 90% sequence identity thereof.

[4] The nucleic acid construct for use as defined in any one of [1] to [3], wherein the second NA antigen is from strain A/swine/Italy/248147-8/2015 (H3N2).

[5] The nucleic acid construct for use as defined in any one of [1] to [4], wherein the second NA antigen encoded by the second nucleic acid sequence comprises an amino acid sequence of SEQ ID NO: 18 or an amino acid sequence having at least 90% sequence identity thereof.

[6] The nucleic acid construct for use as defined in any one of [1] to [5], wherein the third NA antigen is from strain A/swine/England/373/2010 (H1N1) or A/swine/Italy/179057/2015 (H1N1).

[7] The nucleic acid construct for use as defined in any one of [1] to [6], wherein the third NA antigen is from strain A/swine/Italy/28762-3/2013 (H1N1).

[8] The nucleic acid construct for use as defined in any one of [1] to [7], wherein the third NA antigen encoded by the third nucleic acid sequence comprises an amino acid sequence of SEQ ID NO: 24 or an amino acid sequence having at least 90% sequence identity thereof.

[9] An RNA replicon particle comprising the nucleic acid construct as defined in any one of [1] to [8].

[10] The RNA replicon particle as defined in [9], which is an alphavirus RNA replicon particle.

[11] The RNA replicon particle as defined in [9] or [10], which is a Venezuelan Equine Encephalitis Virus (VEEV) alphavirus RNA replicon particle.

[12] An immunogenic composition comprising the RNA replicon particle as defined in any one of [9] to [11].

[13] An immunogenic composition, comprising first, second and third RNA replicon particles,

- the first RNA replicon particle comprising a nucleic acid construct, comprising first and second nucleic acid sequences encoding first and second hemagglutinin (HA) antigens of a Swine influenza A virus (IAV-S), wherein
  - the first HA antigen is of the A/swine/Gent/1/1984-like H3N2 (Gent/84) lineage, and
  - the second HA antigen is of the A(H1N1)pdm09 (pdm09) lineage,
- the second RNA replicon particle comprising a nucleic acid construct comprising third and fourth nucleic acid sequences encoding third and fourth HA antigens of IAV-S, wherein
  - the third HA antigen is of the A/swine/Scotland/410440/1994-like $H1_{hu}N2$ (Scot/94) lineage, and
  - the fourth HA antigen is of the Eurasian avian-like $H1_{av}N1$ (EA) lineage, and
- the third RNA replicon particle is the RNA replicon particle as defined in any one of [9] to [11].

[14] A vaccine comprising the immunogenic composition as defined in [12] or [13].

[15] The vaccine as defined in [14], which is a nonadjuvanted vaccine.

[16] The vaccine as defined in [14], which comprises an adjuvant selected from the group consisting of a biodegradable oil, an oil-in-water emulsion with 2.5-50% (v/v) mineral oil, and a biodegradable oil mixed with an oil-in-water emulsion with 2.5-50% (v/v) mineral oil.

[17] The vaccine as defined in any one of [14] to [16] for use in the prevention of a disease caused by a Swine influenza A virus in a subject.

[18] A method of immunizing a porcine against a swine influenza A virus, the method comprising administering to the porcine an immunologically effective amount of the vaccine as defined in any one of [14] to [16].

[19] A nucleic acid construct comprising first, second and third nucleic acid sequences encoding first, second and third neuraminidase (NA) antigens of a Swine influenza A virus (IAV-S), wherein

- the first NA antigen is of the A/swine/Scotland/410440/1994-like $H1_{hu}N2$ (Scot/94) lineage,
- the second NA antigen is of the A/swine/Gent/1/1984-like H3N2 (Gent/84) lineage, and
- the third NA antigen is selected from the A(H1N1)pdm09 (pdm09) lineage or the Eurasian avian-like $H1_{av}N1$ (EA) lineage.

The following examples serve to provide further appreciation of the invention but are not meant in any way to restrict the effective scope of the invention.

EXAMPLES

Materials and Methods

Preparation of Alphavirus RNA RP Vaccine

Generation of Single HA or NA Gene Replicon Particles (RPs).

The VEE replicon vectors designed to express haemagglutinin (HA) or neuraminidase (NA) genes were constructed as previously described [see, U.S. 9,441,247 B2; the contents of which are hereby incorporated herein by reference], with the following modifications. The TC-83-derived replicon vector "pVEK" [disclosed and described in U.S. 9,441,247 B2] was digested with restriction enzymes Ascl and Pad. A DNA plasmid containing the codon-optimized open reading frame sequence of HA or NA genes (Table 1a 1b) with 5'-flanking sequence (5'-GGCGCGCCGCACC-3') (SEQ ID NO: 25) and 3'-flanking sequence (5'-TTAATTAA-3'), was similarly digested with restriction enzymes Ascl and Pad. The synthetic gene cassette was then ligated into the digested pVEK vector, and the resulting clones were renamed "pVHV-respective RP code. The "pVHV" vector nomenclature was chosen to refer to pVEK-derived replicon vectors containing transgene cassettes cloned via the Ascl and Pad sites in the multiple cloning site of pVEK.

Production of TC-83 RNA replicon particles (RP) was conducted according to methods previously described [U.S. 9,441,247 B2 and U.S. Pat. No. 8,460,913 B2; the contents of which are hereby incorporated herein by reference]. Briefly, pVHV replicon vector DNA and helper DNA plasmids were linearized with Not1 restriction enzyme prior to in vitro transcription using MegaScript T7 RNA polymerase and cap analog (Promega, Madison, WI). Importantly, the helper RNAs used in the production lack the VEE subgenomic promoter sequence, as previously described [Kamrud et al., J Gen Virol. 91 (Pt 7):1723-1727 (2010)]. Purified RNA for the replicon and helper components were combined and mixed with a suspension of Vero cells, electroporated in 4 mm cuvettes, and returned to OptiPro SFM cell culture media (Thermo Fisher, Waltham, MA). Following overnight incubation, alphavirus RNA replicon particles were purified, formulated in phosphate buffered saline with 5% sucrose (w/v) and 1% swine serum, passed through a 0.22 micron membrane filter, and dispensed into aliquots for storage. Titer of functional RP was determined by immunofluorescence assay on infected Vero cell monolayers. Batches of RP were identified according to the gene encoded by the packaged replicon (Tables 1a&b).

Generation of Multi HA or NA Genes Replicon Particles (RPs).

The VEE replicon vectors used to express HA or NA genes were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes Ascl and Pad. For dual-gene HA and NA constructs, the selected open reading frame sequences were codon-optimized and synthesized with flanking AscI and PacI sites. Furthermore, the interstitial sequence between the two synthetic HA or NA open-reading frames consisted of 47 nucleotides of non-coding heterologous sequence, and a second copy of the native TC-83 subgenomic (sg)RNA promoter and 5' untranslated sgRNA region sequence. These dual-gene constructs were termed "pVDG" to differentiate them from the parental vector with a single sgRNA promoter sequence. In case of triple-gene NA constructs, the pVDG-based constructs containing two NA genes was further modified, as follows. A third selected NA open reading frame was codon optimized and synthesized with flanking PacI and SphI sites for directional cloning into the pVDG vector downstream of the two existing NA genes. The new synthetic construct also contained 50 nucleotides of heterologous non-coding sequence, and a third copy of the native TC-83 sgRNA promoter and 5' untranslated sgRNA region sequence to the 5' of the third NA gene sequence. The 3' region from the third NA gene sequence consisted of the 3' untranslated region of TC-83, until the corresponding SphI site of the parental pVDG vector. The triple-gene vectors were termed "pVTG" to differentiate them from related vectors pVEK, pVHV, and pVDG.

The selected sequences of HA (Table 1a: EUHA1-3, EUHA1-2, EUHA1-5, EUHA1-15, EUHA1-17, EUHA1-8, EUHA1-11 and HA3-4) or NA (Table 1b: EUNA1-2, EUN1-4, EUN2-6 and EUN2-7) genes from EXAMPLES 1 & 3 were used to synthesize the multi-HA or NA genes in the plasmid vector pVDG or pVTG, as described above.

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference]. Briefly, pVDG or pVTG replicon vector DNA and helper DNA plasmids were linearized with NotI restriction enzyme prior to in vitro transcription using MegaScript T7 RNA polymerase and cap analog. Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to serum-free culture media. Following overnight incubation, alphavirus RNA replicon particles were purified from the cells and media by passing the suspension through a depth filter, washing with phosphate buffered saline containing 5% sucrose (w/v), and finally eluting the retained RP with 200 mM $Na_2SO_4$+5% sucrose (w/v) buffer. Alternatively, the cells and media were centrifuged in the presence of prepared Cellufine Sulfate® resin, washed with phosphate buffered saline containing 5% sucrose (w/v), and eluted with 200 mM $Na_2SO_4$+5% sucrose (w/v) buffer. Eluted RP were passed through a 0.22 micron membrane filter, and dispensed into aliquots for storage. Titer of functional RP was determined by immunofluorescence assay on infected Vero cell monolayers.

The following replicon particles were constructed and used in the experiments:

TABLE 1a

RNA particles, HA source strains, lineages, clade and GenBank accession numbers (Accession#)

| RP code | RP donor strain | Lineage | Clade | Accession # |
|---|---|---|---|---|
| EUH1-1 | A/swine/Denmark/10802-1/2012(H1N2) | EurAsianAvian(EA) | 1C.2-like | AKC43997.1 |
| EUH1-2 | A/swine/Denmark/10-1048-2/2011(H1N1) | EurAsianAvian(EA) | 1C.2 | AKC43996.1 |
| EUH1-3 | A/swine/Italy/28762-3/2013(H1N1) | EurAsianAvian(EA) | 1C.2.1 | AKJ81667.1 |
| EUH1-4 | A/swine/France/29-120326/2012(H1N1) | EurAsianAvian(EA) | 1C.2.1 | AKJ82257.1 |
| EUH1-5 | A/swine/France/44-120070/2012(H1N1) | EurAsianAvian(EA) | 1C.2.1 | AIL24876.1 |
| EUH1-13 | A/swine/France/56-140048-2014(H1N1) | EurAsianAvian(EA) | 1C.2.1 | AJW32121.1 |
| EUH1-9 | A/swine/Moeglingen/IDT14859/2012(H1N2) | Pandemic 2009 (pdm09) | 1A.3.3.2 | AGG86840.1 |
| EUH1-11 | A/swine/England/373/2010(H1N1) | Pandemic 2009 (pdm09) | 1A.3.3.2 | AFR76205.1 |
| EUH1-12 | A/swine/Italy/290271/2009(H1N1) | Pandemic 2009 (pdm09) | 1A.3.3.2 | ADA70669.1 |
| EUH1-8 | A/swine/England/9953/2012(H1N2) | Scotland 1994-clade 1 (Scot94-1) | 1B.1.1 | AKJ81533.1 |
| EUH1-6 | A/swine/Italy/186822/2011(H1N2) | Scotland 1994-clade 2 (Scot94-2.2) | 1B.1.2.2 | AGR45140.1 |
| EUH1-17 | A/swine/Italy/3033-1/2015(H1N2) | Scotland 1994-clade 2 (Scot94-2.2) | 1B.1.2.2 | ALX30160.1 |
| EUH1-7 | A/swine/France/22-130212/2013(H1N2) | Scotland 1994-clade 3 (Scot94-2.3) | 1B.1.2.3 | AHI43247.1 |
| EUH1-15 | A/swine/France/35-140041/2014(H1N2) | Scotland 1994-clade 3 (Scot94-2.3) | 1B.1.2.3 | AIL24895.1 |
| EUH3-1 | A/swine/Netherlands/Ysselsteyn-CVI8864A/2012(H3N2) | Gent 1984 (Gent/84) | 3.1970.1 | AKJ83041.1 |
| EUH3-2 | A/swine/Belgium/Glabbeek-284/2012(H3N2) | Gent 1984 (Gent/84) | 3.1970.1 | AKJ82900.1 |
| EUH3-3 | A/swine/Spain/33936/2012(H3N2) | Gent 1984 (Gent/84) | 3.1970.1 | AKJ83006.1 |
| EUH3-4 | A/swine/Italy/240849/2015(H3N2) | Gent 1984 (Gent/84) | 3.1970.1 | ALX30415.1 |

TABLE 1b

| RNA particles, NA source strains, lineages and GenBank accession number (Accession#) | | | |
|---|---|---|---|
| RP code | RP donor strain | Lineage | Accession # |
| EUN1-2 | A/swine/Italy/28762-3/2013(H1N1) | EA | AKJ81669.1 |
| EUN1-3 | A/swine/Denmark/101048-2/2011(H1N1) | EA | AKC43999.1 |
| EUN1-1 | A/swine/England/373/2010(H1N1) | Pdm09 | AFR76207.1 |
| EUN1-4 | A/swine/Italy/179057/2015(H1N1) | Pdm09 | ALX30323.1 |
| EUN2-1 | A/swine/Denmark/10801-2/2012(H1N2) | Scot94 | AKC44047.1 |
| EUN2-3 | A/swine/England/9953/2012(H1N2) | Scot94 | AKJ81535.1 |
| EUN2-5 | A/swine/Italy/246087/2014(H1N2) | Scot94 | ALX29925.1 |
| EUN2-6 | A/swine/England/61470/2013(H1N2) | Scot94 | AKJ82042.1 |

TABLE 1b-continued

| RNA particles, NA source strains, lineages and GenBank accession number (Accession#) | | | |
|---|---|---|---|
| RP code | RP donor strain | Lineage | Accession # |
| EUN2-2 | A/swine/Netherlands/Ysselsteyn-CVI8864A/2012(H3N2) | Gent84 | AKJ83043.1 |
| EUN2-7 | A/swine/Italy/248147-8/2015(H3N2) | Gent84 | ALX30429.1 |

Note:
Clade information is not available for NA antigens

If not indicated otherwise in the Examples or Figures, the following strains and lineages have been used for HI assays:

TABLE 1c

| SIV strains used as HA antigen source for HI assays in FIGS. 1, 2, 3 and 4 | | | | |
|---|---|---|---|---|
| # | SIV strain | Abbrevation | Lineage | Accession # |
| 1 | A/swine/Denmark/10630-1/2009 (H1N2) | Den10630 (EA) | EA | AKC43951.1 |
| 2 | A/swine/France/Morbihan-0213/2011 (H1N2) | Fr0213 (EA) | EA | AKJ80535.1 |
| 3 | A/swine/France/70-130144/2013 (H1N1) | Fra130144 (EA) | EA | AIL24884 |
| 4 | A/swine/France/41-120137/2012 (H1N1) | Fr120137(EA) | EA | AIL24877.1 |
| 5 | A/swine/France/50-130337/2013 (H1N1) | Fr130337 (EA) | EA | AIL24889.1 |
| 6 | A/swine/France/53-130065/2013 (H1N1) | Fr130065 (EA)-C | EA | AGL07471.1 |
| 7 | A/swine/Morbihan/0070/2005 (H1N1) | Fr0070 (EA) | EA | Not available |
| 8 | A/swine/Italy/280201/2013 (H1N1) | It280201 (EA) | EA | ALX29477.1 |
| 9 | A/swine/Deventer/1/2012 (H1N1) | GD-H1 (EA) | EA | Not available |
| 10 | A/swine/England/041118/2013 (H1N2) | Eng41118 (Scot1)-C | Scot94-1 | AKJ81500.1 |
| 11 | A/swine/Italy/114922/2014 (H1N2) | It114922 (Scot2) | Scot94-2 | ALX29748.1 |
| 12 | A/swine/Italy/41350/2011 (H1N2) | It41350(Scot2)-C | Scot94-2 | AKJ80629.1 |
| 13 | A/swine/Italy/57680/2011 (H1N2) | It57680 (Scot3) | Scot94-3 | AKJ80640.1 |
| 14 | A/swine/France/22-130212/2013 (H1N2) | Fr130212 (Scot2)-C | Scot94-2 | AHI43247.1 |
| 15 | A/swine/Scotland/410440/94 (H1N2) | Scot1994 (Scot2) | Scot94-2 | Not available |
| 16 | A/swine/Gent/7625/1999 (H1N2) | GD-H1 (Scot3) | Scot94-3 | AZQ96426.1 |
| 17 | A/swine/Italy/124953/2014 (H1N2) | It24953 (pdm)-C | Pdm09 | ALX29759.1 |
| 18 | A/swine/Italy/6352-17/13 (H1N1) | It6352-17 (pdm) | Pdm09 | AIC64646.1 |
| 19 | A/swine/Italy/23721/2015 (H1N1) | It23721 (pdm) | Pdm09 | ALX30205.1 |
| 20 | A/swine/MN/A01483170/2014 (H1N1) | MN (pdm)-C | Pdm09 | AIX94905.1 |
| 21 | A/swine/Belgium/Gent-1/1984 (H3N2) | Gent-1984 (Gent) | Gent84 | AKJ82853.1 |
| 22 | A/swine/Belgium/Belsele-66/2013 (H3N2) | Belsele66 (Gent) | Gent84 | AKJ82983.1 |
| 23 | A/swine/Belgium/113/2013 (H3N2) | Bel113 (Gent)-C | Gent84 | AKJ82888.1 |
| 24 | A/swine/Flanders/1/1998 (H3N2) | GD-H3 (Gent) | Gent84 | ACN98096.1 |

TABLE 1d

| SIV strains used as HA antigen source for HI assays in FIGS. 5 and 6 | | |
|---|---|---|
| # | Strain name | HA Lineage |
| 1 | A/swine/France/53-130065/2013 (H1N1) | EA |
| 2 | A/swine/Belgium/113/2013 (H3N2) | Gent/84 |
| 3 | A/swine/MN/A01483170/2014 (H1N1) | pdm09 |
| 4 | A/swine/England/041118/2013 (H1N2) | Scot94-1 |
| 5 | A/swine/France/22-130212/2013 (H1N2) | Scotland 1994-2 (Scot94-2) |

TABLE 1e

| SIV strain or expressed NA antigen source for NI assays in FIGS. 7, 8, 9 and 10 | | | | |
|---|---|---|---|---|
| # | SIV strain or expressed NA protein | Abbrevation | Lineage | Accession # |
| 1 | A/swine/Denmark/10630-1/2009 (H1N2) | Den10630 (EA) | EA | AKC44059.1 |
| 2 | A/swine/France/Morbihan-0213/2011 (H1N2) | Fr0213 (EA) | EA | AKJ80537.1 |
| 3 | A/swine/France/70-130144/2013 (H1N1) | Fra130144 (EA) | EA | Not available |
| 4 | A/swine/France/41-120137/2012 (H1N1) | Fr120137(EA) | EA | Not available |
| 5 | A/swine/France/50-130337/2013 (H1N1) | Fr130337 (EA) | EA | Not available |
| 6 | A/swine/France/53-130065/2013 (H1N1) | Fr130065 (EA)-C | EA | AGL07474.1 |

TABLE 1e-continued

SIV strain or expressed NA antigen source for NI assays in FIGS. 7, 8, 9 and 10

| # | SIV strain or expressed NA protein | Abbrevation | Lineage | Accession # |
|---|---|---|---|---|
| 7 | A/swine/Morbihan/0070/2005 (H1N1) | Fr0070 (EA) | EA | Not available |
| 8 | A/swine/Italy/280201/2013 (H1N1) | It280201 (EA) | EA | ALX29479.1 |
| 9 | A/swine/Deventer/1/2012 (H1N1) | GD-H1 (EA) | EA | Not available |
| 10 | A/swine/Italy/28762-3/2013 (H1N1) | It28762-3 (EA) EUN1-2* | EA | AKJ81669.1 |
| 11 | A/swine/Denmark/101048-2/2011 (H1N1) | Den1011048 (EA) EUN1-3* | EA | AKC43999.1 |
| 12 | A/swine/England/041118/2013 (H1N2) | Eng41118 (Scot)-C | Scot94 | AKJ81502.1 |
| 13 | A/swine/Italy/114922/2014 (H1N2) | It114922 (Scot) | Scot94 | ALX29750.1 |
| 14 | A/swine/Italy/41350/2011 (H1N2) | It41350(Scot)-C | Scot94 | AFU09071.1 |
| 15 | A/swine/Italy/57680/2011 (H1N2) | It57680 (Scot) | Scot94 | AKJ80642.1 |
| 16 | A/swine/France/22-130212/2013 (H1N2) | Fr130212 (Scot)-C | Scot94 | AHI43225.1 |
| 17 | A/swine/Scotland/410440/94 (H1N2) | Scot1994 (Scot) | Scot94 | CAC86322.1 |
| 18 | A/swine/Gent/7625/1999 (H1N2) | GD-H1 (Scot) | Scot94 | AZQ96428.1 |
| 19 | A/swine/Italy/246087/2014 (H1N2) | It246087 (Scot) EUN2-5* | Scot94 | ALX29925.1 |
| 20 | A/swine/England/61470/2013 (H1N2) | Eng61470 (Scot) EUN2-6* | Scot94 | AKJ82042.1 |
| 21 | A/swine/Italy/124953/2014 (H1N2) | It124953 (Scot)-C | Scot94 | ALX29761.1 |
| 22 | A/swine/Italy/6352-17/13 (H1N1) | It6352-17 (pdm) | pdm09 | AIC64648.1 |
| 23 | A/swine/Italy/23721/2015 (H1N1) | It23721 (pdm) | pdm09 | ALX30207.1 |
| 24 | A/swine/MN/A01483170/2014 (H1N1) | MN (pdm)-C | pdm09 | AIX94908.1 |
| 25 | A/swine/Italy/179057/2015 (H1N1) | It179057 (pdm) EUN1-4* | pdm09 | ALX30323.1 |
| 26 | A/swine/Belgium/Gent-1/1984 (H3N2) | Gent-1984 (Gent) | Gent84 | Not available |
| 27 | A/swine/Belgium/Belsele-66/2013 (H3N2) | Belsele66 (Gent) | Gent84 | AKJ82985.1 |
| 28 | A/swine/Belgium/113/2013 (H3N2) | Bel113 (Gent)-C | Gent84 | AKJ82890.1 |
| 29 | A/swine/Flanders/1/1998 (H3N2) | GD-H3 (Gent) | Gent84 | Not available |
| 30 | A/swine/Italy/248147-8/2015 (H3N2) | It248147 (Gent) EUN2-7* | Gent84 | ALX30429.1 |
| 31 | A/swine/Netherlands/Ysselsteyn-CVI8864A/2012 (H3N2) | CVI8864A (Gent) EUN2-2* | Gent84 | AKJ83043.1 |

*Lysates of vero cells expressing respective NA antigen was used as source of NA antigen TABLE 1f NA antigen source for NI assays in FIGS. 11 and 12

| # | NA donor strain | Abbrevation | Lineage | Accession # |
|---|---|---|---|---|
| 1 | A/swine/Italy/28762-3/2013 (H1N1) | It28762-3 (EA) EUN1-2* | EA | AKJ81669.1 |
| | A/swine/Italy/179057/2015 (H1N1) | It179057 (pdm) EUN1-4* | pdm09 | ALX30323.1 |
| 4 | A/swine/England/61470/2013 (H1N2) | Eng61470 (Scot) EUN2-6* | Scot94 | AKJ82042.1 |
| 6 | A/swine/Italy/248147-8/2015 (H3N2) | It248147 (Gent) EUN2-7* | Gent84 | ALX30429.1 |

*Lysates of vero cells expressing respective NA antigen was used as source of NA antigen General Study Design Approximately, five weeks old healthy pigs (3 pigs per vaccine) that were seronegative or had low antibodies against SIV were vaccinated intramuscularly with 5-10×10$^6$ RNA particle vaccines encoding either single or multiple HA or NA genes with Xsolve50 adjuvant per pig per time. The respective vaccination was repeated at approximately 8 weeks of age and the blood samples were collected approximately 9 weeks of age and were used for either Hemagglutination inhibition (HI) assay or Neuraminidase inhibition (NI) assays to quantify the levels of antigen specific antibody levels.

Hemagglutination Inhibition (HI) Assay:

All serum samples were heat inactivated at 56° C. for 30 min, subsequently treated with 0.25% periodate, followed by 0.75% glycerol and adsorbed with 2.6% chicken red blood cells to remove non specific agglutinins. For HI antibody titration, serial dilutions of pre-treated serum were incubated for 1 hour with 8 hemagglutination units of SIV strains listed in table 1c or 1d as HA antigens. Subsequently, the mixture was incubated with 0.2% chicken red blood cells for 1 hour at room temperature and plates were read for inhibition of agglutination. The reciprocal of the highest serum dilution that completely inhibited erythrocyte agglutination was assigned as the HI titer and expressed in log base 2 values.

Serum Neuraminidase (NA) Inhibition (NI) Assay:

SIV strains of lysates of Vero cell expressing NA antigens electroporating the with replicon RNA encoding genes for respective NA (Tables 1e and 1f) were used as source of NA antigens. Enzymatic activity of those NA was quantified by sialic acid cleavage from fetuin on 96-well plates during an overnight incubation at 37° C. Peanut agglutinin-horseradish peroxidase conjugate (PNA-HRP) was then added for 2 h at room temperature, binding to fetuin molecules stripped of sialic acid. Signal was obtained with 3,3',5,5'-Tetramethylbenzidine (TMB) substrate and read at 450 nm. Test antigens were titrated to determine the dilution that is able to yield 70% of the maximum signal. Equal volumes of NA antigen were added to serial dilutions of serum in fetuin-coated wells during the overnight 37° C. incubation. Optical density (OD) values were normalized to the values from positive control wells containing no serum. Neuraminidase inhibition titers were defined as the reciprocal of the interpolated serum dilution having an extinction value equal to 50% inhibition in comparison with the control and were expressed in log base 2 values.

The correlation of neuraminidase and hemagglutinin antibody titers with vaccine-induced protection against SIV-A is described in: [Hobson D. et al., J Hyg (Lond) 70, 767-777 (1972); Ohmit S E, et al., J. Infect. Dis 204, 1879-1885 (2011); Walz L, et al., J Virol. 2018; 92(17):e01006-18. (2018). Thus, the serology results in the Hi and Ni inhibition assays described in the following Examples are indicative of the prevention of disease caused by SIV-A.

Example 1: Hemagglutination Inhibition (HI) Antibody Titers Induced by RP Encoding Single HA Antigens In order to determine protection and cross-protection of alphavirus RNA RP encoding single HA antigens of each of the strains EurAsianAvian (EA), Gent/84, Scot/94 and pdm09 the following study was carried out:

Five weeks old pigs (3 per group) were vaccinated with respective RNA particle with XSolve50 adjuvant in a prime-boost regimen with approximately 3 weeks interval. Sera were collected one to two weeks post booster vaccination to determine influenza antigen specific hemagglutination inhibition antibody titers, a correlate of protection against influenza. The HI assay measures the highest dilution of serum that prevents influenza virus-induced hemagglutination of erythrocytes. The reciprocal of this dilution was defined as the HI titer in Log 2 base. The reported values are average of 3 animals. The detection limit for this assay is 4 (dotted line in the figures) and hence the titer below 4 are reported as 3 in the figures.

The results of HI experiments are shown in FIGS. 1-4. The following conclusions could be drawn:

- FIG. 1: RPs of strain EUHA1-3 of the EA lineage showed highest antigen specific HI antibody titers against nearly all tested EA antigens of IAS followed by EUH1-5 and EUH1-2. In addition, cross reactive titers against some Scot/94 and pdm09 HA antigens could be observed. None of the tested strains showed any cross-reactive titers against Gent/84 IAS antigens (all HI titers below 4).
- FIG. 2: RPs of strain EUHA1-15 showed highest antigen specific HI antibody titers against nearly all tested Scot/94 antigens followed by EUH1-17, and thus performed best for Scot/94 antigens of clade 2 and 3. RPs of strain EUHA1-8 showed highest antigen specific HI antibody titers against tested Scot/94 antigens of clade 1. In addition, cross reactive titers against some EA and pdm09 HA IAS antigens could be observed. None of the tested strains showed any cross-reactive titers against Gent/84 IAS antigens (all HI titers below 4).
- FIG. 3: RPs of strain EUHA1-11 of the Pdm09 lineage showed highest antigen specific HI antibody titers against nearly all pdm09 antigens. In addition, cross reactive titers against most EA and Scot/94HA antigens could be observed. None of the tested strains showed any cross-reactive titers against Gent/84 IAS antigens (all HI titers below 4).
- FIG. 4: RPs of strain EUHA3-4 of the Gent/84 lineage showed highest antigen specific HI antibody titers against all tested Gent/84 antigens. No significant cross-reactive titers against HA antigens of EA, Scot/94 and pdm09 antigens could be observed.

Example 2: Hemagglutination Inhibition (HI) Antibody Titers Induced by RP Encoding Dual-HA Antigens In order to determine serological efficacy of alphavirus RNA RP encoding dual-e HA antigens combining 1) HA antigens of pdm09 and Gent/84 lineage or
2) HA antigens of EA and Scot/94 antigens, a study with a design as described in Example 1 was carried out.

The results of HI assay are shown in FIG. 5. The following conclusions could be drawn:

It could be observed that not all combinations tested induce a strong serological response. In addition, it could surprisingly be observed that the order of the genes in the viral genome of the replicon particle is critical in inducing a serological response.

- Combination of HA antigens of lineages Pdm09 and Gent/84: Only the combination with Gent/84 placed first and pdm09 placed second in the viral genome of the replicon particle induced a strong serological response. Instead, in the order of Pdm09 placed first and Gent/84 placed second in the viral genome of the replicon particle only a much lower serological response against Gent/84 HA antigens and a very weak serological response against Pdm09 HA antigens could be observed.
- Combination of HA antigens of lineages EA and Scot/94: Not all combinations tested induced a strong serological response. The combination of strains EUHA1-17 of Scot/94 and EUHA1-3 of EA showed the best serological response (highest HI titers against IAS antigens of both lineages).
- In addition, only the combination with Scot/94 placed first and EA placed second in the replicon RNA of the replicon particle induced a strong serological response. Instead, in the order of EA placed first and Scot/94 placed second in the replicon RNA of the replicon particle no significant serological response against EA HA antigens could be observed.
- Among various combinations tested, the combination of EUHA3-4+EUHA1-11 and EUHA1-17+EUHA1-3 strains induce the best immunity measured as HI titer. Thus, these combinations are beneficially used in a formulation combining the two replicon particles, i.e. for combining a first RNA replicon particle encoding, in this order, EUHA3-4+EUHA1-11 strains with a second RNA replicon particle encoding, in this order, EUHA1-17+EUHA1-3 strains.

In consequence, it could surprisingly be demonstrated that the position of the HA gene within the RNA replicon particle and/or the specific combination of HA antigens determines the level of induced immunity measured as HI titer.

Example 3: Neuraminidase Inhibition (NI) Antibody Titers Induced by RP Encoding Single NA Antigens In order to determine serological efficacy of alphavirus RNA RP encoding single NA antigens of each of the strains EurAsianAvian (EA), Gent/84, Scot/94 and pdm09 the following study was carried out:

Five weeks old pigs (3 per group) were vaccinated with respective RNA replicon particle with XSolve50 adjuvant in a prime-boost regimen with approximately 3 weeks interval. Sera were collected one to two weeks post booster vaccination to determine influenza antigen specific neuraminidase inhibition (NI) antibody titers. NI titers were measured using the lectin (peanut agglutinin)-based assay as described above, the reciprocal of the highest dilution of serum that inhibits NA activity at least 50% compared to control wells was defined as the NI titer. The detection limit for this assay was 2 (dotted line in the figure).

The results of NI experiments are shown in FIGS. 7-10. The following conclusions could be drawn:

FIG. 7: RPs of strain EUNA1-2 of the EA lineage showed highest antigen specific NI antibody titers against nearly all tested EA antigens of IAS. In addition, cross reaction against some Scot/94, pdm09 and Gent/84 NA antigens could be observed.

FIG. 8: RPs of strain EUNA1-4 showed highest antigen specific NI antibody titers against most tested pdm09 antigens, although level of NI titers observed was lower compared to NI titers achieved with RPs of the EA lineage. In addition, cross reactive titer against EA, Scot/94 and Gent/84 NA IAS antigens could be observed. Differences in the titers measured between the tested strains were low.

FIG. 9: RPs of strain EUNA2-6 of the Scot/94 lineage showed highest antigen specific NI antibody titers against all tested Scot/94 antigens. In addition, a high level of cross reactivity against EA, pdm09 and Gent/84 NA antigens could be observed for strain EUNA2-6.

FIG. 10: RPs of strain EUNA2-7 of the Gent/84 lineage showed high antigen specific NI antibody titers against all tested Gent/84 antigens and also showed significant cross-protection against NA antigens of EA, Scot/94 and pdm09 antigens.

Example 4: NI Antibody Titers Induced by RP Encoding Dual- or Triple NA Antigens In order to determine serological efficacy of alphavirus RNA RP encoding dual- or triple NA antigens, RP encoding NA antigens from below listed lineages were designed and produced 1) NA antigens of EA and Gent/84 lineage or 2) NA antigens of EA, Gent/84 and Scot/94 antigens, a study with a design as described in Example 3 was carried out.

The results of NI experiments are shown in FIG. 11. The following conclusions could be drawn:

It could be shown that all combinations tested induce a serological response irrespective of the order of the gene. Thus, it could surprisingly be observed that contrary to the observations with the HA antigens (see Example 2 above), the order of the NA genes in the viral genome of the replicon particle is not critical for inducing a serological response.

Example 5: NI Antibody Titers Induced by RP Encoding Dual- and Triple-NA Antigens The results shown in FIGS. 7 to 10 reveal that a combination of a strain of the EA lineage, the Gent/84 lineage with strain of the Scot/94 lineage should provide the best protection against IAS having the best protection and cross protection against all four lineages. The best candidate to test such cross-protection is thus a combination of strain EUNA2-6 of the Scot/94 lineage with EUNA2-7 of the Gent/84 lineage, which may then further be combined with strains of either the EA lineage, such as strain EUNA1-2 or the pdm09 lineage, such as strain EUNA1-4. In consequence, these combinations of strains were tested for their serological response.

Thus, in order to determine protection of alphavirus RNA RP encoding dual- and triple-NA antigens combining 1) NA antigens of EA and Gent/84 lineage 2) NA antigens of Scot/94, Gent/84 and EA antigens or 3) NA antigens of Scot/94, Gent/84 and pdm09 antigens, a study with a design as described in Example 3 was carried out.

The results are shown in FIG. 12:

Contrary to the results observed for the HA antigens, the combination of NA antigens from only three lineages is sufficient to induce a serological response against all four IAS lineages.

Weak serological response against all four IAS lineages could already be achieved with the combination of NA antigens from only two lineages, irrespective of the order of gene in the RNA replicon particle.

Highest serological response could be achieved with a combination of Scot/94 and Gent/84 NA antigens further combined with either NA antigens of the pdm09 or the EA lineage.

TABLE 2

| List of SEQ ID NOs | | |
|---|---|---|
| SEQ ID NO # | Accession No., Donor strain; RP code | Sequence |
| 1 | >KU323133.1 Influenza A virus (A/swine/Italy/3033-1/2015(H1N2)) segment 4 hemagglutinin (HA) gene, complete cds | Nucleotide, native sequence |
| 2 | >EUH1-17 Swine optimized sequence for EUSIV-T8-RP production | Nucleotide, Codon optimized |
| 3 | >ALX30160.1 hemagglutinin [Influenza A virus (A/swine/Italy/3033-1/2015(H1N2))] EUH1-17 | Amino acid, native sequence |
| 4 | >KR700530.1 Influenza A virus (A/swine/Italy/28762-3/2013(H1N1)) segment 4 hemagglutinin (HA) gene, complete cds | Nucleotide, native sequence |
| 5 | >EUH1-3 Swine optimized sequence for EUSIV-T8-RP production | Nucleotide, Codon optimized |
| 6 | >AKJ81667.1 hemagglutinin [Influenza A virus (A/swine/Italy/28762-3/2013(H1N1))] EUH1-3 | Amino acid, native sequence |
| 7 | >KU323308.1 Influenza A virus (A/swine/Italy/240849/2015(H3N2)) segment 4 hemagglutinin (HA) gene, complete cds | Nucleotide, native sequence |
| 8 | >EUH3-4 Swine optimized sequence and used in EUSIV-K | Nucleotide, Codon optimized |
| 9 | >ALX30415.1 hemagglutinin [Influenza A virus (A/swine/Italy/240849/2015(H3N2))] EUH3-4 | Amino acid, native sequence |
| 10 | >CY116127.1 Influenza A virus (A/swine/England/373/2010(H1N1)) hemagglutinin (HA) gene, complete cds | Nucleotide, native sequence |

TABLE 2-continued

List of SEQ ID NOs

| SEQ ID NO # | Accession No., Donor strain; RP code | Sequence |
|---|---|---|
| 11 | >EUH1-11 Swine optimized sequence for EUSIV-K | Nucleotide, Codon optimized |
| 12 | >AFR76205.1 hemagglutinin [Influenza A virus (A/swine/England/373/2010(H1N1) EUH1-11 | Amino acid, native sequence |
| 13 | >KR700793.1 Influenza A virus (A/swine/England/61470/2013(H1N2)) segment 6 neuraminidase (NA) gene, complete cds | Nucleotide, native sequence |
| 14 | >EUN2-6 Swine optimized sequence for EUSIV-R | Nucleotide, Codon optimized |
| 15 | >AKJ82042.1 neuraminidase [Influenza A virus (A/swine/England/61470/2013(H1N2))] EUN2-6 | Amino acid, native sequence |
| 16 | >KU323318.1 Influenza A virus (A/swine/Italy/248147-8/2015(H3N2)) segment 6 neuraminidase (NA) gene, complete cds | Nucleotide, native sequence |
| 17 | >EUN2-7 Swine optimized sequence for EUSIV-R | Nucleotide, Codon optimized |
| 18 | >ALX30429.1 neuraminidase [Influenza A virus (A/swine/Italy/248147-8/2015(H3N2))] EUN2-7 | Amino acid, native sequence |
| 19 | >KU323247.1 Influenza A virus (A/swine/Italy/179057/2015(H1N1)) segment 6 neuraminidase (NA) gene, complete cds | Nucleotide, native sequence |
| 20 | >EUN1-4 Swine optimized sequence for EUSIV-R | Nucleotide, Codon optimized |
| 21 | >ALX30323.1 neuraminidase [Influenza A virus (A/swine/Italy/179057/2015(H1N1))] EUN1-4 | Amino acid, native sequence |
| 22 | >KR700532.1 Influenza A virus (A/swine/Italy/28762-3/2013(H1N1)) segment 6 neuraminidase (NA) gene, complete cds | Nucleotide, native sequence |
| 23 | >EUN1-2 Swine optimized sequence for EUSIV-R | Nucleotide, Codon optimized |
| 24 | >AKJ81669.1 neuraminidase [Influenza A virus (A/swine/Italy/28762-3/2013(HIN1))] EUN1-2 | Amino acid, native sequence |

Example 6: Evaluation of Vaccine Efficacy of a Multivalent IAV-S Vaccine

A study was undertaken to determine the immunogenicity and efficacy of a multivalent IAV-S vaccine comprising two-dual-HA RPs (EUSIV-T8 RP encoding EUHA1-17 & EUHA1-3 antigens and EUSIV-K RP encoding EUH3-4 & EUH1-11 antigens, Tables 1a & 2) and one-triple-NA construct (EUSIV-R encoding EUN2-6, EUN1-2 & EUN2-5 antigens, Tables 1b & 2). The adjuvanted vaccine was administered to 5 pigs in two-intramuscular (IM) vaccinations at 5 and 8 weeks of age (2 mL per dose; $3\times5\times10^6$ RP/dose, Vaccinates). Equal number of non-vaccinates received adjuvanted phosphate buffered saline. Immunogenicity of the vaccine was measured by quantifying HI and NI titers in sera samples collected prior to experimental infection at 10 weeks of age. The efficacy of the vaccine was tested against Gent/84 [A/swine/Belgium/113/2013 (H3N2)] challenge infection via intratracheal route at 10 weeks of age (study day 32). Vaccine efficacy against IAV-S infection induced fever i.e., raise in rectal temperature and lung lesions at 3 days post infection were measured.

Figure 13D:
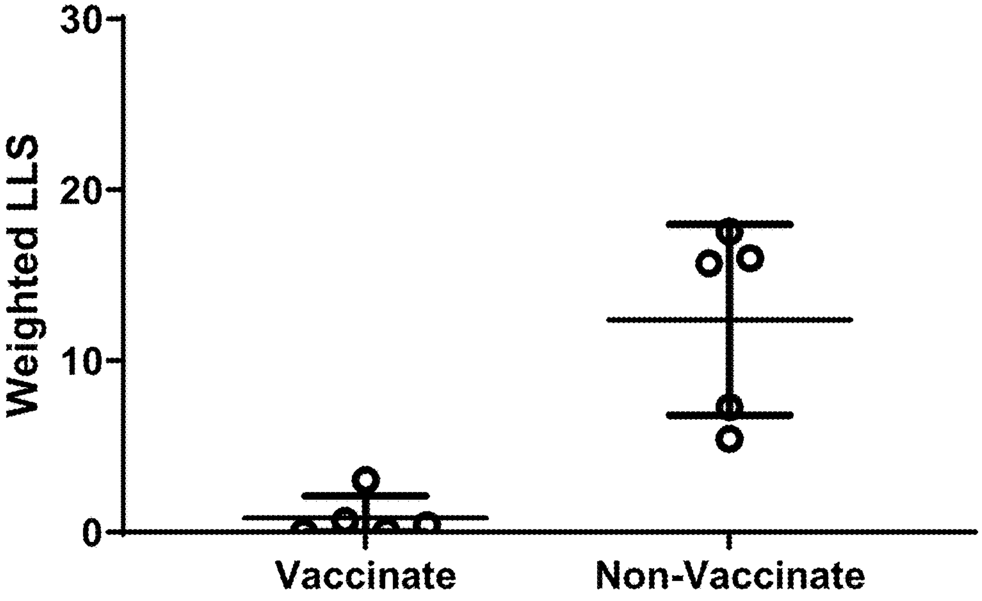

The results of this experiment are shown in FIGS. 13A, 13B, 13C and 13D. Multivalent IAV-S vaccine induced functional HI titers against heterologous IAV-S strains belonging to all four lineages (FIG. 13A) and NI titers against homologous NA antigen of all three lineages (FIG. 13B). Furthermore, multivalent IAV-S vaccine protected pigs from the experimental infection induced raise in rectal temperature, fever (FIG. 13C) and the lesions in pigs (FIG. 13D). These results demonstrate that the tested multivalent IAV-S was both immunogenic and efficacious.

Example 7: Evaluation of Vaccine Efficacy after ID Administration

A study was undertaken to determine the serological efficacy of a multivalent IAV-S vaccine comprising two-dual-HA RPs (EUSIV-T8 RP encoding EUHA1-17 & EUHA1-3 antigens and EUSIV-K RP encoding EUH3-4 & EUH1-11 antigens, Tables 1a & 2) and one-triple-NA construct (EUSIV-R encoding EUN2-6, EUN1-2 & EUN2-5 antigens, Tables 1b & 2). The adjuvanted vaccine was administered to 3 pigs in two-intradermal (ID) vaccinations using IDAL® needle free injector at 5 and 8 weeks of age (200 uL per dose; $3\times3\times10^6$ RP/dose, Vaccinates). Equal number of non-vaccinates received adjuvanted phosphate buffered saline. Immunogenicity of the vaccine was measured by quantifying HI and NI titers in sera samples collected at 10 weeks of age.

The results of this experiment are shown in FIGS. 14A and 14B. Multivalent IAV-S vaccine induced functional HI titers against heterologous IAV-S strains belonging to three out of four lineages tested (FIG. 14A) and NI titers against two out of three homologous NA antigens tested (FIG. 14B). These results demonstrate that the intradermal application of multivalent IAV-S vaccine also efficacious.

The invention claimed is:

1. An RNA replicon particle comprising a nucleic acid construct that comprises a first nucleic acid sequence, a second nucleic acid sequence, and a third nucleic acid sequence, each encoding a neuraminidase (NA) antigen of a Swine influenza A virus (IAV-S), wherein (i) the first nucleic acid sequence encodes an NA antigen of the A/swine/Scotland/410440/1994-like $H1_{hu}N2$ (Scot/94) lineage, (ii) the second nucleic acid sequence encodes an NA antigen of the A/swine/Gent/1/1984-like H3N2 (Gent/84) lineage, and (iii) the third nucleic acid sequence encodes an NA antigen is selected from the group consisting of the A(H1N1)pdm09 (pdm09) lineage and the Eurasian avian-like $H1_{av}N1$ (EA) lineage.

2. The RNA replicon particle of claim 1, which is an alphavirus RNA replicon particle.

3. The RNA replicon particle of claim 2, which is a Venezuelan Equine Encephalitis Virus (VEEV) alphavirus RNA replicon particle.

4. An immunogenic composition comprising the RNA replicon particle of claim 3.

5. A method of immunizing a porcine against a swine influenza A virus, comprising administering to the porcine an immunologically effective amount of the immunogenic composition of claim 4.

* * * * *

SEQUENCE LISTING

```
<160> NUMBER OF SEQ ID NOS: 25

<210> SEQ ID NO 1
<211> LENGTH: 1695
<212> TYPE: DNA
```

<213> ORGANISM: Influenza A virus
<220> FEATURE:
<223> OTHER INFORMATION: >KU323133.1 Influenza A virus (A/swine/Italy/
3033-1/2015(H1N2)) segment 4 hemagglutinin (HA) gene, complete cds

<400> SEQUENCE: 1
atgaaagcta aactactaat cctgttgtgt gcactttcaa ctacagatgc agacacaata 60
tgtataggat accatgctaa caattcaacc gacaccgttg acacagtcct agaaaagaat 120
gtgacagtaa cacactctgt caacctcctt gaggacagtc acaatgggaa actatgtaaa 180
ctgaagggag tggccccact gcaattggga aaatgcagca tcgcaggatg gatactaggg 240
aacccagagt gtgaatcact gctttctaag aaatcatggt cctatattgc agaagcacca 300
aatgctgaga atggaatatg ttacccaggg cacttctccg actacgaaga gctgagggag 360
caattaagtt cagtatcttc attcgagagg ttcgaaatat ttcctaagga gagttcatgg 420
cccaaacaca gcataggagc aactgcatca tgctccaaac aagggaaaag cagtttttat 480
acaaatctgc tatggctaac tgaaaaaaat gggtcttatc caaatttgac catgtcctat 540
atgaacgaca aagagagaga agtccttgtg ctatggggag tccatcatcc gtccaacata 600
gaggaccaaa gagcaatcta tcgcaaagaa actgcttatg tttctgtaat gtcatcacac 660
tacaacaaga ggttcacccc agagattgca aaaagaccca aagtaaggaa tcaagagggg 720
agaatcaact actactggac actgctggaa cccagggaca caataatatt tgaagcaaat 780
gggaatttga tagcaccatg gtatgctttt gcattgaata gaggctttga gtcaggaatc 840
attgtctcaa atgcatcgat ggatgagtgt aacgcgaagt gtcaaacgcc ccgaggagcg 900
ataaacaata gcctgccttt ccagaatgta cacccaatca caatagggga atgccccaag 960
tatgtaaaga gtacaaaatt aaagatggct acaggactta gaaacattcc atccatccaa 1020
tccagaggtt tgtttggagc cattgctggt ttcattgaag gggatggac cggaatgata 1080 gatggatggt atggttatca tcatcagaat gaacagggtt ctggctatgc tgcagatcaa 1140
aaaagcacac aaaatgccat taatgggatt acaaacaagg tgaactctgt tatcgataaa 1200
atgaacactc aatttacagc tgtaggtaaa gaattcaaca gattagaaaa aagaatggaa 1260
aacctgaata agaaggttga tgacggtttt cttgacattt ggacgtataa tgcagaattg 1320
ttggttctgc tggagaatga gaggactttg gattttcatg attcaaatgt gaagagctta 1380
tatgaaggag taaaggccca attgaagaat aatgccaaag aagtaggaaa cgggtgtttt 1440
gaattctacc acaagtgtga caacgaatgc atggacagtg taaaaaatgg aacttatgac 1500
tatccaagat actcagagga atcaaaatta aacagagaac aaattgatgg agtggaattg 1560
aaatcaatgg gagtctatca gatcctggcg atatactcaa ctgccgccag ttcattggtg 1620
cttttagtca ccctgggggc aatcagtttt tggatgtgtt ctaatggttc tttgcagtgc 1680
agaatatgta tctga 1695

<210> SEQ ID NO 2
<211> LENGTH: 1695
<212> TYPE: DNA
<213> ORGANISM: Artificial Sequence
<220> FEATURE:
<223> OTHER INFORMATION: >EUH1-17 Swine optimized sequence

<400> SEQUENCE: 2
atgaaagcca agctcctcat tctcctttgt gccctgtcca cgaccgacgc tgatactatc 60
tgcatcggct accatgccaa caactccact gataccgtgg acaccgtgct ggaaaagaac 120

```
gtgaccgtga ctcactcggt gaacctcctt gaggacagcc acaacgggaa gctctgcaag    180

ctgaagggcg tggcacccct acaactggga aagtgttcca tcgcgggctg gattctggga    240

aaccccgagt gcgaatccct tctgtcgaaa aagtcatggt cctacattgc cgaggccccg    300

aatgctgaga acggcatttg ctacccggga cacttcagcg attacgaaga actgcgggaa    360

cagctgtcga gcgtgtcaag tttcgagagg ttcgagatct tcccgaagga aagctcatgg    420

ccgaagcaca gcatcggcgc caccgcctcg tgttcgaaac agggaaagtc ctcgttctac    480

actaacctcc tgtggctgac cgagaagaat gggtcctatc ctaacctgac catgtcgtac    540

atgaacgaca aggaacggga agtgctcgtg ttgtgggggg tgcaccatcc atcaaatatc    600

gaggaccaga gggccatcta ccgcaaagaa actgcctacg tgtccgtgat gtctagccac    660

tacaacaagc gcttcacgcc tgaaatcgcc aaaagaccca aggtccgcaa ccaagagggc    720

agaatcaatt actactggac cctcctggag ccccgggaca ccataatctt tgaagcaaat    780

ggaaacctca ttgcgccttg gtacgccttc gccctgaacc ggggtttcga gtccggaatt    840

atcgtcagca acgcctccat ggacgagtgt aacgcgaagt gccagacccc gcgcggcgct    900

atcaacaaca gcctgccttt ccaaaacgtg cacccaatca ccatcggcga atgccccaaa    960

tacgtgaagt ccactaagct gaagatggca acaggactgc ggaacatccc gtcaattcag   1020

tcccgagggt tgttcggggc aatcgccggg ttcattgagg gcggatggac cggaatgatt   1080

gacggttggt acggatacca ccaccagaac gaacagggtt ccggttatgc ggcggatcag   1140

aagtccaccc agaacgccat caacggcatc accaacaagg tcaactccgt catcgacaag   1200

atgaacaccc agttcactgc cgtgggaaag gagttcaacc ggctggagaa gcggatggaa   1260

aatctgaaca agaaagtcga cgacggcttc ctggacattt ggacctacaa cgccgaactg   1320

ctggtgctgc tggaaaacga aagaactctc gactttcatg attcgaacgt gaagtcactg   1380

tacgaaggag tgaaggccca gctcaagaac aacgccaagg aagtcggaaa cggttgcttc   1440

gagttttacc ataagtgcga caacgagtgc atggatagcg tgaagaacgg aacctacgac   1500

tacccccggt attccgaaga gtcgaagctc aacagagaac agatcgatgg cgtggagctg   1560

aagtccatgg gagtgtacca gatcctggcg atctactcca ctgcggctag ctccctggtg   1620

ctgttggtca ccttgggggc tatctctttc tggatgtgct ccaacggttc cctgcaatgc   1680

cgcatttgca tttga                                                    1695
```

<210> SEQ ID NO 3
<211> LENGTH: 564
<212> TYPE: PRT
<213> ORGANISM: Influenza A virus
<220> FEATURE:
<223> OTHER INFORMATION: >ALX30160.1 hemagglutinin [Influenza A virus (A/swine/Italy/3033-1/2015(H1N2))]

<400> SEQUENCE: 3

```
Met Lys Ala Lys Leu Leu Ile Leu Leu Cys Ala Leu Ser Thr Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Val
    50                  55                  60

Ala Pro Leu Gln Leu Gly Lys Cys Ser Ile Ala Gly Trp Ile Leu Gly
65                  70                  75                  80
```

```
Asn Pro Glu Cys Glu Ser Leu Leu Ser Lys Lys Ser Trp Ser Tyr Ile
                85                  90                  95

Ala Glu Ala Pro Asn Ala Glu Asn Gly Ile Cys Tyr Pro Gly His Phe
            100                 105                 110

Ser Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Ser
    130                 135                 140

Ile Gly Ala Thr Ala Ser Cys Ser Lys Gln Gly Lys Ser Ser Phe Tyr
145                 150                 155                 160

Thr Asn Leu Leu Trp Leu Thr Glu Lys Asn Gly Ser Tyr Pro Asn Leu
                165                 170                 175

Thr Met Ser Tyr Met Asn Asp Lys Glu Arg Glu Val Leu Val Leu Trp
            180                 185                 190

Gly Val His His Pro Ser Asn Ile Glu Asp Gln Arg Ala Ile Tyr Arg
        195                 200                 205

Lys Glu Thr Ala Tyr Val Ser Val Met Ser Ser His Tyr Asn Lys Arg
    210                 215                 220

Phe Thr Pro Glu Ile Ala Lys Arg Pro Lys Val Arg Asn Gln Glu Gly
225                 230                 235                 240

Arg Ile Asn Tyr Tyr Trp Thr Leu Leu Glu Pro Arg Asp Thr Ile Ile
                245                 250                 255

Phe Glu Ala Asn Gly Asn Leu Ile Ala Pro Trp Tyr Ala Phe Ala Leu
            260                 265                 270

Asn Arg Gly Phe Glu Ser Gly Ile Ile Val Ser Asn Ala Ser Met Asp
        275                 280                 285

Glu Cys Asn Ala Lys Cys Gln Thr Pro Arg Gly Ala Ile Asn Asn Ser
    290                 295                 300

Leu Pro Phe Gln Asn Val His Pro Ile Thr Ile Gly Glu Cys Pro Lys
305                 310                 315                 320

Tyr Val Lys Ser Thr Lys Leu Lys Met Ala Thr Gly Leu Arg Asn Ile
                325                 330                 335

Pro Ser Ile Gln Ser Arg Gly Leu Phe Gly Ala Ile Ala Gly Phe Ile
            340                 345                 350

Glu Gly Gly Trp Thr Gly Met Ile Asp Gly Trp Tyr Gly Tyr His His
        355                 360                 365

Gln Asn Glu Gln Gly Ser Gly Tyr Ala Ala Asp Gln Lys Ser Thr Gln
    370                 375                 380

Asn Ala Ile Asn Gly Ile Thr Asn Lys Val Asn Ser Val Ile Asp Lys
385                 390                 395                 400

Met Asn Thr Gln Phe Thr Ala Val Gly Lys Glu Phe Asn Arg Leu Glu
                405                 410                 415

Lys Arg Met Glu Asn Leu Asn Lys Lys Val Asp Asp Gly Phe Leu Asp
            420                 425                 430

Ile Trp Thr Tyr Asn Ala Glu Leu Leu Val Leu Leu Glu Asn Glu Arg
        435                 440                 445

Thr Leu Asp Phe His Asp Ser Asn Val Lys Ser Leu Tyr Glu Gly Val
    450                 455                 460

Lys Ala Gln Leu Lys Asn Asn Ala Lys Glu Val Gly Asn Gly Cys Phe
465                 470                 475                 480

Glu Phe Tyr His Lys Cys Asp Asn Glu Cys Met Asp Ser Val Lys Asn
                485                 490                 495
```

```
Gly Thr Tyr Asp Tyr Pro Arg Tyr Ser Glu Glu Ser Lys Leu Asn Arg
            500                 505                 510

Glu Gln Ile Asp Gly Val Glu Leu Lys Ser Met Gly Val Tyr Gln Ile
        515                 520                 525

Leu Ala Ile Tyr Ser Thr Ala Ala Ser Ser Leu Val Leu Leu Val Thr
    530                 535                 540

Leu Gly Ala Ile Ser Phe Trp Met Cys Ser Asn Gly Ser Leu Gln Cys
545                 550                 555                 560

Arg Ile Cys Ile


<210> SEQ ID NO 4
<211> LENGTH: 1701
<212> TYPE: DNA
<213> ORGANISM: Influenza A virus
<220> FEATURE:
<223> OTHER INFORMATION: >KR700530.1 Influenza A virus (A/swine/Italy/
      28762-3/2013(H1N1)) segment 4 hemagglutinin (HA) gene, complete
      cds

<400> SEQUENCE: 4

atgaaagcaa aattatttgt attattctgt gcatttactg cactgaaagc tgacaccatt     60

tgtgtaggct atcatgctaa caattccaca gacactgtcg acacgatact ggaaaagaat    120

gttactgtta cccactcagt taatttacta gaaaacagcc acaatggaaa actctgcagc    180

ctgaatggaa aggctccgtt gcaactggag aactgcaacg tagcaggatg gatccttggt    240

aatccagaat gtgactttct gctcacagcg aattcatggt cctacataat agagacttca    300

aattcaaaaa atggaacatg ctatcctgga gaattcactg attatgagga actaagggag    360

caactgagta cagtttcttc atttgaaaga tttgaaattt tcccaaaagc aacctcatgg    420

ccaaatcatg agacaaccaa aggtaccaca gttgcatgct cccactctgg agccaacagt    480

ttttatcgga acttgctatg gatagtaaag aaaggaaact cctatcccaa gctcagcaag    540

tcatacacaa acaacaaagg gaaagaagtg cttgtaatct ggggagtgca tcaccccccct    600

acagacagtg accaacaaac cctctatcag aataatcaca catatgtttc agttggatca    660

tcaaaatact accaaaggtt cacaccagaa atagtagcca gacctaaagt cagagagcaa    720

gcgggcagaa tgaattatta ttggatacta ttagatcaag gagacaccat aacatttgaa    780

gccacgggga atttaatagc accatggcat gcatttgcat tgaataaggg ctctagctct    840

ggaattatga tgtcagatgc tcatgttcaa aattgcacta caaagtgcca aactcctcat    900

ggggcattga aaagcaatct tccttttcaa aatgtacatc ccatcactat tggagagtgc    960

cccaaatatg ttaaaagcac ccaactaaga atggcaacag gattaaggaa cataccatct   1020

atccaatcca gaggactttt tggggcaatt gccggattta ttgaaggagg atggacagga   1080

atgatagatg gatggtatgg atatcaccat caaaatgagc aaggatctgg ttatgcagca   1140

gataagaaaa gcacacaaat tgcaattgat gagatcagca acaaagtaaa ctcagtaatt   1200

gagaaaatga acattcaatt cacttcagtg ggcaaggagt tcaataattt agagaaaagg   1260

attgagaatt tgaataaaaa ggtcgatgat ggatttttgg atgtgtggac atataacgct   1320

gagttactca ttttgctcga gaacgaaaga accctagatt tccatgactt taacgtaaga   1380

aatttgtatg aaaaggtcaa atcacaactg agaaacaatg ccaaggaaat cggtaatggt   1440

tgttttgagt tctatcacag atgtgacaat gaatgcatgg aaagtgtaaa gaatggcaca   1500

tataattatc ccagatattc agaagaatcc aaattaaata gagagaaaat agacggtgtg   1560

aaactagaat cattaggagt acatcagatt ttggcaatct actccacagt cgccagttcc   1620
```

ctggtattgc tagtctccct gggggcaatc agtttctgga tgtgctctaa tggatcattg 1680
caatgcagaa tatgcatttg a 1701

<210> SEQ ID NO 5
<211> LENGTH: 1701
<212> TYPE: DNA
<213> ORGANISM: Artificial Sequence
<220> FEATURE:
<223> OTHER INFORMATION: >EUH1-3 Swine optimized sequence

<400> SEQUENCE: 5
atgaaagcca agctgtttgt ccttttctgc gccttcaccg cccttaaagc cgacaccatc 60
tgtgtgggct accatgctaa caactccacc gatacggtcg acactattct ggagaagaac 120
gtgaccgtga cccactccgt gaatctgctg gagaatagcc acaacggaaa gctgtgcagc 180
ctgaacggaa aggccccgct gcaactggag aattgtaacg tggccggatg gatcctgggc 240
aaccctgaat gcgacttcct gctgaccgcc aattcctggt cctacatcat cgagacttcc 300
aactccaaga acggaacgtg ctaccccggg gagttcactg attacgaaga actgcgcgaa 360
cagctgtcaa ctgtgtcctc gttcgagcgg ttcgaaatct tcccgaaagc cacctcgtgg 420
cccaatcatg aaaccaccaa gggaaccact gtggcctgct cccactctgg ggcgaactca 480
ttctatcgca acttgctgtg gatcgtcaag aagggaaaca gttaccctaa gctgtccaag 540
tcctacacta acaacaaggg aaaggaagtc ctcgtgatct ggggcgtgca tcacccaccc 600
accgactccg atcagcaaac actgtaccag aacaaccaca cctacgtgtc cgtgggatca 660
tccaagtact accagagatt caccccggaa atcgtcgcgc ggcccaaggt ccgcgaacaa 720
gccggccgga tgaactacta ctggatcctg ctggaccagg gcgacactat cactttcgag 780
gcgaccggga acctcatcgc cccttggcac gcattcgcac tgaacaaggg atcgagctcc 840
gggattatga tgagcgatgc tcatgtgcaa aactgtacta ccaagtgcca gacccctcac 900
ggtgccctga agtccaattt gcccttccaa aatgtgcacc ccattaccat tggcgaatgc 960
ccgaaatacg tgaagtcgac ccaactccgg atggccaccg gccttcggaa catcccatcg 1020
atacagtcga ggggtctttt cggagcgatt gcgggattca tcgagggcgg ctggaccgga 1080
atgattgacg gttggtacgg ataccaccac cagaacgaac agggctccgg atacgccgcc 1140
gacaaaaagt cgactcagat cgcaattgac gagattagca acaaggtcaa ctccgtgatc 1200
gagaagatga atatccagtt tactagcgtg ggaaaggagt tcaacaacct ggagaagagg 1260
atcgagaacc tgaacaagaa agtggacgat ggattcctcg acgtgtggac atacaacgcc 1320
gagctcctca ttttgctgga gaacgaacgg accctcgact tccatgactt caacgtgcgc 1380
aacctgtacg aaaaggtcaa gagccagctg agaaacaacg ccaaggaaat tggcaacggt 1440
tgctttgagt ttaccaccg ctgcgacaac gaatgcatgg agagcgtgaa gaacgggacc 1500
tacaactatc cgagatactc agaggaatca aagctgaacc gcgaaaagat cgatggcgtg 1560
aagctcgaat cactcggcgt gcaccagatc ctggccatct attccactgt ggctagctcc 1620
ctcgtgctgc tggtgtccct gggtgctatt tccttctgga tgtgcagcaa cgggtcgctc 1680
cagtgccgga tctgtatctg a 1701

<210> SEQ ID NO 6
<211> LENGTH: 566
<212> TYPE: PRT
<213> ORGANISM: Influenza A virus
<220> FEATURE:

<223> OTHER INFORMATION: >AKJ81667.1 hemagglutinin [Influenza A virus (A/swine/Italy/28762-3/2013(H1N1))]

<400> SEQUENCE: 6

```
Met Lys Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asn Ser His Asn Gly Lys Leu Cys Ser Leu Asn Gly Lys
    50                  55                  60

Ala Pro Leu Gln Leu Glu Asn Cys Asn Val Ala Gly Trp Ile Leu Gly
65                  70                  75                  80

Asn Pro Glu Cys Asp Phe Leu Leu Thr Ala Asn Ser Trp Ser Tyr Ile
                85                  90                  95

Ile Glu Thr Ser Asn Ser Lys Asn Gly Thr Cys Tyr Pro Gly Glu Phe
            100                 105                 110

Thr Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Glu
    130                 135                 140

Thr Thr Lys Gly Thr Thr Val Ala Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Asp Gln Gln Thr Leu
        195                 200                 205

Tyr Gln Asn Asn His Thr Tyr Val Ser Val Gly Ser Ser Lys Tyr Tyr
    210                 215                 220

Gln Arg Phe Thr Pro Glu Ile Val Ala Arg Pro Lys Val Arg Glu Gln
225                 230                 235                 240

Ala Gly Arg Met Asn Tyr Tyr Trp Ile Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Ser Ser Ser Gly Ile Met Met Ser Asp Ala His
        275                 280                 285

Val Gln Asn Cys Thr Thr Lys Cys Gln Thr Pro His Gly Ala Leu Lys
    290                 295                 300

Ser Asn Leu Pro Phe Gln Asn Val His Pro Ile Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Lys Lys Ser
    370                 375                 380

Thr Gln Ile Ala Ile Asp Glu Ile Ser Asn Lys Val Asn Ser Val Ile
385                 390                 395                 400
```

Glu Lys Met Asn Ile Gln Phe Thr Ser Val Gly Lys Glu Phe Asn Asn
405 410 415

Leu Glu Lys Arg Ile Glu Asn Leu Asn Lys Lys Val Asp Asp Gly Phe
420 425 430

Leu Asp Val Trp Thr Tyr Asn Ala Glu Leu Leu Ile Leu Leu Glu Asn
435 440 445

Glu Arg Thr Leu Asp Phe His Asp Phe Asn Val Arg Asn Leu Tyr Glu
450 455 460

Lys Val Lys Ser Gln Leu Arg Asn Asn Ala Lys Glu Ile Gly Asn Gly
465 470 475 480

Cys Phe Glu Phe Tyr His Arg Cys Asp Asn Glu Cys Met Glu Ser Val
485 490 495

Lys Asn Gly Thr Tyr Asn Tyr Pro Arg Tyr Ser Glu Glu Ser Lys Leu
500 505 510

Asn Arg Glu Lys Ile Asp Gly Val Lys Leu Glu Ser Leu Gly Val His
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 7
<211> LENGTH: 1701
<212> TYPE: DNA
<213> ORGANISM: Influenza A virus
<220> FEATURE:
<223> OTHER INFORMATION: >KU323308.1 Influenza A virus (A/swine/Italy/
240849/2015(H3N2)) segment 4 hemagglutinin (HA) gene, complete cds

<400> SEQUENCE: 7
atgaagactg tcattgcttt aagctacgtc ttttgcctgg tttttggcca agattttcca 60
ggaaagggca acaacacagc aacactgtgc ctagggcatc atgcagtgcc aaatgggaca 120
ttagtgaaaa caatcacaga tgatcaaatc gaagtaacca atgccacaga actggtccaa 180
aatttctcaa tgggtaaaat atgcaagaat cctcatcgaa ttcttgatgg ggcaaattgt 240
acattggtag actctctatt gggggaccct cactgtgatg gttttcaaaa tgagaaatgg 300
gacctcttca ttgaacgcag cagggctttc agcaactgct acccttatga tgtgccggag 360
tatacctctc ttaggtcact aattgcctca tcaggcacct tggaatttac caatgaaaat 420
ttcaattgga ctggagttac ccaaaatggg ggaagcagtg cttgcaagag ggggcccaac 480
aacagctttt tcagtagatt gaactggttg tacaaatcag gaaacacata tccgatgcta 540
aatgttacta tgccaaacag tgatgatttc gacaaattgt acatttgggg agttcatcat 600
ccgagcaccg atagagaaca gaccaacctg tacattcaag catcagggaa aataatagta 660
tccacaaaga gaagtcaaca aaccataatc ccgaatatcg ggtctagacc ctgggtaagg 720
ggtttatcta gtaggataag catctactgg acaatagtta aaccaggaga catcctgata 780
atcaacagca atggaaacct aattgctcct cggggttact tcaagataca gactgggaaa 840
agttcagtaa tgaagtcaga tgcacctatt ggcacctgca attcagaatg cattactcca 900
aacggaagca tacccaatga taaacccttt caaaacgtaa acaggatcac atatggggca 960
tgccctcatt acatcaagca aaacactctg aagctagcaa caggaatgcg gaatatacca 1020
gaaagacaaa ccagaggtat attcggtgca atagcagggt tcatagagaa tggttgggaa 1080
ggaatggtga acggttggta cggtttcaga caccaaaatt ctgagggcat aggacaggca 1140
gcagatctta aaagtaccca agcagctatc aaccaaatca atggaaaact gaatagagta 1200
atcgagaaaa caaacgagaa attccatcaa atcgaaaagg agttctcaga agtagaagga 1260
aggatccaag accttgaaag atatgttgaa gatactaaga tagatctttg gtcttacaac 1320
gcggaacttc ttgtcgcact agagaatcaa cacacaattg acctgactga ctcagaaatg 1380
aacaaactct ttgaaaaaac aaggaaacaa ctaagggaaa atgctgagga catgggaaat 1440
ggttgcttca aaatatacca caaatgtgac aactcttgca tggagtcaat cagaaatggg 1500
acttacgacc ataatgaata cagagacgaa gcagtaaaca atcgattcca aatcaaaagt 1560
gttgagctga agtcaggata caaagactgg atcctgtgga tttcctttgc catatcatgc 1620
tttttgcttt gcgctatttg gatgggattc gtaatatggg cctgccagaa aggcaacatt 1680
agatgcaata tttgcatctg a 1701

<210> SEQ ID NO 8
<211> LENGTH: 1701
<212> TYPE: DNA
<213> ORGANISM: Artificial Sequence
<220> FEATURE:
<223> OTHER INFORMATION: >EUH3-4_Swine optimized sequence

<400> SEQUENCE: 8
atgaaaaccg tcattgcgtt gagctatgtg ttttgtctcg tgtttggaca agacttcccg 60
ggaaagggca acaacaccgc caccctgtgc ctggggcacc atgccgtgcc caacggaact 120
ctcgtcaaga ccatcaccga cgaccagatc gaggtcacca atgcgaccga gttggtgcag 180
aatttctcca tgggaaagat ctgcaagaac ccgcaccgga ttttggatgg agccaactgc 240
acactggtgg actccctgct gggtgatcct cattgcgacg gattccaaaa cgagaagtgg 300
gatctgttca tcgagagatc ccgggccttc agcaactgct acccgtacga cgtgccagag 360
tacactagct tgcggtccct gatcgcctcc agcggtaccc tggagttcac caacgagaac 420
ttcaactgga ccggcgtgac gcagaacggg ggttcctcag cgtgcaagcg gggaccgaac 480
aactcgttct tctcccggct taactggctg tacaagagcg gcaacacata ccccatgctg 540
aacgtgacca tgcccaactc tgacgacttt gataagctgt acatctgggg agtgcaccac 600
ccatcgactg accgcgaaca gaccaacctg tacatccaag cctccggcaa aatcattgtg 660
tccaccaaga gatcgcagca gaccatcatt ccgaacattg gcagtcggcc atgggtcaga 720
ggactgtcgt ccagaatcag catctactgg accattgtga agcccggcga catcctcatc 780
ataaactcga acggcaacct gatcgcccca cggggatatt tcaagatcca gaccggaaag 840
agctccgtga tgaagtccga tgccccgatt gggacttgca actccgagtg catcaccccc 900
aacggctcca tccccaacga caaacccttc caaaacgtga accgcatcac ttacggagcc 960
tgcccgcatt acatcaagca gaacacgctc aagctcgcca ctgggatgcg caacattcct 1020
gagcgccaaa cccggggaat cttcggagcc attgcgggct tcatcgaaaa cggctgggaa 1080
gggatggtca acggttggta cggttttaga caccaaaatt ccgaaggaat cggacaggct 1140
gccgatctca aatcaaccca ggccgccatc aaccagatca acgggaagct gaacagagtg 1200
atcgaaaaga ccaacgaaaa gttccatcag attgagaagg agttttccga agtcgaggga 1260
cggattcaag acctggagcg ctacgtggag gacaccaaga ttgatctgtg gagctacaac 1320
gcagagctcc tggtcgcgct ggaaaatcag cacaccattg acttgaccga ctcggagatg 1380

```
aacaagctgt ttgaaaagac caggaagcag ctgcgggaaa acgccgaaga tatggggaac   1440

ggatgcttca aaatctacca taagtgcgac aatagctgca tggaaagcat taggaacggg   1500

acttacgacc ataacgagta cagagatgaa gcagtgaaca acagattcca gatcaagtcc   1560

gtggaactca agagcggtta caaggactgg atcctctgga tttcgttcgc tatttcgtgc   1620

ttcctgctgt gcgccatctg gatgggattc gtcatctggg cctgccagaa gggcaacatc   1680

cggtgcaaca tttgtatttg a                                             1701


<210> SEQ ID NO 9
<211> LENGTH: 566
<212> TYPE: PRT
<213> ORGANISM: Influenza A virus
<220> FEATURE:
<223> OTHER INFORMATION: >ALX30415.1 hemagglutinin [Influenza A virus
      (A/swine/Italy/240849/2015(H3N2))] EUH3-4

<400> SEQUENCE: 9

Met Lys Thr Val Ile Ala Leu Ser Tyr Val Phe Cys Leu Val Phe Gly
1               5                   10                  15

Gln Asp Phe Pro Gly Lys Gly Asn Asn Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Asn Phe Ser Met
    50                  55                  60

Gly Lys Ile Cys Lys Asn Pro His Arg Ile Leu Asp Gly Ala Asn Cys
65                  70                  75                  80

Thr Leu Val Asp Ser Leu Leu Gly Asp Pro His Cys Asp Gly Phe Gln
                85                  90                  95

Asn Glu Lys Trp Asp Leu Phe Ile Glu Arg Ser Arg Ala Phe Ser Asn
            100                 105                 110

Cys Tyr Pro Tyr Asp Val Pro Glu Tyr Thr Ser Leu Arg Ser Leu Ile
        115                 120                 125

Ala Ser Ser Gly Thr Leu Glu Phe Thr Asn Glu Asn Phe Asn Trp Thr
    130                 135                 140

Gly Val Thr Gln Asn Gly Gly Ser Ser Ala Cys Lys Arg Gly Pro Asn
145                 150                 155                 160

Asn Ser Phe Phe Ser Arg Leu Asn Trp Leu Tyr Lys Ser Gly Asn Thr
                165                 170                 175

Tyr Pro Met Leu Asn Val Thr Met Pro Asn Ser Asp Asp Phe Asp Lys
            180                 185                 190

Leu Tyr Ile Trp Gly Val His His Pro Ser Thr Asp Arg Glu Gln Thr
        195                 200                 205

Asn Leu Tyr Ile Gln Ala Ser Gly Lys Ile Ile Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Ile Ile Asn Ser Asn Gly Asn Leu Ile Ala Pro Arg Gly
            260                 265                 270

Tyr Phe Lys Ile Gln Thr Gly Lys Ser Ser Val Met Lys Ser Asp Ala
        275                 280                 285

Pro Ile Gly Thr Cys Asn Ser Glu Cys Ile Thr Pro Asn Gly Ser Ile
```

```
    290                 295                 300

Pro Asn Asp Lys Pro Phe Gln Asn Val Asn Arg Ile Thr Tyr Gly Ala
305                 310                 315                 320

Cys Pro His Tyr Ile Lys Gln Asn Thr Leu Lys Leu Ala Thr Gly Met
                325                 330                 335

Arg Asn Ile Pro Glu Arg Gln Thr Arg Gly Ile Phe Gly Ala Ile Ala
            340                 345                 350

Gly Phe Ile Glu Asn Gly Trp Glu Gly Met Val Asn Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Arg Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ser Cys Met Glu Ser
                485                 490                 495

Ile Arg Asn Gly Thr Tyr Asp His Asn Glu Tyr Arg Asp Glu Ala Val
            500                 505                 510

Asn Asn Arg Phe Gln Ile Lys Ser Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Ala Ile Trp Met Gly Phe Val Ile Trp Ala Cys Gln Lys Gly Asn Ile
545                 550                 555                 560

Arg Cys Asn Ile Cys Ile
                565


<210> SEQ ID NO 10
<211> LENGTH: 1701
<212> TYPE: DNA
<213> ORGANISM: Influenza A virus
<220> FEATURE:
<223> OTHER INFORMATION: >CY116127.1 Influenza A virus (A/swine/England/
      373/2010(H1N1)) hemagglutinin (HA) gene, complete cds

<400> SEQUENCE: 10

atgaaggcaa tactagtagt tctgctacat acatttgcaa ccgcaaatgc agacacatta      60

tgtataggtt atcatgcgaa caattcaaca gacactgtag acacagtact agaaaagaat     120

gtaacagtaa cacactctgt taaccttcta gaagacaagc ataacgggaa actatgcaaa     180

ctaagagggg tagccccatt gcatttgggt aaatgtaaca ttgctggctg gatcctggga     240

aatccagagt gtgaatcact ctccacagca agctcatggt cctacattgt ggaaacatct     300

agttcagaca atggaacgtg ttacccagga gatttcatcg attatgagga gctaagagag     360

caattgagct cagtgtcatc atttgaaagg tttgagatat tccccaagac aagttcatgg     420

cccaatcatg actcgaacaa aggtgtaacg gcagcatgtc ctcatgctgg agcaaaaagc     480
```

ttctacaaaa atttaatatg gctagttaaa aaaggaaatt catacccaaa gctcagcaaa 540
tcctacatta atgataaagg gaaagaagtc ctcgtgctat ggggcattca ccatccatct 600
actagtgctg accaacaaag tctctatcag aatgcagatg catatgtttt tgtggggaca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca gacacccaag 900
ggtgctataa acaccagcct cccatttcag aatatacatc cgatcacaat tggaaaatgt 960
ccaaaatatg taaaaagcac aaaattgaga ctggccacag gattgaggaa cgtcccgtct 1020
attcaatcta gaggcctatt tggggccatt gccggtttca ttgaaggggg gtggacaggg 1080
atggtagatg gatggtacgg ttatcaccat caaaatgagc aggggtcagg atatgcagcc 1140
gacctgaaga gcacacagca tgccattgac gagattacta acaaagtaaa ttctgttatt 1200
gaaaagatga atacacagtt cacagcagta ggtaaagagt tcaaccacct ggaaaaaaga 1260
atagagaatt taaataaaaa agttgatgat ggtttcctgg acatttggac ttacaatgcc 1320
gaactgttgg ttctattgga aaatgaaaga actttggact accacgattc aaatgtgaag 1380
aacttatatg aaaaggtaag aagccagtta aaaaacaatg ccaaggaaat tggaaacggc 1440
tgctttgaat tttaccacaa atgcgataac acgtgcatgg aaagtgtcaa aaatgggact 1500
tatgactacc caaaatactc agaggaagca aaattaaaca gagaagaaat agatggggta 1560
aagctagaat caacaaggat ttaccagatt ttggcgatct attcaactgt cgccagttca 1620
ttggtactgg tagtctccct gggggcaatc agtttctgga tgtgctctaa tgggtctcta 1680
cagtgtagaa tatgtattta a 1701

<210> SEQ ID NO 11
<211> LENGTH: 1701
<212> TYPE: DNA
<213> ORGANISM: Artificial Sequence
<220> FEATURE:
<223> OTHER INFORMATION: >EUH1-11 Swine optimized sequence

<400> SEQUENCE: 11
atgaaggcta ttctggtggt cctgctccac acttttgcca ccgcgaacgc agataccctc 60
tgcatcggat accacgccaa caattccacc gatactgtgg ataccgtgct ggaaaagaac 120
gtgaccgtga ctcactcagt gaacctcctg gaagataagc acaacggaaa gctttgcaag 180
cttcggggag tggctccgtt gcatctggga aagtgcaaca tcgccggatg gatcctgggc 240
aaccccgagt gcgagagcct gtccaccgcc tcctcctggt cttacattgt ggaaacctcc 300
tcgtccgata acggcacatg ctatccgggg gacttcattg actacgaaga actgagggag 360
caactcagct ccgtgagctc ctttgagcgc ttcgaaatct tccctaagac ctcatcctgg 420
cccaaccacg actccaacaa gggagtgact gcagcgtgtc cgcacgctgg agccaagtca 480
ttctacaaga acctgatctg gctggtcaaa aagggaaact cgtaccccaa gctgtctaag 540
tcctacatca atgacaaggg gaaggaagtg ctggtgctgt ggggaatcca ccacccttcc 600
acctccgccg accagcagtc gctgtaccag aacgctgatg cgtacgtgtt cgtcggcact 660
agccgctact ccaagaagtt caagccagaa attgccatcc ggcccaaagt ccgcgatcag 720
gaggggcgga tgaactacta ctggactctc gtggaacccg gggataagat cacgttcgaa 780

```
gctaccggca acctcgtggt gcctcgctac gccttcgcaa tggagaggaa tgctggaagc    840

ggtatcatca tttcggacac tcctgtgcat gactgcaata cgacttgtca gactccgaag    900

ggagcgatca acacttccct cccgttccaa aacatccacc ccattacaat tggcaaatgt    960

cctaaatacg tgaagtcgac caagctccgg cttgcaactg ggctgcgcaa tgtgcctagc   1020

attcagtcaa ggggcctatt tggggccatc gccggtttca tcgagggagg atggaccgga   1080

atggtggacg gttggtatgg ctaccaccac caaaacgaac agggctccgg ttacgccgcc   1140

gacctgaagt ccacccagca cgccattgac gaaatcacca acaaggtcaa ctccgtcatc   1200

gagaagatga acacccagtt cactgccgtg ggaaaggagt tcaaccatct ggagaagaga   1260

attgagaacc tcaataagaa agtggacgac ggcttcctgg acatctggac ctacaacgcc   1320

gagctgctgg tcctgctgga aaacgagagg accctggact accacgactc gaacgtgaag   1380

aacctgtacg agaaggtccg atcacaactg aagaacaacg ccaaggaaat cggaaatggg   1440

tgcttcgagt tctaccacaa atgcgacaat acttgcatgg aatccgtgaa gaatggcacc   1500

tacgattacc ctaagtattc cgaggaagcg aagctgaacc gggaagagat tgacggcgtg   1560

aagctcgaat caacccggat ctaccagatc cttgcgatct actccaccgt ggccagctca   1620

ctcgtgctcg tggtgtccct gggtgccatc tccttctgga tgtgtagcaa cggcagcctc   1680

cagtgccgca tctgtatctg a                                             1701
```

```
<210> SEQ ID NO 12
<211> LENGTH: 566
<212> TYPE: PRT
<213> ORGANISM: Influenza A virus
<220> FEATURE:
<223> OTHER INFORMATION: >AFR76205.1 hemagglutinin [Influenza A virus
      (A/swine/England/373/2010(H1N1) EUH1-11

<400> SEQUENCE: 12

Met Lys Ala Ile Leu Val Val Leu Leu His Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190
```

```
Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln His Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 13
<211> LENGTH: 1410
<212> TYPE: DNA
<213> ORGANISM: Influenza A virus
<220> FEATURE:
<223> OTHER INFORMATION: >KR700793.1 Influenza A virus (A/swine/England/

61470/2013(H1N2)) segment 6 neuraminidase (NA) gene, complete cds

<400> SEQUENCE: 13

```
atgaatccaa atcagaagat aataacaatt ggctctgttt ctctcgtcat tgcaacatta     60
tgcttcttaa tgcagatggc catcctaata actactgtaa aattacattt caaacaatat    120
gagtgcggct tccctgcgaa caaccaagta ataacatgtg agccaacagt aatagaaagg    180
aacacaacag agatagtgta cttaactaac accaccatag agaaagaaac atgccacaaa    240
acagtggaat acaggaattg gtcaaagcct caatgcaaaa taacaggctt tgcacctttt    300
tccaaggaca attcaattcg actttctgct ggtggggaca tatgggtgac gagggaacct    360
tacgtgtcat gcgagcctgg caaatgttat cagtttgcac tcgggcaagg gaccacacta    420
gacaataaac attcaaacga tacaatacat gacagaaccc cctatcgaac tctattgatg    480
aatgaattgg gtgtcccatt tcatttaggg acaagacaag tgtgtattgc atggtccagc    540
tcaagttgtt atgatgggaa agcatggttg catgtctgta tcactggaca tgataaaaat    600
gcaactgcca gtttcattta cgatggtaga cttgtagata gcattggttc atggtctaaa    660
aatatactta gaacccagga atcagaatgc gtttgcatca atggggtctg tacagtagta    720
atgactgatg gaagtgcttc gggaagagct gatactaaaa tactattcat tgaagaaggg    780
aaaattgttc atattagccc attagcgggg agtgcacagc atgtggagga gtgctcctgt    840
tatccccgat atcctggcgt aaggtgtatc tgcagagaca actggaaagg ctctaacaga    900
cccgttgtgg atataaatat agaagattat agcattgatt ccagttatgt gtgttcaggg    960
cttgttggcg acacacccag aatcaatgac ggatccagta gtagctactg ccgtgatcct   1020
aacaacgaaa aaggaaatca cggagtgaag ggctgggctt ttgacgatgg aaatgatgtg   1080
tggatgggaa gaacgatcaa cgaagattca cgctcaggtt atgaaacatt caaagtcatt   1140
ggtggttggt ccactcctaa ttccaaattg cagataaata ggcaagtaat agttgatagc   1200
aacaataggt caggttattc tggtgttttc tccgttgaag gcaaaagctg catcaataga   1260
tgtttctacg tggagttgat aagaggaaga aggtcagaag cgcgagtatg gtggacctca   1320
aacagtattg ttgtattttg tggcacttca ggtacctatg gaacaggctc atggcctgat   1380
ggagcagaca tcaacctcat gcctatatga                                    1410
```

<210> SEQ ID NO 14
<211> LENGTH: 1410
<212> TYPE: DNA
<213> ORGANISM: Artificial Sequence
<220> FEATURE:
<223> OTHER INFORMATION: >EUN2-6 Swine optimized sequence

<400> SEQUENCE: 14

```
atgaatccga accagaaaat tatcaccatt gggtccgtca gccttgtgat tgccactctg     60
tgctttctga tgcaaatggc catcctcatt accactgtga agctgcattt caagcagtac    120
gaatgcggct tccccgcgaa caaccaggtc atcacttgcg agccaaccgt gattgagcgg    180
aacactaccg aaattgtata cctcacgaac actaccattg aaaaggagac ttgccacaag    240
accgtggaat accggaactg gtccaagcct cagtgcaaga ttaccgggtt cgccccattc    300
tccaaggaca atagcatccg cctttcggcc ggaggagata tttgggtgac gcgcgaaccc    360
tacgtcagct gcgaacccgg gaagtgttac cagttcgcac tgggccaggg aaccaccctg    420
gataataagc acagcaacga caccatccac gaccggactc cctaccgcac cctcctgatg    480
aatgagctcg gcgtgccgtt ccacctgggt accagacagg tctgcatcgc ctggtcgtcc    540
```

```
tcctcatgct acgatgggaa ggcttggctc cacgtgtgca taaccggtca tgacaagaac    600

gccacagcct cattcatcta cgacggacgg ctagtggact ccatcggctc ctggtccaag    660

aacattctga ggacccagga atccgaatgc gtctgtatca acggagtgtg caccgtggtg    720

atgaccgatg gctccgcaag cggaagggcc gatactaaga tcctgttcat cgaggaggga    780

aagattgtgc acatctctcc tctcgcggga tcagcccagc acgtggaaga atgttcctgt    840

taccctcgct acccgggagt gcgctgtatt tgccgggaca actggaaagg ctccaacagg    900

cctgtggtgg acattaatat cgaggactac tccatcgata gctcctacgt gtgctccggt    960

ctggtcgggg acactccaag aatcaacgat ggaagctcca gcagctactg ccgggacccc   1020

aataacgaaa aggggaacca cggcgtgaag ggttgggcgt tcgacgatgg aaatgacgtc   1080

tggatgggac ggactatcaa cgaggactca cggagcggat acgaaacctt taaggtcatc   1140

ggcggatggt cgaccccgaa cagcaagctg cagatcaacc gccaagtgat cgtggactcc   1200

aacaaccgct cggggtatag cggggtgttc tccgtggagg gaaagtcctg catcaaccgg   1260

tgcttctacg tcgaactgat cagaggccgg agatcagaag cccgcgtgtg gtggacctcc   1320

aactccattg tggtgttttg cggcacttcc gggacctatg gcactggatc ctggcccgat   1380

ggagcagaca tcaacctgat gccaatctga                                    1410
```

```
<210> SEQ ID NO 15
<211> LENGTH: 469
<212> TYPE: PRT
<213> ORGANISM: Influenza A virus
<220> FEATURE:
<223> OTHER INFORMATION: >AKJ82042.1 neuraminidase [Influenza A virus
      (A/swine/England/61470/2013(H1N2))] EUN2-6

<400> SEQUENCE: 15

Met Asn Pro Asn Gln Lys Ile Ile Thr Ile Gly Ser Val Ser Leu Val
1               5                   10                  15

Ile Ala Thr Leu Cys Phe Leu Met Gln Met Ala Ile Leu Ile Thr Thr
            20                  25                  30

Val Lys Leu His Phe Lys Gln Tyr Glu Cys Gly Phe Pro Ala Asn Asn
        35                  40                  45

Gln Val Ile Thr Cys Glu Pro Thr Val Ile Glu Arg Asn Thr Thr Glu
    50                  55                  60

Ile Val Tyr Leu Thr Asn Thr Thr Ile Glu Lys Glu Thr Cys His Lys
65                  70                  75                  80

Thr Val Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Glu Pro Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys Tyr Asp Gly Lys Ala Trp Leu His Val
            180                 185                 190

Cys Ile Thr Gly His Asp Lys Asn Ala Thr Ala Ser Phe Ile Tyr Asp
```

```
        195                 200                 205

Gly Arg Leu Val Asp Ser Ile Gly Ser Trp Ser Lys Asn Ile Leu Arg
    210                 215                 220

Thr Gln Glu Ser Glu Cys Val Cys Ile Asn Gly Val Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ala Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Ile Glu Asp Tyr Ser Ile Asp Ser Ser Tyr Val Cys Ser Gly
305                 310                 315                 320

Leu Val Gly Asp Thr Pro Arg Ile Asn Asp Gly Ser Ser Ser Ser Tyr
                325                 330                 335

Cys Arg Asp Pro Asn Asn Glu Lys Gly Asn His Gly Val Lys Gly Trp
            340                 345                 350

Ala Phe Asp Asp Gly Asn Asp Val Trp Met Gly Arg Thr Ile Asn Glu
        355                 360                 365

Asp Ser Arg Ser Gly Tyr Glu Thr Phe Lys Val Ile Gly Gly Trp Ser
    370                 375                 380

Thr Pro Asn Ser Lys Leu Gln Ile Asn Arg Gln Val Ile Val Asp Ser
385                 390                 395                 400

Asn Asn Arg Ser Gly Tyr Ser Gly Val Phe Ser Val Glu Gly Lys Ser
                405                 410                 415

Cys Ile Asn Arg Cys Phe Tyr Val Glu Leu Ile Arg Gly Arg Arg Ser
            420                 425                 430

Glu Ala Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 16
<211> LENGTH: 1410
<212> TYPE: DNA
<213> ORGANISM: Influenza A virus
<220> FEATURE:
<223> OTHER INFORMATION: >KU323318.1 Influenza A virus (A/swine/Italy/
      248147-8/2015(H3N2)) segment 6 neuraminidase (NA) gene, complete
      cds

<400> SEQUENCE: 16

atgaatccaa atcaaaagat aataacaatt ggttctgttt ctctcactat tacaacaatg      60

tgcctcttct tgcagattgc catcctagta actactataa cattgcattt caagcaatat     120

gaatgcgatt cccctgcaaa caaccaagta ataccgtgtg aaccaataat aatagaaaaa     180

aacataacaa aaatagtgta tttgaccaat accaccatag agaaagaggt atgcccaaaa     240

ttaggggaat acaggaattg gtcaaaacca caatgcaaga tcacaggatt tgcacctttt     300

tctaaggaca attcaattcg gctctctgcg ggtggggcca tttgggtcac gagagaacct     360

tatgtgtcat gcgaccctaa caagtgttat caatttgcat taggacaggg aaccacatta     420
```

```
gataacagac attcaaatga cacaatacat gatagaaccc cttttagaac cctgttgatg    480

agtgaattag gtgttccatt tcatttggga accagacaag tatgcatagc atggtccagt    540

tcaagttgtc acgatgggaa agcttggttg catgtttgtg tcactgggca tgataaaaat    600

gcaactgcta gtttcattta tgacggaaag cttgtagaca gcatcagttc atggtccaaa    660

aacatactcc ggactcagga atcagaatgt gtttgtatcg atggaatctg tacagtggtg    720

atgactgatg gaagtgcttc agggaaagct gatactaaga tactatttat tgaaaaaggg    780

aagatcattc atattagtcc attgttggga agtgctcagc atgtagaaga atgttcctgt    840

taccctagat accctgatgt caggtgtatt tgcagggata actggaaagg ttcaaatagg    900

cccatcgtag acataagaat gaaaaattat agcattggtt ccagttatat gtgctcagga    960

cttgttggcg acacacccag gaacaatgat gggtctagta atagcaattg tcggaatccc   1020

aataatgaaa gaggaaatca tggagtgaaa ggttgggcct ttgatgatgg aaatgacaca   1080

tggatgggaa gaactatcag caaggactca cgcttaggtt acgaaacctt caaagttgtt   1140

ggtggttggt cccaacccaa ttccaaatcc cagataaata gacaagttat tgttgacagc   1200

gataatagat caggttactc tggtattttc tctgttgagg ggaaagattg cattaatagg   1260

tgtttttatg tggaactaat aagaggaagg agacaggaaa ctagagtgtg gtggacttcg   1320

aacagtattg ttgtgttctg tggcacttct ggcacctatg ggtcaggctc atggcccgat   1380

ggagcaaaca tcaatttcat gcctgtataa                                    1410
```

<210> SEQ ID NO 17
<211> LENGTH: 1410
<212> TYPE: DNA
<213> ORGANISM: Artificial Sequence
<220> FEATURE:
<223> OTHER INFORMATION: >EUN2-7 Swine optimized sequence

<400> SEQUENCE: 17

```
atgaacccta atcagaagat catcacaatc ggctccgtgt ccctcaccat caccactatg     60

tgcctcttcc ttcaaatcgc cattctggtc accaccatca ccctgcattt caagcagtac    120

gaatgcgact caccagcgaa caatcaggtc atcccgtgtg aaccgatcat tatcgagaag    180

aacatcacta agattgtgta tttgaccaac accaccattg agaaggaagt ctgcccaaag    240

ctcggggaat accgcaactg gagcaagccc cagtgcaaga ttaccggctt cgccccgttc    300

tcaaaagaca actccatccg gctgtctgcg ggaggagcca tctgggtcac gagagaaccg    360

tacgtgtcgt gcgaccccaa caagtgctac cagttcgccc tgggacaagg gaccaccctg    420

gacaaccggc actccaacga cactatacat gataggactc ccttccggac ccttctcatg    480

agcgaactgg gggtcccctt ccatctcgga accagacaag tctgcattgc gtggagctcc    540

tcctcctgcc acgacggaaa agcttggctc cacgtctgcg tgacgggcca cgacaagaac    600

gccactgcct ccttcatcta cgatgggaag cttgtggact ccatctcgtc atggagcaag    660

aacatcctgc ggactcagga gtcagaatgc gtgtgcatcg acggcatttg caccgtcgtg    720

atgactgacg gttcggccag cggaaaggcc gacaccaaga tcctgttcat cgagaaggga    780

aagatcattc acatctcccc acttctgggt tccgcgcaac acgtggaaga atgctcctgc    840

tacccccgct accccgatgt ccggtgcatc tgccgggaca actggaaggg ttccaaccgg    900

ccaatcgtgg acatccgcat gaagaactat tccatcgggt cctcttacat gtgctcgggt    960

ctggtcggag atacaccgcg caacaacgac gggtcctcaa acagcaactg ccggaaccct   1020

aacaacgaga ggggcaacca cggcgtgaaa ggatgggctt tcgacgacgg aaatgacact   1080
```

```
tggatgggga gaaccattag caaggatagc aggcttggct acgaaacctt caaggtcgtg   1140

ggcggttggt cgcagccgaa ctcgaagtcg cagatcaaca gacaggtcat cgtggactcg   1200

gataacagat cggggtactc agggatcttc tccgtggagg gaaaggactg catcaataga   1260

tgtttctacg tcgagctgat tcgaggccgg agacaggaaa cccgcgtatg gtggacgtcc   1320

aactcaatcg tcgtgttttg cggtacctcc ggaacttacg gctcgggatc atggcccgat   1380

ggagccaata ttaacttcat gcctgtgtga                                    1410


<210> SEQ ID NO 18
<211> LENGTH: 469
<212> TYPE: PRT
<213> ORGANISM: Influenza A virus
<220> FEATURE:
<223> OTHER INFORMATION: >ALX30429.1 neuraminidase [Influenza A virus
      (A/swine/Italy/248147-8/2015(H3N2))] EUN2-7

<400> SEQUENCE: 18

Met Asn Pro Asn Gln Lys Ile Ile Thr Ile Gly Ser Val Ser Leu Thr
1               5                   10                  15

Ile Thr Thr Met Cys Leu Phe Leu Gln Ile Ala Ile Leu Val Thr Thr
            20                  25                  30

Ile Thr Leu His Phe Lys Gln Tyr Glu Cys Asp Ser Pro Ala Asn Asn
        35                  40                  45

Gln Val Ile Pro Cys Glu Pro Ile Ile Ile Glu Lys Asn Ile Thr Lys
    50                  55                  60

Ile Val Tyr Leu Thr Asn Thr Thr Ile Glu Lys Glu Val Cys Pro Lys
65                  70                  75                  80

Leu Gly Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Ala Ile Trp Val Thr Arg Glu Pro Tyr Val Ser Cys Asp Pro Asn Lys
        115                 120                 125

Cys Tyr Gln Phe Ala Leu Gly Gln Gly Thr Thr Leu Asp Asn Arg His
    130                 135                 140

Ser Asn Asp Thr Ile His Asp Arg Thr Pro Phe Arg Thr Leu Leu Met
145                 150                 155                 160

Ser Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Val Thr Gly His Asp Lys Asn Ala Thr Ala Ser Phe Ile Tyr Asp
        195                 200                 205

Gly Lys Leu Val Asp Ser Ile Ser Ser Trp Ser Lys Asn Ile Leu Arg
    210                 215                 220

Thr Gln Glu Ser Glu Cys Val Cys Ile Asp Gly Ile Cys Thr Val Val
225                 230                 235                 240

Met Thr Asp Gly Ser Ala Ser Gly Lys Ala Asp Thr Lys Ile Leu Phe
                245                 250                 255

Ile Glu Lys Gly Lys Ile Ile His Ile Ser Pro Leu Leu Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Ile Val Asp
```

```
    290                 295                 300

Ile Arg Met Lys Asn Tyr Ser Ile Gly Ser Ser Tyr Met Cys Ser Gly
305                 310                 315                 320

Leu Val Gly Asp Thr Pro Arg Asn Asn Asp Gly Ser Ser Asn Ser Asn
                325                 330                 335

Cys Arg Asn Pro Asn Asn Glu Arg Gly Asn His Gly Val Lys Gly Trp
            340                 345                 350

Ala Phe Asp Asp Gly Asn Asp Thr Trp Met Gly Arg Thr Ile Ser Lys
        355                 360                 365

Asp Ser Arg Leu Gly Tyr Glu Thr Phe Lys Val Val Gly Gly Trp Ser
    370                 375                 380

Gln Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Asp
                405                 410                 415

Cys Ile Asn Arg Cys Phe Tyr Val Glu Leu Ile Arg Gly Arg Arg Gln
            420                 425                 430

Glu Thr Arg Val Trp Trp Thr Ser Asn Ser Ile Val Val Phe Cys Gly
        435                 440                 445

Thr Ser Gly Thr Tyr Gly Ser Gly Ser Trp Pro Asp Gly Ala Asn Ile
    450                 455                 460

Asn Phe Met Pro Val
465


<210> SEQ ID NO 19
<211> LENGTH: 1410
<212> TYPE: DNA
<213> ORGANISM: Influenza A virus
<220> FEATURE:
<223> OTHER INFORMATION: >KU323247.1 Influenza A virus (A/swine/Italy/
      179057/2015(H1N1)) segment 6 neuraminidase (NA) gene, complete cds

<400> SEQUENCE: 19

atgaatccaa accaaaagat aataaccatt ggttcggtct gtatgacaat tggaatggct     60

aacttaatat tacaaattgg aaacataatc tcaatatgga ttagccactc aattcaactt    120

gggaatcaaa gtcagattga aacatgcaat caaagcgtca ttacttatga aaacaacact    180

tgggtaaatc agacatatgt taacatcagc aacaccaact ttgctgctgg acagtcagtg    240

gtttccgcga aattagcggg caattcctcc ctctgccctg ttagtggatg ggctatatac    300

agtaaagaca acagtgtaag aatcggttcc aagggggatg tgtttgtcat aagggaacca    360

ttcatatcat gctccccctt agaatgcaga accttcttct tgactcaagg ggccttgcta    420

aatgacaaac attccaatgg aaccattaaa gataggagcc catatcgaac cctgatgagc    480

tgtcctattg gtgaagttcc ctctccatac aactcaagat ttgagtcggt cgcttggtca    540

gcaagtgctt gtcacgatgg catcaattgg ctaacaatcg gaatttctgg cccagacagt    600

ggggcagtgg ctgtattaaa gtacaatggc ataataacag acactatcaa gagttggaaa    660

aacaatatat tgagaacaca agagtctgaa tgtgcatgtg taaatggttc ttgctttacc    720

ataatgaccg atggaccaag tgatggacag gcctcataca agatcttcag aatagaaaag    780

ggaaagatag tcaaatcagt cgaaatgaat gcccctaatt atcactatga ggaatgctcc    840

tgttatcctg attctagtga aatcacatgt gtgtgcaggg ataactggca tggctcgaat    900

cgaccgtggg tgtctttcaa ccagaatctg gaatatcaga taggatacat atgcagtggg    960

attttcggag acaatccacg ccctaatgat aagacaggca gttgtggtcc agtatcgtct   1020
```

aatggagcaa atggagtaaa aggattttca ttcaaatatg gcaatggtgt ttggataggg 1080
agaactaaaa gcattagttc aagaaaaggt tttgagatga tttgggatcc aaatggatgg 1140
actgggacag acaaaaactt ctcaataaag caagatatca taggaataaa tgagtggtca 1200
ggatacagcg ggagttttgt tcagcatcca gaactaacag ggctgaattg tataagacct 1260
tgcttctggg ttgaactaat cagagggcga cccaaagaga acacaatctg gactagcggg 1320
agcagcatat ccttttgtgg tgtaaacagt gacactgtgg gttggtcttg gccagacggt 1380
gctgagttgc catttaccat tgacaagtaa 1410

<210> SEQ ID NO 20
<211> LENGTH: 1410
<212> TYPE: DNA
<213> ORGANISM: Artificial Sequence
<220> FEATURE:
<223> OTHER INFORMATION: >EUN1-4 Swine optimized sequence

<400> SEQUENCE: 20
atgaacccta accagaagat tattaccatc ggatccgtgt gcatgaccat cggaatggcc 60
aacctgatcc tgcaaatcgg aaacatcatc tccatctgga ttagccatag cattcagctt 120
ggaaaccaga gccagatcga gacttgtaac cagtccgtga tcacctacga gaacaacacc 180
tgggtcaacc agacttacgt caatatcagc aacaccaact tcgctgcggg gcagtccgtg 240
gtgtccgcaa agctggccgg caacagctcc ctgtgccccg tgtccggatg ggcgatctac 300
tccaaggata acagcgtgcg catcgggtcc aaaggggacg tgttcgtcat ccgcgaacca 360
ttcatttctt gctccccctt ggaatgtcgg accttcttcc tgacccaagg ggcgttgctc 420
aacgacaagc acagcaacgg aaccatcaaa gatcggtcgc cctaccgcac tctgatgtcg 480
tgccctatcg gcgaagtgcc atccccctac aactcacgct tcgagtccgt ggcctggtcc 540
gcttccgcct gccacgatgg aatcaactgg ctcacaatcg gcatctccgg cccggactcg 600
ggagccgtgg ccgtgctgaa gtacaatggt attattactg acactatcaa gtcgtggaag 660
aacaatattc tccggactca agaatctgaa tgcgcctgcg tgaacggttc ctgcttcact 720
atcatgaccg acggcccttc cgatggacag gcctcataca agatcttccg gatcgagaag 780
ggaaagatcg tgaagtccgt cgagatgaac gcaccgaact accattatga ggaatgctcg 840
tgctacccgg actcctcgga aattacttgc gtgtgccgcg acaattggca cgggtccaac 900
aggccctggg tgtccttcaa ccaaaacctg gagtaccaga tcggttacat ctgctccggg 960
atttttggag acaaccctag acctaacgac aagaccggct catgcggacc tgtgtcctcc 1020
aacggagcca acggcgtgaa gggattctcg ttcaaatatg ggaacggcgt ctggataggt 1080
cggaccaagt ccatctcgtc acggaagggc tttgaaatga tttgggaccc gaacggttgg 1140
accggaaccg acaagaactt cagcatcaag caggacatta tcggcattaa cgagtggagc 1200
ggatactcgg gcagcttcgt ccagcacccg gaacttacgg gcctcaattg tattaggccc 1260
tgtttttggg tcgagctgat tagagggcgc cccaaggaaa acaccatctg gaccagcggc 1320
tccagcatct cattctgcgg agtgaactcc gacaccgtgg gctggtcgtg gcccgacggt 1380
gccgagctgc cgttcaccat cgataaatga 1410

<210> SEQ ID NO 21
<211> LENGTH: 469
<212> TYPE: PRT
<213> ORGANISM: Influenza A virus
<220> FEATURE:

<223> OTHER INFORMATION: >ALX30323.1 neuraminidase [Influenza A virus (A/swine/Italy/179057/2015(H1N1))] EUN1-4

<400> SEQUENCE: 21

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Ser Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Ala Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Lys Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Lys Asn Phe Ser Ile Lys Gln Asp Ile Ile Gly Ile Asn Glu Trp Ser
385                 390                 395                 400
```

```
Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 22
<211> LENGTH: 1410
<212> TYPE: DNA
<213> ORGANISM: Influenza A virus
<220> FEATURE:
<223> OTHER INFORMATION: >KR700532.1 Influenza A virus (A/swine/Italy/
      28762-3/2013(H1N1)) segment 6 neuraminidase (NA) gene, complete
      cds

<400> SEQUENCE: 22

atgaacccaa atcagaagat aataatcatt agttcaatct gtatgacaaa tggaattgct      60

agcttgatat tacaaattgg gaacataata tcaatatgga ttagccattc aattcaaatt     120

gagaacccaa accagaccga accatgcaat caaagcgtta ttatttacga aaacaacaca     180

tgggtaaatc aaacgtatgt taacatcagc aacaataatt ttgttgttga acagacagtg     240

gtttcaatga aattagcggg cagttcttct ctctgccctg ttagtggatg ggctatatac     300

agtaaagata acagtgtaag aatcggttcc aaaggggatg tgtttgtcat aagagagcca     360

ttcatctcat gctcccattt ggaatgtaga accttcttct taactcaagg ggccctactg     420

aatgataaac attctaatgg aaccgttaaa gacagaagcc cctatcgaac cctgatgagc     480

tgtcctattg gtgaagtccc ctctccatac aactcaaaat ttgagtcagt tgcttggtca     540

gcaagtgctt gccatgatgg caccagttgg ttgacaattg ggatttctgg tccagacaat     600

ggagcagtgg ctgtgttgaa atacaatgac ataataacag acactatcaa gagttggaaa     660

aacaacatat tgagaacaca agaatctgaa tgtgcatgtt tgaatggttc ttgctttact     720

gtaatgaccg atggaccaag taatgggcag gcctcataca agatcttcaa aatagaaaag     780

gggaaagtag tcaaatcagt cgagttgaat gctcctaatt atcactatga ggaatgttcc     840

tgttatcctg attctggtga aatcatatgt gtatgcaggg acaattggca tggctcgaat     900

cgaccatggg tgtctttcaa tcagaatctg gagtatcaga taggatacat atgcagtggg     960

gttctcggag acaatccgcg ccctaatgat agaacaggca gttgtggtcc agtatcatct    1020

catggagcaa atggggtaaa agggttttcg tttaaatacg gcaatggaat ttggataggg    1080

agaactaaaa gcactattac aaggagtggt tttgagatga tttgggaccc aaacggatgg    1140

actggaacag acaataattt ctcagtgaag caagatatcg taggaataac taactggtca    1200

ggatacagcg ggagttttgt ccaacatcca gaattaaccg gattggattg tattagacct    1260

tgcttctggg ttgaactaat cagagggaga cccaaagaga acacaatctg gactagcgga    1320

agcagcatat ccttttgtgg tgtaaatagt gacactgtgg gttggtcttg gccagacggt    1380

gctgagttgc catttaccat tgacaagtaa                                     1410


<210> SEQ ID NO 23
<211> LENGTH: 1410
```

```
<212> TYPE: DNA
<213> ORGANISM: Artificial Sequence
<220> FEATURE:
<223> OTHER INFORMATION: >EUN1-2 Swine optimized sequence

<400> SEQUENCE: 23

atgaatccga atcagaagat cattatcatc tcctccattt gtatgactaa cggaatcgca     60

tctctgatct tgcaaattgg gaacatcatt agcatctgga tctcccactc gatccaaatc    120

gagaacccga accagaccga gccctgcaac cagagcgtga tcatatacga aaacaatacc    180

tgggtgaacc agacctatgt caatatctcg aacaacaact tcgtggtgga gcagactgtc    240

gtgtccatga agctcgccgg gtccagctcg ttgtgccctg tctccggctg ggctatctac    300

agcaaagaca acagcgtcag aatcggcagc aagggagatg tgttcgtgat ccgcgagcct    360

ttcatctcct gctcacacct ggaatgccgg acctttttcc tgacacaagg cgccctgctc    420

aatgacaagc actcgaacgg gaccgtgaag gacagaagcc cctacagaac cctgatgtcc    480

tgtccgattg gagaagtgcc ctccccgtat aactcaaagt tcgaatccgt ggcttggtca    540

gcatccgcgt gccatgacgg gaccagctgg ctgactatcg gaatctccgg tcctgacaac    600

ggcgcggtcg ccgtgctcaa gtacaacgac attatcactg acaccatcaa gtcctggaaa    660

aacaacatcc tccggaccca agagtccgag tgcgcctgcc tgaacggttc gtgtttcacc    720

gtgatgaccg atggaccaag caacggacaa gcctcgtaca agattttcaa gatcgaaaag    780

ggaaaagtgg tcaagtccgt ggagctgaac gcccctaact accactacga agagtgttca    840

tgctaccctg actccggcga aattatctgc gtgtgtcggg ataactggca cggatccaac    900

cgcccctggg tcagcttcaa ccagaacctg gaatatcaga tcggctacat ttgctccggc    960

gtgctggggg acaacccgag gccgaatgac cgcactggtt cctgcggacc cgtgtcatcc   1020

cacggggcga acggagtgaa gggtttctct ttcaaatacg gaaacggcat ctggattggc   1080

agaaccaaga gcactatcac ccggagcgga tttgagatga tctgggaccc caacggatgg   1140

accggtaccg ataacaactt ttcggtcaag caggatattg tgggcatcac taactggtcg   1200

ggatactccg gctcgttcgt gcagcatccc gagctgactg gcctggactg cattcgcccg   1260

tgcttctggg tggaacttat caggggtcgg cctaaggaga acactatctg gacctccgga   1320

tcgtcgattt ccttctgcgg cgtgaactca gataccgtgg gatggtcctg gccggacggg   1380

gccgagcttc cattcacgat tgataagtga                                    1410


<210> SEQ ID NO 24
<211> LENGTH: 469
<212> TYPE: PRT
<213> ORGANISM: Influenza A virus
<220> FEATURE:
<223> OTHER INFORMATION: >AKJ81669.1 neuraminidase [Influenza A virus
      (A/swine/Italy/28762-3/2013(H1N1))] EUN1-2

<400> SEQUENCE: 24

Met Asn Pro Asn Gln Lys Ile Ile Ile Ile Ser Ser Ile Cys Met Thr
1               5                   10                  15

Asn Gly Ile Ala Ser Leu Ile Leu Gln Ile Gly Asn Ile Ile Ser Ile
            20                  25                  30

Trp Ile Ser His Ser Ile Gln Ile Glu Asn Pro Asn Gln Thr Glu Pro
        35                  40                  45

Cys Asn Gln Ser Val Ile Ile Tyr Glu Asn Asn Thr Trp Val Asn Gln
    50                  55                  60

Thr Tyr Val Asn Ile Ser Asn Asn Asn Phe Val Val Glu Gln Thr Val
```

```
65                  70                  75                  80

Val Ser Met Lys Leu Ala Gly Ser Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Ile Gly Glu Val Pro Ser Pro Tyr Asn Ser Lys Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Asn Gly Ala Val Ala Val Leu Lys Tyr
        195                 200                 205

Asn Asp Ile Ile Thr Asp Thr Ile Lys Ser Trp Lys Asn Asn Ile Leu
    210                 215                 220

Arg Thr Gln Glu Ser Glu Cys Ala Cys Leu Asn Gly Ser Cys Phe Thr
225                 230                 235                 240

Val Met Thr Asp Gly Pro Ser Asn Gly Gln Ala Ser Tyr Lys Ile Phe
                245                 250                 255

Lys Ile Glu Lys Gly Lys Val Val Lys Ser Val Glu Leu Asn Ala Pro
            260                 265                 270

Asn Tyr His Tyr Glu Glu Cys Ser Cys Tyr Pro Asp Ser Gly Glu Ile
        275                 280                 285

Ile Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Val Leu Gly Asp Asn Pro Arg Pro Asn Asp Arg Thr Gly Ser Cys Gly
                325                 330                 335

Pro Val Ser Ser His Gly Ala Asn Gly Val Lys Gly Phe Ser Phe Lys
            340                 345                 350

Tyr Gly Asn Gly Ile Trp Ile Gly Arg Thr Lys Ser Thr Ile Thr Arg
        355                 360                 365

Ser Gly Phe Glu Met Ile Trp Asp Pro Asn Gly Trp Thr Gly Thr Asp
    370                 375                 380

Asn Asn Phe Ser Val Lys Gln Asp Ile Val Gly Ile Thr Asn Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465
```

<210> SEQ ID NO 25

-continued

```
<211> LENGTH: 13
<212> TYPE: DNA
<213> ORGANISM: Artificial Sequence
<220> FEATURE:
<223> OTHER INFORMATION: 5' flanking sequence of open reading frame

<400> SEQUENCE: 25

ggcgcgccgc acc                                                      13
```